United States Patent [19]
Goldman et al.

[11] Patent Number: 5,562,646
[45] Date of Patent: Oct. 8, 1996

[54] ABSORBENT MEMBERS FOR BODY FLUIDS HAVING GOOD WET INTEGRITY AND RELATIVELY HIGH CONCENTRATIONS OF HYDROGEL-FORMING ABSORBENT POLYMER HAVING HIGH POROSITY

[75] Inventors: Stephen A. Goldman; Herbert L. Retzsch; Todd L. Mansfield, all of Cincinnati, Ohio

[73] Assignee: The Proctor & Gamble Company, Cincinnati, Ohio

[21] Appl. No.: 416,396

[22] Filed: Apr. 6, 1995

Related U.S. Application Data

[63] Continuation-in-part of Ser. No. 219,574, Mar. 29, 1994.
[51] Int. Cl.$^6$ .............................. A61F 13/15; A61F 13/20
[52] U.S. Cl. .............................. 604/368; 604/372; 428/339
[58] Field of Search .............................. 604/358, 367–368, 604/372, 374–375; 428/290, 339

[56] References Cited

U.S. PATENT DOCUMENTS

| | | |
|---|---|---|
| Re. 32,649 | 4/1988 | Brandt et al. . |
| 4,260,443 | 4/1981 | Lindsay et al. . |
| 4,360,021 | 11/1982 | Stima . |
| 4,413,995 | 11/1983 | Korpman .............................. 604/368 |
| 4,414,255 | 11/1983 | Tokuyama et al. . |
| 4,429,001 | 1/1984 | Kolpin et al. . |
| 4,446,261 | 5/1984 | Yamasaki et al. . |
| 4,461,621 | 7/1984 | Karami et al. .............................. 604/368 |
| 4,467,012 | 8/1984 | Pedersen et al. . |
| 4,500,315 | 2/1985 | Pleniak et al. . |
| 4,500,670 | 2/1985 | McKinley et al. . |
| 4,537,590 | 8/1985 | Pieniak et al. . |
| 4,541,871 | 9/1985 | Obayashi et al. . |
| 4,551,191 | 11/1985 | Kock et al. . |
| 4,578,068 | 3/1986 | Kramer et al. . |
| 4,587,308 | 5/1986 | Makita et al. . |
| 4,600,458 | 7/1986 | Kramer et al. . |
| 4,604,313 | 8/1986 | McFarland et al. . |
| 4,605,401 | 8/1986 | Chmelir et al. . |
| 4,610,678 | 9/1986 | Weisman et al. . |
| 4,625,001 | 11/1986 | Tsubakimoto et al. . |
| 4,647,617 | 3/1987 | Saotome . |
| 4,650,479 | 3/1987 | Insley . |
| 4,654,039 | 3/1987 | Brandt et al. . |
| 4,655,757 | 4/1987 | McFarland et al. . |
| 4,690,971 | 9/1987 | Flesher et al. . |
| 4,693,713 | 9/1987 | Chmelir et al. . |
| 4,698,404 | 10/1987 | Cramm et al. . |

(List continued on next page.)

FOREIGN PATENT DOCUMENTS

| | | |
|---|---|---|
| 0493011A2 | 7/1992 | European Pat. Off. . |
| 0509708A1 | 10/1992 | European Pat. Off. . |
| 0555692A1 | 8/1993 | European Pat. Off. . |
| 2267094 | 11/1993 | United Kingdom . |
| WO90/08789 | 8/1990 | WIPO . |
| WO92/16565 | 10/1992 | WIPO . |
| WO94/01069 | 1/1994 | WIPO . |

*Primary Examiner*—Michael J. Milano
*Assistant Examiner*—P. Zuttarelli
*Attorney, Agent, or Firm*—Eric W. Guttag; Carl J. Roof; E. Kelly Linman

[57] ABSTRACT

Absorbent members useful in the containment of body fluids such as urine, that have at least one region containing hydrogel-forming absorbent polymer in a concentration of from about 60 to 100% by weight and providing a gel-continuous fluid transportation zone when in a swollen state. This hydrogel-forming absorbent polymer has: (a) a porosity of at least about 0.15; (b) a Performance under Pressure (PUP) capacity value of at least about 23 g/g under a confining pressure of 0.7 psi (5 kPa); (c) a basis weight of at least about 10 gsm; and (d) optionally, but preferably, a Saline Flow Conductivity (SFC) value of at least about $30 \times 10^{-7}$ cm$^3$ sec/g. In addition, the region where this hydrogel-forming absorbent polymer is present has, even when subjected to normal use conditions, sufficient wet integrity such that the gel-continuous zone substantially maintains its ability to acquire and transport body fluids through the gel-continuous zone.

45 Claims, 11 Drawing Sheets

U.S. PATENT DOCUMENTS

| | | |
|---|---|---|
| 4,715,918 | 12/1987 | Lang . |
| 4,724,114 | 2/1988 | McFarland et al. . |
| 4,734,478 | 3/1988 | Tsubakimoto et al. . |
| 4,755,562 | 7/1988 | Alexander et al. . |
| 4,758,617 | 7/1988 | Tanioku et al. . |
| 4,766,173 | 8/1988 | Bailey et al. . |
| 4,777,200 | 10/1988 | Dymond et al. . |
| 4,783,510 | 11/1988 | Saotome . |
| 4,786,550 | 11/1988 | McFarland et al. . |
| 4,797,318 | 1/1989 | Brooker et al. . |
| 4,820,773 | 4/1989 | Alexander et al. . |
| 4,824,901 | 4/1989 | Alexander et al. . |
| 4,833,179 | 5/1989 | Young et al. . |
| 4,834,735 | 5/1989 | Alemany et al. . |
| 4,851,069 | 7/1989 | Packard et al. . |
| 4,861,349 | 8/1989 | Bublik et al. . |
| 4,861,539 | 8/1989 | Allen et al. . |
| 4,880,858 | 11/1989 | Farrar et al. . |
| 4,902,559 | 2/1990 | Eschwey et al. . |
| 4,904,249 | 2/1990 | Miller et al. . |
| 4,921,904 | 5/1990 | Sparapany et al. . |
| 4,923,454 | 5/1990 | Seymour et al. . |
| 4,950,264 | 8/1990 | Osborn, III . |
| 4,950,692 | 8/1990 | Lewis et al. . |
| 4,954,562 | 9/1990 | Anderson . |
| 4,962,172 | 10/1990 | Allen et al. . |
| 4,970,267 | 11/1990 | Bailey et al. . |
| 4,980,434 | 12/1990 | Farrar et al. . |
| 4,985,298 | 1/1991 | Buckley et al. . |
| 4,997,714 | 3/1991 | Farrar et al. . |
| 5,009,653 | 4/1991 | Osborn, III . |
| 5,047,023 | 9/1991 | Berg . |
| 5,047,166 | 10/1991 | Young, Sr. et al. . |
| 5,061,259 | 10/1991 | Goldman et al. . |
| 5,064,689 | 11/1991 | Young, Sr. et al. . |
| 5,079,080 | 1/1992 | Schwartz . |
| 5,102,597 | 4/1992 | Roe et al. . |
| 5,118,719 | 6/1992 | Lind . |
| 5,122,544 | 6/1992 | Bailey et al. . |
| 5,124,188 | 6/1992 | Roe et al. . |
| 5,128,082 | 7/1992 | Makoui . |
| 5,143,680 | 9/1992 | Molnar et al. . |
| 5,145,727 | 9/1992 | Potts et al. . |
| 5,147,956 | 9/1992 | Allen . |
| 5,149,334 | 9/1992 | Lahrman et al. . |
| 5,149,335 | 9/1992 | Kellenberger et al. . |
| 5,154,713 | 10/1992 | Lind . |
| 5,160,331 | 11/1992 | Forester et al. . |
| 5,171,781 | 12/1992 | Farrar et al. . |
| 5,180,622 | 1/1993 | Berg et al. . |
| 5,206,205 | 4/1993 | Tsai . |
| 5,227,107 | 7/1993 | Dickenson et al. . |
| 5,230,959 | 7/1993 | Young, Sr. et al. . |
| 5,262,223 | 11/1993 | Palumbo et al. . |
| 5,264,471 | 11/1993 | Chmelir . |
| 5,280,079 | 1/1994 | Allen et al. . |
| 5,286,827 | 2/1994 | Ahmed . |
| 5,314,420 | 5/1994 | Smith et al. . |

ABSORBENT MEMBERS FOR BODY FLUIDS HAVING GOOD WET INTEGRITY AND RELATIVELY HIGH CONCENTRATIONS OF HYDROGEL-FORMING ABSORBENT POLYMER HAVING HIGH POROSITY

CROSS-REFERENCE TO RELATED APPLICATION

This application is a continuation-in-part of copending U.S. application Ser. No. 08/219,574, filed Mar. 29, 1994.

TECHNICAL FIELD

This application relates to absorbent members for body fluids such as urine and menses having good wet integrity. This application further relates to absorbent members having at least one region with a relatively high concentration of hydrogel-forming absorbent polymer.

BACKGROUND OF THE INVENTION

The development of highly absorbent members for use as disposable diapers, adult incontinence pads and briefs, and catamenial products such as sanitary napkins, are the subject of substantial commercial interest. A highly desired characteristic for such products is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as diapers has been contingent on the ability to develop relatively thin absorbent cores or structures that can acquire and store large quantities of discharged body fluids, in particular urine. In this regard, the use of certain absorbent polymers often referred to as "hydrogels," "superabsorbents" or "hydrocolloid" material has been particularly important. See, for example, U.S. Pat. No. 3,699,103 (Harper et al), issued Jun. 13, 1972, and U.S. Pat. No. 3,770,731 (Harmon), issued Jun. 20, 1972, that disclose the use of such absorbent polymers (hereafter "hydrogel-forming absorbent polymers") in absorbent articles. Indeed, the development of thinner diapers has been the direct consequence of thinner absorbent cores that take advantage of the ability of these hydrogel-forming absorbent polymers to absorb large quantities of discharged body fluids, typically when used in combination with a fibrous matrix. See, for example, U.S. Pat. No. 4,673,402 (Weisman et al), issued Jun. 16, 1987 and U.S. Pat. No. 4,935,022 (Lash et al), issued Jun. 19, 1990, that disclose dual-layer core structures comprising a fibrous matrix and hydrogel-forming absorbent polymers useful in fashioning thin, compact, nonbulky diapers.

Prior to the use of these hydrogel-forming absorbent polymers, it was general practice to form absorbent structures, such as those suitable for use in infant diapers, entirely from wood pulp fluff. Given the relatively low amount of fluid absorbed by wood pulp fluff on a gram of fluid absorbed per gram of wood pulp fluff, it was necessary to employ relatively large quantities of wood pulp fluff, thus necessitating the use of relatively bulky, thick absorbent structures. The introduction of these hydrogel-forming absorbent polymers into such structures has allowed the use of less wood pulp fluff. These hydrogel-forming absorbent polymers are superior to fluff in their ability to absorb large volumes of aqueous body fluids, such as urine (i.e., at least about 15 g/g), thus making smaller, thinner absorbent structures feasible.

These hydrogel-forming absorbent polymers are often made by initially polymerizing unsaturated carboxylic acids or derivatives thereof, such as acrylic acid, alkali metal (e.g., sodium and/or potassium) or ammonium salts of acrylic acid, alkyl acrylates, and the like. These polymers are rendered water-insoluble, yet water-swellable, by slightly cross-linking the carboxyl group-containing polymer chains with conventional di- or poly-functional monomer materials, such as N,N'-methylenebisacrylamide, trimethylol propane triacrylate or triallyl amine. These slightly crosslinked absorbent polymers still comprise a multiplicity of anionic (charged) carboxyl groups attached to the polymer backbone. It is these charged carboxy groups that enable the polymer to absorb body fluids as the result of osmotic forces, thus forming hydrogels.

The degree of cross-linking determines not only the water-insolubility of these hydrogel-forming absorbent polymers, but is also an important factor in establishing two other characteristics of these polymers: their absorbent capacity and gel strength. Absorbent capacity or "gel volume" is a measure of the amount of water or body fluid that a given amount of hydrogel-forming polymer will absorb. Gel strength relates to the tendency of the hydrogel formed from these polymers to deform or "flow" under an applied stress. Hydrogel-forming polymers useful as absorbents in absorbent structures and articles such as disposable diapers need to have adequately high gel volume, as well as adequately high gel strength. Gel volume needs to be sufficiently high to enable the hydrogel-forming polymer to absorb significant mounts of the aqueous body fluids encountered during use of the absorbent article. Gel strength needs to be such that the hydrogel formed does not deform and fill to an unacceptable degree the capillary void spaces in the absorbent structure or article, thereby inhibiting the absorbent capacity of the structure/article, as well as the fluid distribution throughout the structure/article. See, for example, U.S. Pat. No. 4,654,039 (Brandt et al), issued Mar. 31, 1987 (reissued Apr. 19, 1988 as U.S. Re. Pat. No. 32,649) and U.S. Pat. No. 4,834,735 (Alemany et al), issued May 30, 1989.

Prior absorbent structures have generally comprised relatively low amounts (e.g., less than about 50% by weight) of these hydrogel-forming absorbent polymers. See, for example, U.S. Pat. No. 4,834,735 (Alemany et al), issued May 30, 1989 (preferably from about 9 to about 50% hydrogel-forming absorbent polymer in the fibrous matrix). There are several reasons for this. The hydrogel-forming absorbent polymers employed in prior absorbent structures have generally not had an absorption rate that would allow them to quickly absorb body fluids, especially in "gush" situations. This has necessitated the inclusion of fibers, typically wood pulp fibers, to serve as temporary reservoirs to hold the discharged fluids until absorbed by the hydrogel-forming absorbent polymer.

More importantly, many of the known hydrogel-forming absorbent polymers exhibited gel blocking. "Gel blocking" occurs when particles of the hydrogel-forming absorbent polymer are wetted and the particles swell so as to inhibit fluid transmission to other regions of the absorbent structure. Wetting of these other regions of the absorbent member therefore takes place via a very slow diffusion process. In practical terms, this means acquisition of fluids by the absorbent structure is much slower than the rate at which fluids are discharged, especially in gush situations. Leakage from the absorbent article can take place well before the particles of hydrogel-forming absorbent polymer in the absorbent member are fully saturated or before the fluid can diffuse or wick past the "blocking" particles into the rest of the absorbent member. Gel blocking can be a particularly acute problem if the particles of hydrogel-forming absorbent polymer do not have adequate gel strength and deform or spread under stress once the particles swell with absorbed fluid. See U.S. Pat. No. 4,834,735 (Alemany et al), issued May 30, 1989.

This gel blocking phenomena has typically necessitated the use of a fibrous matrix in which are dispersed the particles of hydrogel-forming absorbent polymer. This fibrous matrix keeps the particles of hydrogel-forming absorbent polymer separated from one another. This fibrous matrix also provides a capillary structure that allows fluid to reach the hydrogel-forming absorbent polymer located in regions remote from the initial fluid discharge point. See U.S. Pat. No. 4,834,735 (Alemany et al), issued May 30, 1989. However, dispersing the hydrogel-forming absorbent polymer in a fibrous matrix at relatively low concentrations in order to minimize or avoid gel blocking can lower the overall fluid storage capacity of thinner absorbent structures. Using lower concentrations of these hydrogel-forming absorbent polymers limits somewhat the real advantage of these materials, namely their ability to absorb and retain large quantities of body fluids per given volume.

Besides increasing gel strength, other physical and chemical characteristics of these hydrogel-forming absorbent polymers have been manipulated to decrease gel blocking. One characteristic is the particle size, and especially the particle size distribution, of the hydrogel-forming absorbent polymer used in the fibrous matrix. For example, particles of hydrogel-forming absorbent polymer having a particle size distribution such that the particles have a mass median particle size greater than or equal to about 400 microns have been mixed with hydrophilic fibrous materials to minimize gel blocking and to help maintain an open capillary structure within the absorbent structure so as to enhance planar transport of fluids away from the area of initial discharge to the rest of the absorbent structure. In addition, the particle size distribution of the hydrogel-forming absorbent polymer can be controlled to improve absorbent capacity and efficiency of the particles employed in the absorbent structure. See U.S. Pat. No. 5,047,023 (Berg), issued Sep. 10, 1991. However, even adjusting the particle size distribution does not, by itself, lead to absorbent structures that can have relatively high concentrations of these hydrogel-forming absorbent polymers. See U.S. Pat. No. 5,047,023, supra (optimum fiber to particle ratio on cost/performance basis is from about 75:25 to about 90:10).

Another characteristic of these hydrogel-forming absorbent polymers that has been looked at is the level of extractables present in the polymer itself. See U.S. Pat. No. 4,654,039 (Brandt et al), issued Mar. 31, 1987 (reissued Apr. 19, 1988 as U.S. Re. Pat. No. 32,649). Many of these hydrogel-forming absorbent polymers contain significant levels of extractable polymer material. This extractable polymer material can be leached out from the resultant hydrogel by body fluids (e.g., urine) during the time period such body fluids remain in contact with the hydrogel-forming absorbent polymer. It is believed such polymer material extracted by body fluid in this manner can alter both the chemical and physical characteristics of the body fluid to the extent that the fluid is more slowly absorbed and more poorly held by the hydrogel in the absorbent article.

Another characteristic that has been looked at to minimize gel blocking is to improve the capillary capability of these hydrogel-forming absorbent polymers. In particular, it has been suggested that particles of these hydrogel-forming absorbent polymers be formed into interparticle crosslinked aggregate macrostructures, typically in the form of sheets or strips. See U.S. Pat. No. 5,102,597 (Roe et al), issued Apr. 7, 1992; U.S. Pat. No. 5,124,188 (Roe et al), issued Jun. 23, 1992; and U.S. Pat. No. 5,149,344 (Lahrman et al), issued Sep. 22, 1992. Because the particulate nature of the absorbent polymer is retained, these macrostructures provide pores between adjacent particles that are interconnected such that the macrostructure is fluid permeable (i.e., has capillary transport channels). Due to the interparticle crosslink bonds formed between the particles, the resultant macrostructures also have improved structural integrity, increased fluid acquisition and distribution rates, and minimal gel blocking characteristics.

Yet another characteristic the art has known for some time as a measure of gel blocking is the Demand Wettability or Gravimetric Absorbence of these hydrogel-forming absorbent polymers. See, for example, U.S. Pat. No. 5,147,343 (Kellenberger), issued Sep. 15, 1992 and U.S. Pat. No. 5,149,335 (Kellenberger et al), issued Sep. 22, 1992 where these hydrogel-forming absorbent polymers are referred to as "superabsorbent materials" and where Demand Wettability/Gravimetric Absorbence is referred to as Absorbency Under Load (AUL). "AUL" is defined in these patents as the ability of the hydrogel-forming absorbent polymer to swell against an applied restraining force (see U.S. Pat. No. 5,147,343, supra, at Col. 2, lines 43–46). The "AUL value" is defined as the amount (in ml./g or g/g.) of 0.9% saline solution that is absorbed by the hydrogel-forming absorbent polymers while being subjected to a load of 21,000 dynes/$cm^2$ (about 0.3 psi). The AUL value can be determined at 1 hour (see U.S. Pat. No. 5,147,343) or 5 minutes (see U.S. Pat. No. 5,149,335). Hydrogel-forming absorbent polymers are deemed to have desirable AUL properties if they absorb at least about 24 ml./g (preferably at least about 27 ml./g) of the saline solution after 1 hour (see U.S. Pat. No. 5,147,343) or at least about 15 g/g (preferably at least about 18 g/g) of the saline solution after 5 minutes.

AUL as defined in U.S. Pat. Nos. 5,147,343 and 5,149,335 may provide some indication of which hydrogel-forming absorbent polymers will avoid gel blocking in some instances. However, AUL is inadequate for determining which hydrogel-forming absorbent polymers will provide the absorbency properties necessary so that the concentration of these polymers in absorbent structures can be increased without significant gel blocking or some other undesirable effect. Indeed, certain of the hydrogel-forming absorbent polymers disclosed in U.S. Pat. Nos. 5,147,343 and 5,149,335 as having satisfactory AUL values will have inadequate permeability to be useful at high concentrations in absorbent members. In order to have a high AUL value, it is only necessary that the hydrogel layer formed have at least minimal permeability such that, under a confining pressure of 0.3 psi, gel blocking does not occur to any significant degree. The degree of permeability needed to simply avoid gel blocking is much less than that needed to provide good fluid transportation properties. Hydrogel-forming absorbent polymers that avoid gel blocking can still be greatly deficient in other fluid handling properties.

Another problem with using AUL values measured according to U.S. Pat. Nos. 5,147,343 and 5,149,335 is that they do not reflect all of the potential pressures that can be operative on the hydrogel-forming polymer in the absorbent structure. As noted above, AUL is measured in these patents at a pressure of about 0.3 psi. It is believed that a much higher confining pressure of about 0.7 psi more adequately reflects the full range of localized mechanical pressures (e.g., sitting, sleeping, squatting, taping, elastics, leg motions, other tension and torsional motions) on an absorbent structure. See U.S. Pat. No. 5,147,345 (Young et al), issued Sep. 15, 1992. Additionally, many of the absorbent structures that comprise these hydrogel-forming absorbent polymers can include other components, such as an acquisition layer that receives the initial discharge of body fluids. See, for example, U.S. Pat. No. 4,673,402 (Weisman et al), issued Jun. 16, 1987 and U.S. Pat. No. 4,935,022 (Lash et al), issued Jun. 19, 1990. This acquisition layer can comprise fibers, such as certain chemically stiffened fibers, that have a relatively high capillary suction. See, for example, U.S. Pat. No. 5,217,445 (Young et al), issued Jun. 8, 1993. To take into account these additional capillary pressures that could affect fluid acquisition by these hydrogel-forming absorbent polymers, it is more realistic to measure demand absorbency performance under a higher pressure, i.e., about 0.7 psi. This would take into better account not only the localized mechanical pressures exerted during use, but also the additional capillary pressures resulting from other components (e.g., acquisition layer) present in the absorbent structure.

For absorbent structures having relatively high concentrations of these hydrogel-forming absorbent polymers, other characteristics of these absorbent polymers have been evaluated. See, for example, European patent application 532,002 (Byedy et al), published Mar. 17, 1993, which identifies a characteristic called Deformation Under Load (DUL) as being important for absorbent composites having high concentrations of hydrogel-forming absorbent polymers. "DUL" is used in European patent application 532,002 to evaluate the ability of the hydrogel-forming absorbent polymer to maintain wicking channels after the absorbent polymer is swollen. See page 3, lines 9–10. DUL values are obtained by incompletely saturating the hydrogel-forming absorbent polymer with a fixed amount of synthetic urine, compressing the absorbent polymer under a light load (0.3 psi), and then measuring the deformation of the absorbent polymer under a heavier load (0.9 psi). See page 5, lines 37–40. Hydrogel-forming absorbent polymers having DUL values of about 0.6 mm or less (preferably about 0.5 mm or less, most preferably about 0.3 mm or less) are deemed to be desirable. See page 4, lines 1–3.

DUL as defined in European patent application 532,002 may provide some indication of the ability of hydrogel-forming absorbent polymer to maintain wicking channels after the absorbent polymer is swollen. However, it has been found that the openness or porosity of the hydrogel layer formed when these absorbent polymers swell in the presence of body fluids is more relevant than DUL values for determining the ability of these absorbent polymers to acquire and transport fluids, especially when the absorbent polymer is present at high concentrations in the absorbent structure. Porosity refers to the fractional volume that is not occupied by solid material. For a hydrogel layer formed entirely from a hydrogel-forming absorbent polymer, porosity is the fractional volume of the layer that is not occupied by hydrogel. For an absorbent structure containing the hydrogel, as well as other components, porosity is the fractional volume (also referred to as void volume) that is not occupied by the hydrogel, or other solid components (e.g., fibers).

Importantly, it has been found that hydrogel-forming absorbent polymers having higher porosities than those apparently desired by European patent application 532,002 are particularly suitable for absorbent structures having high concentrations of these absorbent polymers. (It is believed that hydrogel-forming absorbent polymers having DUL values below about 0.6 mm that are desired by European patent application 532,002 have relatively low porosities. It is also believed that hydrogel-forming absorbent polymers having relatively high porosities have DUL values above about 0.6 mm.) The openness or porosity of a hydrogel layer formed from a hydrogel-forming absorbent polymer can be defined in terms of Porosity of the Hydrogel Layer (PHL). A good example of a material having a very-high degree openness is an air-laid web of wood-pulp fibers. For example, the fractional degree of openness of an air-laid web of wood pulp fibers (e.g., having a density of 0.15 g/cc) is estimated to be 0.8–0.9, when wetted with body fluids under a confining pressure of 0.3 psi. By contrast, typical hydrogel-forming polymers such as Nalco 1180 (made by Nalco Chemical Co.) and L-761f (made by Nippon Shokubai Co., LTD) exhibit PHL values of about 0.1 or less Moreover, it has been found that the PIE value of the hydrogel-forming absorbent polymer does not have to approach that of an air-laid web of wood pulp fibers in order to obtain substantial performance benefits when these absorbent polymers are present at high concentrations. These benefits include (1) increased void volume in the resultant hydrogel layer for acquiring and distributing fluid; and (2) increased total quantity of fluid absorbed by the absorbent polymer under demand wettability/gravimetric absorbency conditions (i.e., for the storage of fluid). Increased porosity can also provide additional performance benefits such as: (3) increased permeability of the resultant hydrogel layer for acquiring and distributing fluid; (4) improved wicking properties for the resultant hydrogel layer, such as wicking fluid upwardly against gravitational pressures or partitioning fluid away from an acquisition layer; and (5) improved swelling-rate properties for the resultant hydrogel layer to allow more-rapid storage of fluid.

Another important property at higher concentrations of these hydrogel-forming absorbent polymers is their permeability/flow conductivity. Permeability/flow conductivity can be defined in terms of their Saline Flow Conductivity (SFC) values. SFC measures the ability of a material to transport saline fluids, such as the ability of the hydrogel layer formed from the swollen hydrogel-forming absorbent polymer to transport body fluids. Typically, an air-laid web of pulp fibers (e.g., having a density of 0.15 g/cc) will exhibit an SFC value of about $200 \times 10^{-7}$ cm$^3$ sec/g. By contrast, typical hydrogel-forming absorbent polymers such as Aqualic L-74 (made by Nippon Shokubai Co., LTD) and Nalco-1180 (made by Nalco Chemical Co.) exhibit SFC values of at most $1 \times 10^{-7}$ cm$^3$ sec/g. Accordingly, it would be highly desirable to be able to use hydrogel-forming absorbent polymers that more closely approach an air-laid web of wood pulp fibers in terms of SFC.

Another factor that has to be considered in order to take full advantage of the porosity and permeability properties of the hydrogel layer formed from these absorbent polymers is the wet integrity of the region or regions in the absorbent member that comprise these polymers. For hydrogel-forming absorbent polymers having relatively high porosity and SFC values, it is extremely important that the region(s) in which polymers are present have good wet integrity. By "good wet integrity" is meant that the region or regions in the absorbent member having the high concentration of hydrogel-forming absorbent polymer have sufficient integrity in a dry, partially wet, and/or wetted state such that the physical continuity (and thus the capability of acquiring and transporting fluid into and through contiguous interstitial voids/capillaries) of the hydrogel formed upon swelling in the presence of body fluids is not substantially disrupted or altered, even when subjected to normal use conditions. During normal use, absorbent cores in absorbent articles are typically subjected to tensional and torsional forces of varying intensity and direction. These tensional and torsional forces include bunching in the crotch area, stretching and twisting forces as the person wearing the absorbent article walks, squats, bends, and the like. If wet integrity is inadequate, these tensional and torsional forces can potentially cause a substantial alteration and/or disruption in the physical continuity of the hydrogel such that its capability of acquiring and transporting fluids into and through the contiguous voids and capillaries is degraded, e.g., the hydrogel layer can be partially separated, fully separated, have gaps introduced, have areas that are significantly thinned, and/or broken up into a plurality of significantly smaller segments. Such alteration could minimize or completely negate any advantageous porosity and permeability/flow conductivity properties of the hydrogel-forming absorbent polymer.

Accordingly, it would be desirable to be able to provide an absorbent member comprising: (1) a region or regions having a relatively high concentration of hydrogel-forming absorbent polymer; (2) with relatively high porosities, and preferably permeability/flow conductivity properties more like an air-laid fibrous web; (3) that can readily acquire fluids from even high capillary suction acquisition layers under typical usage pressures; (4) in a matrix that provides sufficient wet integrity such that its capability for acquiring and transporting fluids is not substantially reduced or minimized, even when subjected to normal use forces. It would also be highly desirable to be able to use hydrogel-forming absorbent polymers in these absorbent members that, when swollen by body fluids, have higher PHL values such that: (a) the void volume per unit weight of absorbent polymer is closer to that of an air-laid fibrous web; (b) the demand wettability or gravimetric absorbency of the absorbent polymer under usage pressures is increased; and (c) the absorbent member preferably has increased permeability, improved wicking and/or improved swelling-rate properties.

DISCLOSURE OF THE INVENTION

The present invention relates to absorbent members useful in the containment of body fluids such as urine. These absorbent members comprise at least one region having hydrogel-forming absorbent polymer in a concentration of from about 60 to 100% by weight and providing a gel-continuous fluid transportation zone when in a swollen state. This hydrogel-forming absorbent polymer has:

(a) a porosity of at least about 0.15;
(b) a Performance under Pressure (PUP) capacity value of at least about 23 g/g under a confining pressure of 0.7 psi (5 kPa);
(c) a basis weight of at least about 10 gsm.
(d) optionally, but preferably, a Saline Flow Conductivity (SFC) value of at least about $30 \times 10^{-7}$ cm$^3$ sec/g;

In addition, the region where this hydrogel-forming absorbent polymer is present has, even when subjected to normal use conditions, sufficient wet integrity such that the gel-continuous zone substantially maintains its ability to acquire and transport body fluids through the gel-continuous zone.

DETAILED DESCRIPTION OF THE INVENTION

A. Definitions

Figure 1:
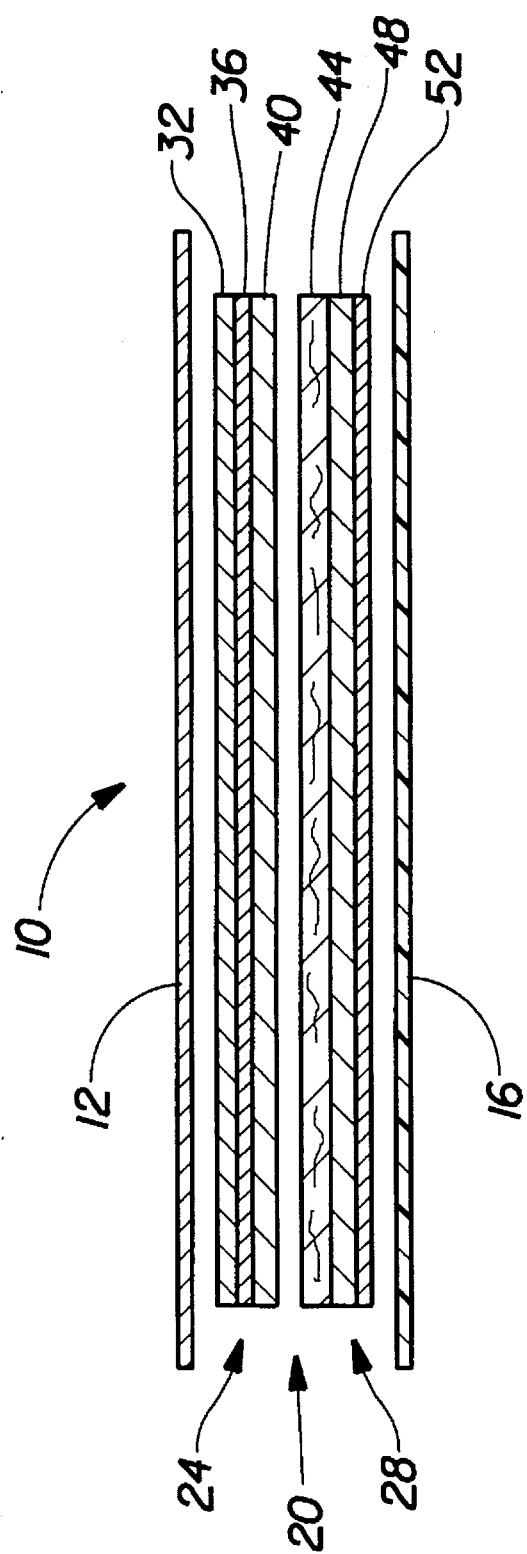
FIG. 1 is a cross-sectional view of an absorbent article showing an absorbent core according to the present invention.

As used herein, the term "body fluids" includes urine, menses and vaginal discharges.

As used herein, the term "Z-dimension" refers to the dimension orthogonal to the length and width of the member, core or article. The Z-dimension usually corresponds to the thickness of the member, core or article.

As used herein, the term "X-Y dimension" refers to the plane orthogonal to the thickness of the member, core or article. The X-Y dimension usually corresponds to the length and width of the member, core or article.

As used herein, the term "absorbent core" refers to the component of the absorbent article that is primarily responsible for fluid handling properties of the article, including acquiring, transporting, distributing and storing body fluids. As such, the absorbent core typically does not include the topsheet or backsheet of the absorbent article.

As used herein, the term "absorbent member" refers to the components of the absorbent core that typically provide one or more fluid handling properties, e.g., fluid acquisition, fluid distribution, fluid transportation, fluid storage, etc. The absorbent member can comprise the entire absorbent core or only a portion of the absorbent core, i.e., the absorbent core can comprise one or more absorbent members.

As used herein, the terms "region(s)" or "zone(s)" refer to portions or sections of the absorbent member.

As use herein, the term "layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered."

For purposes of this invention, it should also be understood that the term "upper" refers to absorbent members, such as layers, that are nearest to the wearer of the absorbent article, and typically face the topsheet of an absorbent article; conversely, the term "lower" refers to absorbent members that are furthermost away from the wearer of the absorbent article and typically face the backsheet.

As used herein, the term "comprising" means various components, members, steps and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios and proportions used herein are by weight unless otherwise specified.

B. Material and Components of the Absorbent Member

1. Hydrogel Forming Absorbent Polymers a. Chemical Composition

The hydrogel-forming absorbent polymers useful in the present invention include a variety of water-insoluble, but water-swellable polymers capable of absorbing large quantities of fluids. Such polymers materials are also commonly referred to as "hydrocolloids," or "superabsorbent" materials and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, hydrogel-forming absorbent polymers useful in the present invention have a multiplicity of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et al), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, α-chloroacrylic acid, a-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitfile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitfile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. Nos. 3,661,875, 4,076,663, 4,093,776, 4,666,983, and 4,734,478.

Most preferred polymer materials for use in making the hydrogel-forming absorbent polymers are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the hydrogel-forming absorbent polymers. Processes for network crosslinking these polymers and typical network crosslinking agents are described in greater detail in U.S. Pat. No. 4,076,663.

While the hydrogel-forming absorbent polymer is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention.

The hydrogel-forming absorbent polymers useful in the present invention can have a size, shape and/or morphology varying over a wide range. These polymers can be in the form of particles that do not have a large ratio of greatest dimension to smallest dimension (e.g., granules, pulverulents, interparticle aggregates, interparticle crosslinked aggregates, and the like) and can be in the form of fibers, sheets, films, foams, flakes and the like. The hydrogel-forming absorbent polymers can also comprise mixtures with low levels of one or more additives, such as for example powdered silica, surfactants, glue, binders, and the like. The components in this mixture can be physically and/or chemically associated in a form such that the hydrogel-forming polymer component and the non-hydrogel-forming polymer additive are not readily physically separable.

The hydrogel-forming absorbent polymers can be essentially non-porous (i.e., no internal porosity) or have substantial internal porosity.

For particles as described above, particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S., Series Alternate Sieve Designation) is considered to have a particle size between 500 and 710 microns; and a particle that passes through a sieve with 500 micron openings is considered to have a size less than 500 microns. The mass median particle size of a given sample of hydrogel-forming absorbent polymer particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the hydrogel-forming absorbent polymer particles are further described in U.S. Pat. No. 5,061,259 (Goldman et. al), issued Oct. 29, 1991, which is incorporated by reference.

For particles of hydrogel-forming absorbent polymers useful in the present invention, the particles will generally range in size from about 1 to about 2000 microns, more preferably from about 20 to about 1000 microns. The mass median particle size will generally be from about 20 to about 1500 microns, more preferably from about 50 microns to about 1000 microns, and even more preferably from about 100 to about 800 microns.

Within these size ranges, it can be preferable to choose either larger or smaller particles depending on the need for faster or slower absorption kinetics. For example, for non-porous particles, the swelling rate will generally decrease with increasing particle size. It can also be preferable to choose either larger or smaller particles or narrower size cuts (fractions) of larger or smaller particles from the bulk polymer in order to increase the porosity (i.e., increase the PHL value), increase the gel layer permeability (i.e., increase the Saline Flow Conductivity (SFC) value), improve wicking properties, etc. For particles of some hydrogel-forming absorbent polymers, it has been found that narrower size range cuts containing generally larger particle sizes within the above specified size ranges have higher SFC values without any significant degradation in other hydrogel-forming absorbent polymer properties such as PHL, Performance Under Pressure (PUP) capacity and level of extractable polymer. Thus, for example, it can be useful to use a size cut having a mass median size in the range of from about 500 to about 710 microns wherein only minimal mass fractions of the particulates have sizes either greater than about 710 microns or less than about 500 microns. Alternatively, a broader size cut wherein the particles generally have a size in the range of from about 300 microns to about 800 microns can be useful.

Within these size ranges, it can be desirable to choose particles having internal porosity capable of contributing to a faster swelling of the hydrogel-forming polymer by body fluids. Internal porosity within the hydrogel-forming polymer particle can also contribute to the PHL value of the resultant hydrogel layer. Changes in this component of the total PHL value may have a smaller impact on some fluid-handling properties dependent on PHL (e.g., SFC) than changes in the component of the PHL value arising from voids between swollen hydrogel-forming polymer particles in the hydrogel layer.

b. Physical Properties (1). Porosity of Hydrogel Zone or Layer

An important characteristic of the hydrogel-forming absorbent polymers useful in the present invention is the openness or porosity of the hydrogel zone or layer formed when the polymer is swollen in body fluids under a confining pressure. It is believed that when a hydrogel-forming absorbent polymer is present at high concentrations in an absorbent member and then swells to form a hydrogel under usage pressures, the boundaries of the hydrogel come into contact, and interstitial voids in this high-concentration region become generally bounded by hydrogel. When this occurs, it is believed the openness or porosity properties of this region are generally reflective of the porosity of the hydrogel zone or layer formed from the hydrogel-forming absorbent polymer alone. As used herein, the term "porosity" means the fractional volume (dimension-less) that is not occupied by solid material. See J. M. Coulson et. al., Chemical Engineering Vol. 2, 3rd Edition, Pergamon Press, 1978, P126. For a hydrogel zone or layer formed entirely from a hydrogel-forming absorbent polymer, porosity is the fractional volume of the zone/layer that is not occupied by hydrogel. For a region of an absorbent member containing the hydrogel, as well as other components, porosity is the fractional volume of the region (also referred to as void volume that includes the interstitial volume between swollen hydrogel-forming polymer plus any volume within swollen hydrogel-forming polymer (i.e., internal porosity)) that is not occupied by the hydrogel, or other solid components (e.g., fibers). Porosity of an absorbent region is equal to the ratio of the void volume within the region to the total volume of the region.

Porosity is defined herein in terms of the Porosity of Hydrogel Layer (PHL) value of the hydrogel-forming absorbent polymer. PHL measures the ability of the formed hydrogel zone or layer to remain open so as to be able to acquire and distribute body fluids under usage pressures. It is further believed that increasing the porosity of these swollen high-concentration regions to higher levels can provide superior absorption and fluid handling properties for the absorbent member and absorbent core, thus decreasing incidents of leakage, especially at high fluid loadings. Desirably the per gram void volume contained by voids within the hydrogel zone or layer approaches or even exceeds the per gram void volume contained within conventional acquisition/distribution materials such as wood-pulp fluff. (Higher PHL values are also reflective of the ability of the formed hydrogel to acquire body fluids under normal usage conditions.)

Porosity of the hydrogel zone or layer is also important because of its impact on the demand wettability or gravimetric absorbency capacity (i.e., PUP capacity). Generally, the additional void volume generated by a higher porosity under a confining pressure directly contributes to a higher value for PUP capacity. It can also contribute to a higher PUP capacity through its impact on the chemical composition of the fluid contained in the voids within the hydrogel layer. Thus, for example, an increase in void volume within the hydrogel layer can reduce the concentration of salts (i.e., by dilution), including simple salts originating from body fluids and/or the hydrogel-forming absorbent polymer, as well as polymeric salts (e.g., extractable polymer) originating from the hydrogel-forming polymer) that tend to be excluded from the swollen hydrogel-forming absorbent polymer and concentrated in voids within the hydrogel zone or layer. Salts concentrated within these voids can depress the swelling of the hydrogel-forming absorbent polymer and thus reduce PUP capacity. Increased porosity can reduce the concentration of these excluded salts and thus increase PUP capacity.

The porosity of the hydrogel zone or layer is also important because of its impact on permeability (i.e., SFC values) of the hydrogel zone/layer. Higher porosity is an important contributor to higher permeability. Conversely, a hydrogel zone or layer with a relatively low porosity is less likely to have very high permeability.

The porosity of the hydrogel zone or layer can also be important as a result of its impact on wicking properties. The high specific surface area required for a hydrogel layer or zone capable of good wicking properties (e.g., wicking fluid to a high height, partitioning fluid away from a cofacial acquisition layer, etc.) is desirably accompanied by a high porosity so as to attain or maintain an acceptably fast wicking rate.

The porosity of the hydrogel zone or layer can also be important as a result of its impact on swelling-rate properties. The high surface area (e.g., internal surface area) required for an unconstrained hydrogel-forming absorbent polymer to swell rapidly in body fluids is desirably accompanied by a high porosity (including internal porosity for hydrogel-forming polymers having internal surface area) in the hydrogel zone or layer formed therefrom under a confining pressure. Desirably as a result of this higher porosity, the swelling rate realized under a confining pressure for the hydrogel-forming polymer within the hydrogel layer approaches the swelling rate realized for the hydrogel-forming absorbent polymer when it swells unconstrained in an excess of body fluid.

Hydrogel-forming absorbent polymers useful in the present invention have PHL values of at least about 0.15, preferably at least about 0.18, more preferably at least about 0.20 and most preferably at least about 0.25. Typically, these PHL values are in the range of from about 0.15 to about 0.40, and more typically from about 0.18 to 0.25. A method for determining the PHL value of these hydrogel-forming absorbent polymers is provided hereafter in the Test Method Section.

(2). Performance Under Pressure (PUP)

Another important characteristic of the hydrogel-forming absorbent polymers useful in the present invention is their demand absorbency capacity under a high confining pressure. This demand-absorbency capacity is defined in terms of the polymer's Performance Under Pressure (PUP) capacity. PUP capacity measures the ability of a high basis weight zone or layer of the hydrogel-forming absorbent polymer to absorb body fluids under usage pressures. When a hydrogel-forming absorbent polymer is incorporated into an absorbent member at high concentrations, the polymer needs to be capable of absorbing large quantities of body fluids in a reasonable time period under usage pressures. Otherwise, the absorbent member will be less effective at absorbing fluid, e.g., by partitioning fluid from acquisition components that provide temporary holding capacity for this fluid. When this occurs, it is believed that the absorbent core is left with insufficient temporary holding capacity to contain subsequent gushes of body fluid and can leak prematurely. Also, to be able to deliver a high storage capacity from an absorbent core of minimal weight and thickness, the hydrogel-forming absorbent polymer needs to have a relatively high PUP capacity. A relatively high PUP capacity hydrogel-forming polymer is also needed to provide economical absorbent cores.

Usage pressures exerted on the hydrogel-forming absorbent polymer include both mechanical pressures (e.g., exerted by the weight and motions of the user, taping forces, etc.) and capillary pressures (e.g., resulting from the acquisition component(s) in the absorbent core that temporarily hold fluid before it is absorbed by the hydrogel-forming absorbent polymer.) It is believed that a total pressure of about 0.7 psi (5 kPa) is reflective of the sum of these pressures on the hydrogel-forming absorbent polymer as it absorbs body fluids under usage conditions.

The PUP capacity of hydrogel-forming absorbent polymers useful in the present invention is generally at least about 23 g/g, preferably at least about 25 g/g, and most preferably at least about 29 g/g. Typically, these PUP capacity values are in the range of from about 23 to about 35 g/g, more typically from about 25 to about 33 g/g, and most typically from about 29 to about 33 g/g. A method for determining the PUP capacity value of these hydrogel-forming absorbent polymers is provided hereafter in the Test Method Section.

(3). Saline Flow Conductivity (SFC)

Another important characteristic of the hydrogel-forming absorbent polymers useful in the present invention is their permeability or flow conductivity when swollen with body fluids so as to form a hydrogel zone or layer. This permeability or flow conductivity is defined herein in terms of the Saline Flow Conductivity (SFC) value of the hydrogel-forming absorbent polymer. SFC measures the ability of the formed hydrogel zone or layer to transport or distribute body fluids under usage pressures. It is believed that when a hydrogel-forming absorbent polymer is present at high concentrations in an absorbent member and then swells to form a hydrogel under usage pressures, its permeability or flow conductivity properties are generally reflective of the permeability or flow conductivity properties of a hydrogel zone or layer formed from the hydrogel-forming absorbent polymer alone. It is further believed that increasing the permeability of swollen high-concentration regions to levels that approach or even exceed conventional acquisition/distribution materials, such as wood-pulp fluff, can provide superior fluid handling properties for the absorbent member and absorbent core, thus decreasing incidents of leakage, especially at high fluid loadings. (Higher SFC values also are reflective of the ability of the formed hydrogel to acquire body fluids under normal usage conditions.)

The SFC value of the hydrogel-forming absorbent polymers useful in the present invention is at least about $30 \times 10^{-7}$ $cm^3$ sec/g, preferably at least about $50 \times 10^{-7}$ $cm^3$ sec/g, and most preferably at least about $100 \times 10^{-7}$ $cm^3$ sec/g. Typically, these SFC values are in the range of from about 30 to about $1000 \times 10^{-7}$ $cm^3$ sec/g, more typically from about 50 to about $500 \times 10^{-7}$ $cm^3$ sec/g, and most typically from about 100 to about $350 \times 10^{-7}$ $cm^3$ sec/g. A method for determining the SFC value of these hydrogel-forming absorbent polymers is provided hereafter in the Test Method Section.

(4). Extractable Polymer

Another important characteristic of hydrogel-forming absorbent polymers useful in the present invention is the level of extractable polymer material present therein. See U.S. Pat. No. 4,654,039 (Brandt et al), issued Mar. 31, 1987 (reissued Apr. 19, 1988 as U.S. Pat. No. Re. 32,649). Many hydrogel-forming absorbent polymers contain significant levels of extractable polymer material. This extractable polymer material can be leached out from the resultant hydrogel by body fluids (e.g., urine) during the time period such body fluids remain in contact with the hydrogel-forming absorbent polymer. It is believed such extracted polymer material can alter both the chemical characteristics (e.g., osmolarity) and physical characteristics (e.g., viscosity) of the body fluid to such an extent that the fluid is more slowly absorbed and more poorly held by the hydrogel. This polymer contaminated fluid is also more poorly transported through the absorbent member. Such a situation can contribute to undesirable and premature leakage of body fluid from the absorbent article. Thus it is desirable to use hydrogel-forming absorbent polymers with lower levels of extractable polymer material.

The importance of not adversely impacting the effective absorption/retention of body fluids by the swollen hydrogel-forming absorbent polymer, or the facile transport of body fluids through regions of the absorbent member containing the swollen polymer, is believed to be particularly true as: (a) the quantity of polymer in the absorbent member is increased; (b) the quantities of other absorbent components (e.g., fibers) are decreased; and/or (c) the localized concentration of polymer in the absorbent member is increased. Thus, for example, it is believed that at higher localized concentrations of hydrogel-forming absorbent polymer in the absorbent member, there is a smaller volume of fluid within the interstitial regions (i.e., outside the hydrogel) to dilute the extractable polymer material, thus tending to increase its concentration in these interstitial regions. This exacerbates the effect of the extractable polymer on the absorbed body fluids within these interstitial regions.

The adverse impact of higher levels of extractable polymer on the absorption/retention of fluid by the hydrogel-forming absorbent polymer and the transport of fluid through the interstitial regions within the resultant hydrogel zone or layer is also discernible in terms of PUP capacity and SFC values. Thus, for example, it is not unusual for hydrogel-forming absorbent polymers having higher levels of extractable polymer material to have a PUP capacity value that decreases over time (e.g., is lower at 225 minutes versus 60 minutes). This decrease in absorption/retention of fluid over time is believed to be, at least in part, a consequence of higher levels of extractable polymer being present to alter the chemical properties of the interstitial fluid. It is also not unusual for a hydrogel-forming absorbent polymer having higher levels of extractable polymer material to have a SFC value that is initially lower and then increases over time to a greater extent than a comparable hydrogel-forming absorbent polymer having a lower level of extractable polymer. A lower initial SFC value for the higher extractable-polymer material is believed to result, at least in part, from a higher initial viscosity for interstitial fluid.

Accordingly, for hydrogel-forming absorbent polymers useful in the present invention, it is preferred that the level of extractable polymer be about 15% or less, more preferably about 10% or less, and most preferably about 7% or less of the total polymer. Methods for determining the levels of extractable polymer in these hydrogel-forming absorbent polymers invention are provided hereafter in the Test Method Section.

(5). Gel Volume

Another characteristic that can be important for hydrogel-forming absorbent polymers useful in the present invention is gel volume. As used herein, the "gel volume" of a hydrogel-forming absorbent polymer is defined as its free-swell absorbent capacity when swollen in an excess of Jayco synthetic urine. It provides a measure of the maximum absorbent capacity of the polymer under conditions of use where the pressures on the polymer are relatively low. Methods for determining the gel volumes of these hydrogel-forming polymers are provided hereafter in the Test Method Section.

It is preferred that the hydrogel-forming absorbent polymers have a relatively high gel volume. This allows the polymer to absorb a greater quantity of body fluids under usage situations where the pressures on the polymer are low. It is preferred that the gel volume of the hydrogel-forming absorbent polymers of the present invention be at least about 20 g/g, more preferably at least about 25 g/g, and most preferably at least about 30 g/g. Typically, these gel volumes are in the range of from about 20 to about 100 g/g, more typically from about 25 to about 80 g/g, and most typically from about 30 to about 70 g/g.

(6). Gel Strength

Another characteristic that can be important for hydrogel-forming absorbent polymers useful in the present invention is gel strength. As used herein, "gel strength" relates to the tendency of the hydrogel formed from the absorbent polymer to deform or "flow" under usage stresses. Gel strength needs to be such that the hydrogel does not deform and fill to an unacceptable degree the void spaces between the hydrogel and the other components in the absorbent member. In general, increasing gel strength will result in an increase in the permeability and porosity of a hydrogel zone or layer formed from the hydrogel-forming absorbent polymer. A method for determining the gel strength of the hydrogel-forming absorbent polymers of the present invention is provided hereafter in the Test Method Section.

Although maximizing gel strength is not as critical as other properties such as PHL, PUP capacity and SFC, it is preferred that the hydrogel-forming absorbent polymers of the present invention have a relatively high gel strength. This increases the ability of the formed hydrogel to resist deformation under usage pressures. It is preferred that the gel strength of the hydrogel-forming absorbent polymers of the present invention be at least about 10,000 dynes/cm$^2$, more preferably at least about 20,000 dynes/cm$^2$, and most preferably at least about 40,000 dynes/cm$^2$.

c. Methods for Making

The basic hydrogel-forming absorbent polymer can be formed in any conventional manner. Typical and preferred processes for producing these polymers are described in U.S. Re. Pat. No. 32,649 (Brandt et al), issued Apr. 19, 1988, U.S. Pat. No. 4,666,983 (Tsubakimoto et al), issued May 19, 1987, and U.S. Pat. No. 4,625,001 (Tsubakimoto et al), issued Nov. 25, 1986, all of which are incorporated by reference.

Preferred methods for forming the basic hydrogel-forming absorbent polymer are those involving aqueous solution or other solution polymerization methods. As described in the above-referenced U.S. Re. Pat. No. 32,649, aqueous solution polymerization involves the use of an aqueous reaction mixture to carry out polymerization. The aqueous reaction mixture is then subjected to polymerization conditions which are sufficient to produce in the mixture, substantially water-insoluble, slightly network crosslinked polymer. The mass of polymer formed can then be pulverized or chopped to form individual particles.

More specifically, the aqueous solution polymerization method for producing the hydrogel-forming absorbent polymer comprises the preparation of an aqueous reaction mixture in which to carry out the polymerization. One element of such a reaction mixture is the acid group-containing monomer that will form the "backbone" of the hydrogel-forming absorbent polymer to be produced. The reaction mixture will generally comprise about 100 parts by weight of the monomer. Another component of the aqueous reaction mixture comprises a network crosslinking agent. Network crosslinking agents useful in forming the hydrogel-forming absorbent polymer according to the present invention are described in more detail in the above-referenced U.S. Re. Pat. No. 32,649, U.S. Pat. Nos. 4,666,983, and 4,625,001. The network crosslinking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer). An optional component of the aqueous reaction mixture comprises a free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomers, including esters of the essential unsaturated acidic functional group-containing monomers or other co-monomers containing no carboxylic or sulfonic acid functionalities at all.

The aqueous reaction mixture is subjected to polymerization conditions which are sufficient to produce in the mixture substantially water-insoluble, but water-swellable, hydrogel-forming absorbent slightly network crosslinked polymers. The polymerization conditions are also discussed in more detail in the three above-referenced patents. Such polymerization conditions generally involve heating (thermal activation techniques) to a polymerization temperature from about 0° to about 100° C., more preferably from about 5° to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques.

The acid functional groups of the hydrogel-forming absorbent polymer formed in the aqueous reaction mixture are also preferably neutralized. Neutralization can be carried out in any conventional manner that results in at least about 25 mole percent, and more preferably at least about 50 mole percent, of the total monomer utilized to form the polymer being acid group-containing monomers that are neutralized with a salt-forming cation. Such salt-forming cations include, for example, alkali metals, ammonium, substituted ammonium and amines as discussed in further detail in the above-references U.S. Re. Pat. No. 32,649.

While it is preferred that the particulate versions of hydrogel-forming absorbent polymer be manufactured using an aqueous solution polymerization process, it is also possible to carry out the polymerization process using multiphase polymerization processing techniques such as inverse emulsion polymerization or inverse suspension polymerization procedures. In the inverse emulsion polymerization or inverse suspension polymerization procedures, the aqueous reaction mixture as described before is suspended in the form of tiny droplets in a matrix of a water-immiscible, inert organic solvent such as cyclohexane. The resultant particles of hydrogel-forming absorbent polymer are generally spherical in shape. Inverse suspension polymerization procedures are described in greater detail in U.S. Pat. No. 4,340,706 (Obaysashi et al), issued Jul. 20, 1982, U.S. Pat. No. 4,506,052 (Flesher et al), issued Mar. 19, 1985, and U.S. Pat. No. 4,735,987 (Morita et al), issued Apr. 5, 1988, all of which are incorporated by reference.

Surface crosslinking of the initially formed polymers is a preferred process for obtaining hydrogel-forming absorbent polymers having relatively high PHL, PUP capacity and SFC values. Hydrogel-forming absorbent polymers that are surface crosslinked in general have higher values for PHL, PUP capacity and SFC than those having a comparable level of "functional" crosslinks but without surface crosslinking. Without being bound by theory, it is believed that surface crosslinking increases the resistance to deformation of hydrogel-forming absorbent polymer surfaces, thus reducing the degree of contact between neighboring polymer surfaces when the resultant hydrogel is deformed under an external pressure. The degree to which PHL, PUP capacity and SFC values are enhanced by surface crosslinking depends on the relative levels and distributions of internal and surface crosslinks and the specifics of the surface crosslinking chemistry and process.

Functional crosslinks are those that are elastically active and contribute to an increase in modulus for the swollen hydrogel-forming absorbent polymers. Gel volume generally provides a reasonable measure of the overall level of "functional" crosslinking in an hydrogel-forming absorbent polymer, assuming that the only significant variable is the level of crosslinking. Generally, gel volume has an inverse power-law dependence on the level of crosslinking. Additional means for determining the overall levels of functional crosslinks include measurements of shear and elastic modulus of the resultant hydrogel formed by the swollen polymer.

Surface crosslinked hydrogel-forming absorbent polymers have a higher level of crosslinking in the vicinity of the surface than in the interior. As used herein, "surface" describes the outer-facing boundaries of the particle, fiber, etc. For porous hydrogel-forming absorbent polymers (e.g., porous particles, etc.), exposed internal boundaries can also be included. By a higher level of crosslinking at the surface, it is meant that the level of functional crosslinks for the hydrogel-forming absorbent polymer in the vicinity of the surface is generally higher than the level of functional crosslinks for the polymer in the interior.

The gradation in crosslinking from surface to interior can vary, both in depth and profile. Thus, for example, the depth of surface crosslinking can be shallow, with a relatively sharp transition to a lower level of crosslinking. Alternatively, for example, the depth of surface crosslinking can be a significant fraction of the dimensions of the hydrogel-forming absorbent polymer, with a broader transition.

Depending on size, shape, porosity as well as functional considerations, the degree and gradient of surface crosslinking can vary within a given hydrogel-forming absorbent polymer. For particulate hydrogel-forming absorbent polymers, surface crosslinking can vary with particle size, porosity, etc. Depending on variations in surface:volume ratio within the hydrogel-forming absorbent polymer (e.g., between small and large particles), it is not unusual for the overall level of crosslinking to vary within the material (e.g., be greater for smaller particles).

Surface crosslinking is generally accomplished after the final boundaries of the hydrogel-forming absorbent polymer are essentially established (e.g., by grinding, extruding, foaming, etc.) However, it is also possible to effect surface crosslinking concurrent with the creation of final boundaries. Furthermore, some additional changes in boundaries can occur even after surface crosslinks are introduced.

A number of processes for introducing surface crosslinks are disclosed in the art. These include those where: (i) a di- or poly-functional reagent(s) (e.g., glycerol, 1,3-dioxolan-2-one, polyvalent metal ions, polyquaternary amines) capable of reacting with existing functional groups within the hydrogel-forming absorbent polymer is applied to the surface of the hydrogel-forming absorbent polymer; (ii) a di- or poly-functional reagent that is capable of reacting with other added reagents and possibly existing functional groups within the hydrogel-forming absorbent polymer such as to increase the level of crosslinking at the surface is applied to the surface (e.g., the addition of monomer plus crosslinker and the initiation of a second polymerization reaction); (iii) no additional polyfunctional reagents are added, but additional reaction(s) is induced amongst existing components within the hydrogel,forming absorbent polymer either during or after the primary polymerization process such as to generate a higher level of crosslinking at or near the surface (e.g., heating to induce the formation of anhydride and or esters crosslinks between existing polymer carboxylic acid and/or hydroxyl groups and suspension polymerization processes wherein the crosslinker is inherently present at higher levels near the surface); and (iv) other materials are added to the surface such as to induce a higher level of crosslinking or otherwise reduce the surface deformability of the resultant hydrogel. Combinations of these surface crosslinking processes either concurrently or in sequence can also be employed. In addition to crosslinking reagents, other components can be added to the surface to aid/control the distribution of crosslinking (e.g., the spreading and penetration of the surface crosslinking reagents.)

Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et. al.), issued Nov. 17, 1992; published German patent application 4,020,780 (Dahmen), published Aug. 29, 1991; and published European patent application 509,708 (Gartner), published Oct. 21, 1992; all of which are incorporated by reference.

The hydrogel-forming absorbent polymer particles prepared according to the present invention are typically substantially dry. The term "substantially dry" is used herein to mean that the particles have a fluid content, typically water or other solution content, less than about 50%, preferably less than about 20%, more preferably less than about 10%, by weight of the particles. In general, the fluid content of the hydrogel-forming absorbent polymer particles is in the range of from about 0.01% to about 5% by weight of the particles. The individual particles can be dried by any conventional method such as by heating. Alternatively, when the particles are formed using an aqueous reaction mixture, water can be removed from the reaction mixture by azeotropic distillation. The polymer-containing aqueous reaction mixture can also be treated with a dewatering solvent such as methanol. Combinations of these drying procedures can also be used. The dewatered mass of polymer can then be chopped or pulverized to form substantially dry particles of the hydrogel-forming absorbent polymer.

d. Specific Examples

The following provides some specific examples of hydrogel-forming absorbent polymers suitable for use in the present invention:

Example 1: Surface Treatment of Nalco 1180 with Ethylene Carbonate

A non-surface-crosslinked particulate partially neutralized sodium polyacrylate hydrogel-forming polymer, obtained from Nalco Chemical Co., Naperville Ill. (Nalco 1180; lot no. NCGLG3C920E), is used and has the properties listed under Sample 1-1 in Table 1 below. A 20.0 gram aliquot of this hydrogel-forming absorbent polymer is divided equally into two pre-weighed 150×15 mm disposable polystyrene petri dishes. The polymer in each of the petri dishes is spread out over the bottom, so that the particles are generally not piled on top of each other. A Prevail Spray Gun (Precision Valve Corp; Yonkers, N.Y.) is used to deposit 2.0 g of a 50 weight percent aqueous solution of ethylene carbonate (1,3-dioxolan-2-one; Aldrich cat. no. E2,625-8) on the particles. This corresponds to a 10% weight add-on to the starting polymer. Approximately one-half of the total application is sprayed over exposed surfaces of the particles in the two petri dishes. This causes the particles to generally adhere in a sheet-like structure. The petri dishes are covered, inverted, and tapped so that, for each petri dish, the sheet-like structure is transferred to the inverted cover of the petri dish and the bottom surfaces of the particles are exposed. Particles adhering to the bottom of the petri dish are scrapped off and transferred to the inverted cover. The second half of the application is then applied. The inverted cover of the petri dish is then covered by the inverted bottom of the petri dish. The entire system (petri dish bottom, petri dish cover, hydrogel-forming polymer, & applied ethylene carbonate solution) is weighed. The total weight of ethylene carbonate solution deposited in both petri dishes is determined gravimetrically, by difference from the combined weight prior to spraying.

The treated hydrogel-forming absorbent polymer is transferred to a Number 20 U.S.A Standard Testing Sieve (850 micron opening). The sheet-like structure is gently disrupted with gentle pressure using a spatula and plastic scoop so that the bulk of the polymer passes through the screen and is collected in a pan. Some physical losses occur during this process. The particulate polymer is transferred to a tared glass beaker and covered with a watch glass. The sample is then placed into a pre-heated Despatch LFD Forced Air Oven that is preset at a temperature of 195° C. It is removed after one hour, placed in a desiccating box over Drierite, and reweighed after cooling to ambient temperature. The percent weight loss as a result of heating is 12.2%.

The resultant surface-treated polymer particles tend to adhere to each other. The particulate mass is gently disrupted with a spatula and transferred back to the No 20 sieve. The bulk of the particles passes through the sieve upon gentle agitation and pressure and are collected in the pan. Some slight additional physical losses occur during this process. The surface-treated polymer particles are then transferred to a tared bottle for weighing and storage. A product weight of 17.4 grams is obtained.

The properties of these surface-treated polymer particles (sample 1-2) are shown in Table 1 below:

through U.S.A. Standard Testing Sieves. The properties of these fractionated samples are shown in Table 3 below:

TABLE 1

| Sample Code | Mass Median (microns) | Gel Volume (g/g) | Extractables (weight %) | PUP Capacity (g/g) | SFC Value[1] ($10^{-7} \times cm^3 sec/g$) | PHL Value |
|---|---|---|---|---|---|---|
| 1-1[2] | 400 | 42.2 | 9 | 8.6 | 0.073[3] | <0.07[4] |
| 1-2 | 450 | 35.6 | 7 | 29.3 | 113 | 0.17[5] |

[1]Average of three determinations
[2]Base polymer for preparation of sample 1-2 (prior to surface crosslinking)
[3]The absorption time for Jayco synthetic urine is extended to 16 hours for this sample
[4]Estimated
[5]Average of three determinations with standard deviation of 0.002.

Example 2: Hydrogel-Forming Absorbent Polymers From Commercial Sources

The properties of certain particulate partially-neutralized sodium polyacrylate hydrogel-forming polymers obtained from commercial sources useful in the present invention are shown in Tables 2-1 and Table 2-2:

TABLE 2-1

| Sample Code | Manufacturer | Sample Designation | Lot # |
|---|---|---|---|
| 2-1 | Stockhausen[1] | W52521 | |
| 2-2 | " | W52521[4] | |
| 2-3 | " | W52523 | |
| 2-4 | Nalco Chemical Co[2] | XP-30 | 3707-90A |
| 2-5 | " | XP-30 | 3815-64 |
| 2-6 | Chemdal Corp.[3] | ASAP-1001 | 3373 |
| 2-7 | " | " | 00842 |

[1]Stockhausen, Chemische Fabrik Stockhausen GmbH of Krefeld, Germany
[2]Nalco Chemical Company of Naperville, Illinois
[3]Chemdal Corporation of Palatine, Illinois
[4]A second lot of Stockhausen W52521

TABLE 2-2

| Sample Code | Mass Median (microns) | Gel Volume (g/g) | Extractables (weight %) | PUP Capacity (g/g) | SFC Value[1] ($10^{-7} \times cm^3 sec/g$) | PHL Value |
|---|---|---|---|---|---|---|
| 2-1 | 430 | 29.1 | 5 | 25.9 | 165 | 0.17 |
| 2-2 | 520 | 31.2 | 6 | 25.9 | 131 | 0.20 |
| 2-3 | 360 | 35.7 | 5 | 29.9 | 60 | 0.15 |
| 2-4 | 360 | 34.7 | 4 | 29.9 | 49 | 0.18 |
| 2-5 | 390 | 35.2 | 4 | 30.9 | 57 | 0.18 |
| 2-6 | 500 | 35.4 | 15 | 23.6 | 88 | 0.16 |
| 2-7 | 440 | 37.2 | 13 | 23.4 | 68 | 0.16 |

[1]Average of three determinations
[2]PHL value for sample 2-5 is the average of three determinations; PHL values for other samples are average of two determinations.

Example 3: Selected Size Fractions of Hydrogel-Forming Polymers

Selected size fractions of particulate partially neutralized sodium polyacrylate hydrogel-forming absorbent polymers are obtained by size fractionation of the bulk polymers

TABLE 3

| Sample Code | Sample Source | Size Fraction (microns) | Gel Volume (g/g) | Extractables (weight %) | PUP Capacity (g/g) | SFC Value[1] ($10^{-7} \times cm^3 sec/g$) | PHL[2] Value |
|---|---|---|---|---|---|---|---|
| 3-1 | 2-1 | 500–710 | 28.2 | 4 | 25.7 | 350 | 0.19 |
| 3-2 | " | 355–500 | 29.2 | 6 | 26.4 | 248 | 0.20 |
| 3-3 | " | 250–355 | 30.3 | 6 | 26.9 | 166 | 0.20 |

[1] Average of three determinations
[2] Average of two determinations

2. Fibrous Materials

The absorbent members of the present invention can comprise fibrous materials to form fibrous web or fibrous matrices. Fibers useful in the present invention include those that are naturally occurring fibers (modified or unmodified), as well as synthetically made fibers. Examples of suitable unmodified/modified naturally occurring fibers include cotton, Esparto grass, bagasse, kemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The fibers used can comprise solely naturally occurring fibers, solely synthetic fibers, or any compatible combination of naturally occurring and synthetic fibers.

The fibers used in the present invention can be hydrophilic, hydrophobic or can be a combination of both hydrophilic and hydrophobic fibers. As used herein, the term "hydrophilic" describes fibers, or surfaces of fibers, that are wettable by aqueous fluids (e.g., aqueous body fluids) deposited on these fibers. Hydrophilicity and wettability are typically defined in terms of contact angle and the surface tension of the fluids and solids involved. This is discussed in detail in the American Chemical Society publication entitled Contact Angle, Wettability and Adhesion, edited by Robert F. Gould (Copyright 1964). A fiber, or surface of a fiber, is said to be wetted by a fluid (i.e., hydrophilic) when either the contact angle between the fluid and the fiber, or its surface, is less than 90°, or when the fluid tends to spread spontaneously across the surface of the fiber, both conditions normally co-existing. Conversely, a fiber or surface is considered to be hydrophobic if the contact angle is greater than 90° and the fluid does not spread spontaneously across the surface of the fiber.

The particular selection of hydrophilic or hydrophobic fibers will depend upon the fluid handling properties and other characteristics desired for the resulting absorbent member. For example, for absorbent members that are to be used to replace completely, or partially, a hydrophobic, nonwoven topsheet, at least one of the absorbent members, typically the member adjacent the wearer of the absorbent article, can desirably comprise hydrophobic fibers. The use of hydrophobic fibers in at least one of the absorbent members can also be useful where the member comprising the hydrophobic fibers is adjacent a "breathable," but somewhat fluid previous backsheet of an absorbent article such as infant training pants; the member comprising the hydrophobic fibers provides a fluid impervious barrier.

For many absorbent members according to the present invention, the use of hydrophilic fibers is preferred. This is especially true for absorbent members that are desired to efficiently acquire discharged body fluids, and then quickly transfer and distribute the acquired fluid to other, remote regions of the absorbent member or absorbent core. The use of hydrophilic fibers is particularly desirable for those absorbent members that comprise the hydrogel-forming absorbent polymers.

Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene,-polyacrylics, polyamides, polystyrenes, polyurethanes and the like. For reasons of availability and cost, cellulosic fibers, in particular wood pulp fibers, are preferred for use in the present invention.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemimechanical, and chemithermomechanical pulp processes. Recycled or secondary wood pulp fibers, as well as bleached and unbleached wood pulp fibers, can be used.

A desirable source of hydrophilic fibers for use in the present invention, especially for absorbent members providing both fluid acquisition and distribution properties, is chemically stiffened eellulosic fibers. As used herein, the term "chemically stiffened cellulosic fibers" means cellulosic fibers that have been stiffened by chemical means to increase the stiffness of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Polymeric stiffening agents that can coat or impregnate the cellulosic fibers include: cationic modified starches having nitrogen-containing groups (e.g., amino groups) such as those available from National Starch and Chemical Corp., Bridgewater, N.J., U.S.A.; latexes; wet strength resins such as polyamide-epichlorohydrin resin (e.g., Kymene® 557H, Hercules, Inc. Wilmington, Del., U.S.A.), polyacrylamide resins described, for example, in U.S. Pat. No. 3,556,932 (Coscia et al) issued Jan. 19, 1971; commercially available polyacrylamides marketed by American Cyanamid Co., Stamford, Conn., U.S.A., under the tradename Parez® 631 NC; urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

These fibers can also be stiffened by chemical reaction. For example, crosslinking agents can be applied to the fibers that, subsequent to application, are caused to chemically form intrafiber crosslink bonds. These crosslink bonds can increase the stiffness of the fibers. While the utilization of intrafiber crosslink bonds to chemically stiffen the fiber is preferred, it is not meant to exclude other types of reactions for chemical stiffening of the fibers.

Fibers stiffened by crosslink bonds in individualized form (i.e., the individualized stiffened fibers, as well as processes for their preparation) are disclosed, for example, in U.S. Pat. No. 3,224,926 (Bernardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al.), issued Jul. 12, 1977. More preferred stiffened fibers are disclosed in U.S. Pat. No. 4,822,453 (Dean et al), issued Apr. 18, 1989; U.S. Pat. No. 4,888,093 (Dean et al), issued Dec. 19, 1989; U.S. Pat. No. 4,898,642 (Moore et al), issued Feb. 6, 1990; and U.S. Pat. No. 5,137,537 (Herrow et al), issued Aug. 11, 1992, all of which are incorporated by reference.

In the more preferred stiffened fibers, chemical processing includes intrafiber crosslinking with crosslinking agents while such fibers are in a relatively dehydrated, defibrated (i.e., individualized), twisted, cured condition. Suitable chemical stiffening agents are typically monomeric crosslinking agents including, but not limited to, $C_2$–$C_8$ dialdehyde, $C_2$–$C_8$ monoaldehydes having an acid functionality, and especially $C_2$–$C_9$ polycarboxylic acids. These compounds are capable of reacting with at least two hydroxyl groups in a single cellulose chain or on proximately located cellulose chains in a single fiber. Specific examples of such crosslinking agents include, but are not limited to, glutaraldehyde, glyoxal, formaldehyde, glyoxylic acid, oxydisuccinic acid and citric acid. The effect of crosslinking under these conditions is to form fibers that are stiffened and which tend to retain their twisted, curled configuration during use in the thermally bonded absorbent structures herein. Such fibers, and processes for making them, are described in the above incorporated patents.

The preferred stiffened fibers that are twisted and curled can be quantified by referencing both a fiber "twist count" and a fiber "curl factor". As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°. The number of twist nodes in a certain length of fibers (i.e., the twist count) is directly indicative of the degree of fiber twist, which is a physical parameter of the fiber. The procedures for determining twist nodes and total twist count are described in U.S. Pat. No. 4,898,642.

The preferred stiffened fibers will have an average dry fiber twist count of at least about 2.7, preferably at least about 4.5 twist, nodes per millimeter. Furthermore, the average wet fiber twist count of these fibers should preferably be at least about 1.8, preferably at least about 3.0, and should also preferably be at least about 0.5 twist nodes per millimeter less than the average dry fiber twist count. Even more preferably, the average dry fiber twist count should be at least about 5.5 twist nodes per millimeter, and the average wet fiber twist count should be at least about 4.0 twist nodes per millimeter and should also be at least 1.0 twist nodes per millimeter less than its average dry fiber twist count. Most preferably, the average dry fiber twist count should be at least about 6.5 twist nodes per millimeter, and the average wet fiber twist count should be at least about 5.0 twist nodes per millimeter and should also be at least 1.0 twist nodes per millimeter less than the average dry fiber twist count.

In addition to being twisted, these preferred stiffened fibers are also cuffed. Fiber cuff can be described as the fractional shortening of the fiber due to kinks, twists, and/or bends in the fiber. For the purposes of the present invention, fiber cuff is measured in terms of a two dimensional plane. The extent of fiber cuffing can be quantified by referencing a fiber cud factor. The fiber curl factor, a two dimensional measurement of curl, is determined by viewing the fiber in a two dimensional plane. To determine curl factor, the projected length of the fiber as the longest dimension of a two dimensional rectangle encompassing the fiber, LR, and the actual length of the fiber, $L_A$, are both measured. The fiber curl factor can then be calculated from the following equation:

$$\text{Curl Factor} = (L_A/L_R) - 1.$$

An image analysis method that can be utilized to measure $L_R$ and $L_A$ is described in U.S. Pat. No. 4,898,642. Preferably the stiffened fibers will have a curl factor of at least about 0.30, and more preferably will have a curl factor of at least about 0.50.

These chemically stiffened cellulosic fibers have certain properties that make them particularly useful in certain absorbent members according to the present invention, relative to unstiffened cellulosic fibers. In addition to being hydrophilic, these stiffened fibers have unique combinations of stiffness and resiliency. This allows thermally bonded absorbent structures made with these fibers to maintain high levels of absorptivity, and to exhibit high levels of resiliency and an expansionary responsiveness to wetting. In particular, the resiliency of these stiffened fibers enables the absorbent member to better maintain its capillary structure in the presence of both fluid and compressive forces normally encountered during use and are thus more resistant to collapse.

3. Thermoplastic Materials

In the case of thermally bonded absorbent members according to the present invention, the member can comprise thermoplastic material in addition to the fibers. Upon melting, at least a portion of this thermoplastic material migrates to the intersections of the fibers, typically due to interfiber capillary gradients. These intersections become bond sites for the thermoplastic material. When cooled, the thermoplastic materials at these intersections solidify to form the bond sites that hold the matrix or web of fibers together in each of the respective layers.

Amongst its various effects, bonding at these fiber intersections increases the overall compressive modulus and strength of the resulting thermally bonded member. In the case of the chemically stiffened cellulosic fibers, the melting and migration of the thermoplastic material also has the effect of increasing the average pore size of the resultant web, while maintaining the density and basis weight of the web as originally formed. This can improve the fluid acquisition properties of the thermally bonded member upon initial discharges, due to improved fluid permeability, and upon subsequent discharges, due to the combined ability of the stiffened fibers to retain their stiffness upon wetting and the ability of the thermoplastic material to remain bonded at the fiber intersections upon wetting and upon wet compression. In net, thermally bonded webs of stiffened fibers retain their original overall volume, but with the volumetric regions previously occupied by the thermoplastic material becoming open to thus increase the average interfiber capillary pore size.

Thermoplastic materials useful in the present invention can be in any of a variety of forms including particulates, fibers, or combinations of particulates and fibers. Thermoplastic fibers are a particularly preferred form because of their ability to form numerous interfiber bond sites. Suitable thermoplastic materials can be made from any thermoplastic polymer that can be melted at temperatures that will not extensively damage the fibers that comprise the primary web or matrix of each layer. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. One preferred thermoplastic binder fiber is PLEXAFIL® polyethylene microfibers (made by DuPont) that are also available as an about 20% blend with 80% cellulosic fibers sold under the tradename KITTYHAWK® (made by Weyerhaeuser Co.) Depending upon the desired characteristics for the resulting thermally bonded absorbent member, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These suffactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

In the case of thermoplastic fibers, their length can vary depending upon the particular melt point and other properties desired for these fibers. Typically, these thermoplastic fibers have a length from about 0.3 to about 7.5 cm long, preferably from about 0.4 to about 3.0 cm long, and most preferably from about 0.6 to about 1.2 cm long. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers can have a decitex in the range from about 1.0 to about 20, preferably from about 1.4 to about 10, and most preferably from about 1.7 to about 3.3.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective absorbent members during preparation of the absorbent core.

4. Other Components and Materials

Absorbent members according to the present invention can include other optional components that can be present in absorbent webs. For example, a reinforcing scrim can be positioned within the absorbent member, or between the respective absorbent members, of the absorbent core. Such reinforcing scrims should be of such configuration as to not form interfacial barriers to fluid transfer, especially if positioned between the respective absorbent members of the absorbent core. Also, when hydrogel-forming absorbent polymers are present in one or more absorbent members of the absorbent core, the respective absorbent member, or the entire absorbent core, can be enveloped within a fluid previous sheet, such as a tissue paper sheet, to obviate user concern regarding loose particulate absorbent polymer. Other optional components that can be included are materials to control odor, adhesives, contain fecal matter, etc.

Absorbent members according to the present invention can also include foam-based absorbents. Suitable foam absorbents include those described in U.S. Pat. No. 5,260,345 (DesMarais et al), issued Nov. 9, 1993 and U.S. Pat. No. 5,147,345 (Young et al), issued Sep. 15, 1992, both of which are incorporated by reference.

C. Absorbent Members Containing Hydrogel-Forming Absorbent Polymers

1. Concentration, Basis Weight and Fluid Handling Properties

At least one of the absorbent members according to the present invention will comprise the previously described hydrogel-forming absorbent polymers, with or without other optional components such as fibers, thermoplastic material, etc. These absorbent members comprising these absorbent polymers can function as fluid storage members in the absorbent core. The principle function of such fluid storage members is to absorb the discharged body fluid either directly or from other absorbent members (e.g., fluid acquisition/distribution members), and then retain such fluid, even when subjected to pressures normally encountered as a result of the wearer's movements. It should be understood, however, that such polymer-containing absorbent members can serve functions other than fluid storage.

An important aspect of these absorbent members according to the present invention is that they contain one or more regions having a high concentration of these hydrogel-forming absorbent polymers. In order to provide relatively thin absorbent articles capable of absorbing and retaining large quantities of body fluids, it is desirable to increase the level of these hydrogel-forming absorbent polymers and to reduce the level of other components, in particular fibrous components. In order to utilize these hydrogel-forming absorbent polymers at relatively high concentrations, however, it is important that these polymers have a relatively high porosity (i.e., PHL value) as well as a relatively high demand absorbency capacity under a relatively high confining pressure (i.e., PUP capacity value) and preferably a relatively high permeability under pressure (i.e., SFC value). This is so that the polymer, when swollen in the presence of body fluids, provides adequate capability to acquire these discharged body fluids and then transport these fluids through the gel-continuous fluid transportation zone or layer to other regions of the absorbent member and/or absorbent core and/or then to store these body fluids.

In measuring the concentration of hydrogel-forming absorbent polymer in a given region of an absorbent member, the percent by weight of the hydrogel-forming polymer relative to the combined weight of hydrogel-forming polymer and any other components (e.g., fibers, thermoplastic material, etc.) that are present in the region containing the polymer is used. With this in mind, the concentration of the hydrogel-forming absorbent polymers in a given region of an absorbent member according to the present invention can be in the range of from about 60 to 100%, preferably from about 70 to 100%, more preferably from about 80 to 100%, and most preferably from about 90% to 100%.

Another important aspect is the basis weight of the hydrogel-forming absorbent polymer in a given region of the absorbent member. The hydrogel layer porosity, gel permeability and high demand absorbent capacity properties of this hydrogel-forming absorbent polymer become most impactful on the absorbency performance of the absorbent member and the absorbent core at certain minimum basis weights of the polymer. In measuring the basis weight of the hydrogel-forming absorbent polymer in a given region of an absorbent member, the grams of polymer present per square meter (gsm) of area of the region is used. With this in mind, the basis weight of a hydrogel-forming absorbent polymer in a given region of an absorbent member according to the present invention is at least about 10 gsm, preferably at least about 20 gsm, more preferably at least about 50 gsm, and most preferably at least about 100 gsm. Typically, these basis weight values are in the range of from about 10 to about 1000 gsm, more typically from about 50 to about 800 gsm, and most typically from about 100 to about 600 gsm.

When a hydrogel-forming absorbent polymer is incorporated in an absorbent storage member at a sufficiently high concentration and basis weight, the swelling by body fluids under pressure brings the boundaries of the resultant hydrogel within a given region into contact (i.e., the hydrogel in the region becomes contiguous.) Within these expanded/swollen high-concentration regions, the voids and capillaries are generally bounded by the hydrogel, thus forming a gel-continuous fluid transportation zone or layer. For these regions, it is believed the porosity and fluid permeability approaches that of a comparable hydrogel layer formed under pressure from the polymer alone. Moreover, the use of the previously described hydrogel-forming absorbent polymers having relatively high PHL and preferably relatively high SFC values confers a higher porosity and preferably a higher permeability, respectively and thus good fluid acquisition, transport, and storage properties for these gel-continuous fluid transportation zones or layers.

2. Wet Integrity of Absorbent Member and/or Absorbent Core

During initial fluid acquisition, absorbent core utilization occurs in the immediate vicinity of the gush. There are several pathways for utilizing the absorbent core beyond this initial fluid acquisition point. Fluid can move across the topsheet and enter the core over a larger area. This is not a desirable situation since this fluid is in contact with the skin and is vulnerable to leakage from the absorbent article. Certain features of the absorbent article, e.g. barrier leg cuffs, can help with the latter. Also, special fluid acquisition members have been used to move fluid below the topsheet prior to entry into the storage regions of the absorbent core. In spite of these measures to improve fluid handling performance, there is still a need to gain as much lateral (i.e., X-Y dimension) fluid movement as possible in the storage regions of the core, particularly as the absorbent cores become thinner and thinner.

The potential improvements in lateral fluid movement offered by absorbent members comprising the relatively high porosity and preferably high permeability hydrogel-forming absorbent polymers described above requires a certain amount of physical continuity in the hydrogel-containing region (i.e., the gel-continuous fluid transportation zone or layer) for adequate fluid movement to take place through contiguous interstitial voids and capillaries. Realization of the benefits of these high porosity and preferably high permeability hydrogel-forming absorbent polymers is facilitated by absorbent members and absorbent cores designed to reduce or minimize the occurrence of disruptions in the gel-continuous fluid transportation zones or layers that are formed when the polymer is swollen by body fluids. Absorbent members and/or cores that provide such characteristics are referred to herein as having good wet integrity. By "good wet integrity" is meant that the region or regions in the absorbent member having the high concentration of hydrogel-forming absorbent polymer have sufficient integrity in a dry, partially wet, and/or wetted state such that the physical continuity (and thus the capability of acquiring and transporting fluid through contiguous interstitial voids/capillaries) of the gel-continuous fluid transportation zone or layer formed upon swelling of the hydrogel-forming absorbent polymer in the presence of body fluids is not substantially disrupted or altered, even when subjected to normal use conditions.

During normal use, absorbent cores in absorbent articles are typically subjected to tensional and torsional forces of varying intensity and direction. These tensional and torsional forces include bunching in the crotch area, stretching and twisting forces as the person wearing the absorbent article walks, squats, bends, and the like. If wet integrity is inadequate, these tensional and torsional forces can potentially cause a substantial alteration and/or disruption in the physical continuity of the hydrogel such that its capability of transporting fluids through the contiguous voids and capillaries is degraded, e.g., the gel-continuous zone or layer can be partially separated, fully separated, have gaps introduced, have areas that are significantly thinned, and/or broken up into a plurality of significantly smaller segments. Such alteration could reduce or minimize the advantageous porosity and permeability/flow conductivity properties conferred by the above described hydrogel-forming absorbent polymer.

Good wet integrity can be achieved according to the present invention by various designs, configurations, compositions, etc., in the absorbent member having the high concentration of hydrogel-forming absorbent polymer, the other components in the absorbent core (e.g., fluid acquisition members), the other components in the absorbent article (e.g., the topsheet and/or backsheet), or any combination of these components. These include:

a. Modifications to the components in the absorbent member. For example, fibrous components in the absorbent member can be modified physically, chemically or otherwise to increase wet strength. The fibrous components can also be modified to produce interlocking fibers, portions of fibers, or surface irregularities that interlock or otherwise add integrity to the absorbent member. Cf. U.S. Pat. No. 4,935,022 (Lash et al), issued Jun. 19, 1990. Also the hydrogel-forming absorbent polymer itself can be modified, such as in the case of fibrous forms, or by twisting, curling, adjusting the fiber length, or adjusting the surface properties that cause interlocking, or otherwise add integrity to the absorbent member. Cf. U.S. Pat. No. 4,861,539 (Allen et al), issued Aug. 29, 1989; U.S. Pat. No. 4,997,714 (Farrar et al), issued Mar. 5, 1991; U.S. Pat. No. 4,962,172 (Allen et al), issued Oct. 9, 1990; and U.S. Pat. No. 5,147,956 (Allen et al), issued Sep. 15, 1992.

b. Locating the hydrogel-forming absorbent polymer in particular regions of the absorbent member. For example, the absorbent can have profiled concentrations of polymer so as to provide regions containing little or no polymer and consequently minimize the disruptive impact of polymer swelling upon wet integrity. Cf. U.S. Pat. No. 5,047,023 (Berg), issued Sep. 10, 1991; U.S. application Ser. No. 141,156 (Richards et al), filed Oct. 21, 1993.

c. Adding fibrous components to hydrogel-forming absorbent polymer-containing absorbent member that are not water plasticized. These fibrous components can contribute integrity by entanglement or alternatively, upon suitable heating, can form interfiber bonds, e.g., by thermal bonding, particularly where bicomponent thermoplastic fibers are used. Cf. World (PCT) patent application 91/11162 (Lash), published Aug. 8, 1991; U.S. application Ser. No. 141,156 (Richards et al), filed Oct. 21, 1993. Stabilizing fibers such as polyethylene terephthalate (PET) fibers can also be included in other absorbent members of the absorbent core. Cf. U.S. applications Ser. No. 08/153,739 (Dragoo et al), filed Nov. 16, 1993; and U.S. application Ser. No. 08/164, 049 (Dragoo et al), filed Dec. 8, 1993.

d. The use of adhesive. These include microfiber glues, resins that maintain integrity when wet (e.g., wet strength resins) and hot melt adhesives, e.g., elastic hot melt adhesives. Cf. U.S. applications Ser. No. 08/153, 739 (Dragoo et al), filed Nov. 16, 1993; U.S application Ser. No. 08/164,049 (Dragoo et al), filed Dec. 8, 1993; and U.S Pat. No. 5,387,208 (Ashton et al), issued Feb. 7, 1995.

e. The use of single or multiple sheet-like components or layers that maintain integrity when wet. For example, one or more permeable nonwoven layers and/or high wet strength tissues can be used. These nonwoven layers or tissues can be contiguous or noncontiguous to the hydrogel-forming absorbent polymer-containing absorbent member. They can be attached to one or more components of the polymer-containing absorbent member, or to other members of the absorbent core by thermal bonding or adhesives for additional integrity. Cf. U.S. Pat. No. 4,798,603 (Meyer, et. al), issued Jan. 17, 1989; U.S. applications Ser. No. 08/153,739 (Dragoo et al), filed Nov. 16, 1993; and U.S application Ser. No. 08/164,049 (Dragoo et al), filed Dec. 8, 1993.

f. Attachment of the hydrogel-forming absorbent polymer to one or more sheet-like components or layers or between such components or layers (e.g. lamination). These layers can treated to provide appropriate wet strength. For example, the layers of tissue can be misted with water or otherwise made to absorb small amounts of moisture to tackify the polymer. Upon drying, the laminated absorbent member has adequate dry integrity and stability such that the polymer is not loose and cannot easily be sifted out. Upon wetting, the member exhibits wet integrity due to the wet strength of the tissue layers surrounding the polymer. The absorbent member can also be formed such that the polymer is contained or encapsulated by gluing with a wet stable glue or otherwise bonded in a wet stable manner to the layer or layers of tissue around the periphery of the polymer containing region, thus providing additional dry and wet integrity and preventing migration of polymer outside the envelope so formed. Alternatively, the absorbent member can be formed so that the polymer is further encapsulated or pocketed into specific regions or held in place by wet stable bonds at specific points or areas between the layers of tissue, further improving the dry and wet integrity of the member and further preventing the migration of hydrogel-forming absorbent polymer out of the member. Cf. U.S. Pat. No. 4,935,022 (Lash et al), issued Jun. 19, 1990; U.S. Pat. No. 5,149,335 (Kellenberger et al), issued Sep. 22, 1992.

D. Absorbent Cores

Absorbent members according to the present invention comprising high concentrations of hydrogel-forming absorbent polymers are useful alone or in combination with other absorbent members in a variety of absorbent cores. These other absorbent members can include those useful for initially acquiring the discharged body fluids before these fluids are distributed to the fluid storage member of the absorbent core. These include absorbent members that provide multiple fluid handling properties (e.g., fluid acquisition and distribution) or single fluid handling properties (e.g., fluid distribution). These other absorbent members can also comprise lower concentrations of the hydrogel-forming absorbent polymers that have the physical properties previously specified (e.g. relatively high PHL, PUP capacity and preferably SFC values as described in B(1)(b) above) or can comprise hydrogel-forming absorbent polymers having different physical properties (e.g. lower PHL, PUP capacity and/or SFC values).

One suitable absorbent core according to the present invention comprises: (1) an upper assembly having: (a) an acquisition layer substantially free of hydrogel-forming absorbent polymer; and (b) an absorbent polymer layer mainly comprising a first hydrogel-forming absorbent polymer that has an SFC value of at least about $4 \times 10^{-7}$ cm$^3$ sec/g, preferably at least about $6 \times 10^{-7}$ cm$^3$ sec/g, more preferably at least $9 \times 10^{-7}$ cm$^3$ sec/g and most preferably at least $15 \times 10^{-7}$ cm$^3$ sec/g and which is present in an amount of at least about 20 gsm; and (2) a lower assembly that includes: (a) an upper layer having void space for storage and redistribution of body fluids and (b) a lower layer that contains a high concentration of a second hydrogel-forming absorbent polymer having least the PHL, PUP capacity and preferably SFC values described in B(1)(b) above and wherein at least about 70% of the total amount of the second hydrogel-forming absorbent polymer that is in the upper and lower layers is in the lower half of the combined thickness of the upper and lower layers.

One such absorbent core is shown in FIG. 1. FIG. 1 shows a cross-section of an absorbent article indicated as 10 having a topsheet 12, a backsheet 16 and an absorbent core indicated by 20 positioned between topsheet 12 and backsheet 16. As shown in this Figure, core 20 comprises an upper assembly 24 and a lower assembly 28. Upper assembly 24 comprises an upper acquisition/distribution layer 32, and a layer 40 comprising the first hydrogel-forming absorbent polymer separated from the acquisition layer 32 by a tissue layer 36 having two folds in the Z direction. Lower assembly 28 comprises an upper fibrous layer 44, a lower layer 48 comprising the second hydrogel-forming absorbent polymer, and a tissue layer 52. Layers 32 and 40 can be separate layers as shown in FIG. 1 or can be merged into a single layer and serve as a storage and redistribution assembly. As is apparent from FIG. 1, it is not essential that the layers should be co-extensive.

Acquisition layer 32 of upper assembly 24 is the upper effective layer of the absorbent core and is typically substantially free of hydrogel-forming absorbent polymer. If hydrogel-forming absorbent polymer is included, the amount should be kept relatively low and is preferably substantially free of superabsorbent material, at least in the upper half layer 32, and generally throughout most or all of its thickness. See U.S. Pat. No. 5,217,445 (Young et al), issued Jun. 8, 1993, and U.S. Pat. No. 5,360,420, (Cook et al), issued Nov. 1, 1994, which are incorporated by reference Layer 32 can be of foam or any other suitable porous or capillary material but is usually formed from fibrous material. The fibrous material can be any fibrous material that has a suitable resistance to load when wet, i.e. is able to maintain satisfactory void volume under such conditions. Particularly preferred fibrous materials for layer 32 are chemically stiffened fibers as described in B(2) above, typically in an amount of 50 to 100% by weight of layer 32.

Layer 40 of upper assembly 24 can be integral with the lower part of layer 32 but preferably is a separate layer and can be separated from the layer 32 by a tissue or other component that acts as a containment barrier for the hydrogel-forming absorbent polymer. It is important that layer 40 allow the body fluids acquired by layer 32 to pass rapidly therethrough and be distributed beyond layer 40. The amount of the first hydrogel-forming absorbent polymer in layer 40 should be sufficient to provide a hydrogel layer when swollen by absorption of body fluids in use. This first hydrogel-forming absorbent polymer is usually in particulate form and is usually present in an amount of at least about 20 gsm, more typically in an amount of at least about 50 gsm. Generally layer 40 should not be too thick; normally the amount of hydrogel-forming absorbent polymer is below about 320 gsm and more typically below about 200 gsm.

Lower assembly 28 serves as the storage and redistribution component of core 20 and includes an upper, usually fibrous, layer and a layer of second hydrogel-forming absorbent polymer. The upper layer 44 of lower assembly 28 is generally fibrous but can be formed from foam or other suitable capillary or porous material, and can be formed from the same or different materials as layer 32.

Upper layer 44 can be substantially or completely free of hydrogel-forming absorbent polymer. However it is often desirable for the upper and lower layers 44 and 48 to be formed to provide a fibrous matrix wherein more than half, and usually at least about 70%, of the hydrogel-forming absorbent polymer in these layers is in the lower half thereof. For example, from about 70 to 100%, more typically from about 75 to about 90% of the second hydrogel-forming absorbent polymer is in the lower 50% of combined layers 44 and 48. There can be some, for example, up to about 30%, of the second hydrogel-forming absorbent polymer in the upper half of combined layers 44 and 48.

The first hydrogel-forming absorbent polymer, and sometimes also the second hydrogel-forming absorbent polymer, is provided as a layer that comprises predominantly the absorbent polymer. By "predominantly is meant that at least about 50%, and more typically at least about 70 or about 80% of layers 40 or 48 are hydrogel-forming absorbent polymer. These layers of hydrogel-forming absorbent polymer can be bonded to, or otherwise supported by a support sheet. The distribution within layers 40 or 48 can be uniform or can be varied, for example to provide a shaped design that can be striped or profiled within the layer. See, for example, U.S. Pat. No. 4,935,022 (Lash et al), issued.

Layers 40 or 48 can comprise hydrogel-forming absorbent polymer integrated with or dispersed within a support sheet, such as a cellulose-based tissue or other non-woven material. The hydrogel-forming absorbent polymer can be integrated with the support sheet by bonding or by mechanical means such as embossing or calendering. Alternatively, layers 40 or 48 can comprise substantially only of hydrogel-forming absorbent polymers.

Additional layers can be incorporated in the absorbent core 20 and, as mentioned above, tissue layers can be incorporated. For example, a tissue layer can be used to encapsulate the first hydrogel-forming absorbent polymer and/or the second hydrogel-forming absorbent polymer.

Another suitable absorbent core according to the present invention involves a multi-layer structure preferably comprising: (1) an acquisition layer; (2) a storage layer which absorbent layers comprise a high concentration of hydrogel-forming absorbent polymer having the physical properties specified above (including relatively high PHL, PUP capacity and preferably SFC values) positioned subjacent the acquisition layer; and optionally a fluid previous, fluid stable, intermediate integrity layer positioned between the acquisition layer and the storage layer. The acquisition layer and storage layer comprise at least some moisture (i.e., fluid) insensitive fibers such as crimped synthetic fibers that increase the wet integrity of these two layers and form fluid stable bonds to other components of the absorbent core or absorbent article. See U.S. applications Ser. No. 08/153,739 (Dragoo et al), filed Nov. 16, 1993, and U.S application Ser. No. 08/164,049 (Dragoo et al), filed Dec. 8, 1993, which are incorporated by reference.

The inclusion of the crimped synthetic fibers in the acquisition layer improves the integrity, acquisition rate, absorbent capacity, and the resilience of the acquisition layer. The crimped synthetic fibers provide both improved intra-layer integrity and inter-layer integrity. This is due to the interlocking of the crimped synthetic fibers within the acquisition layer and the storage layer, and the availability of the crimped synthetic fibers on the surfaces of these layers for forming fluid stable bonds to the fluid stable components of the absorbent core. The absorbent core, thus, provides a plurality of layers comprising interlocking matrices of fluid stable fibers that are bonded by fluid stable bonds to adjacent fluid stable components. The absorbent core is also bonded by fluid stable bonds between the topsheet and backsheet of the absorbent article to prevent slumping of the hydrogel-forming absorbent polymer between the topsheet and backsheet (in other words, slumping inside the chassis of the absorbent article).

Figure 2:
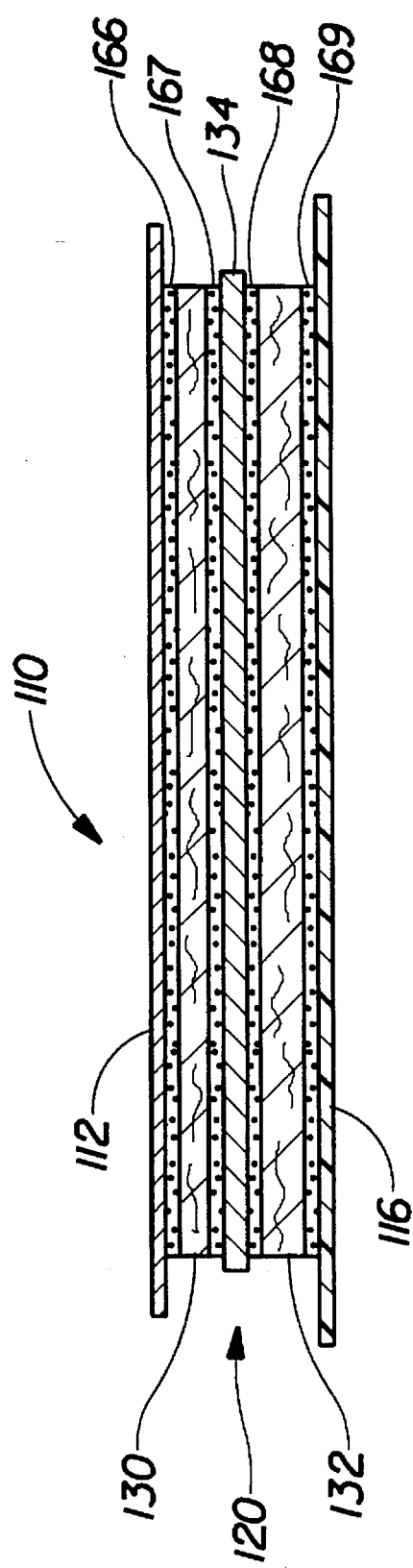
FIG. 2 is a cross-sectional view of an absorbent article showing another absorbent core according to the present invention.

One such multi-layer absorbent core is shown in FIG. 2. FIG. 2 shows a cross-section of an absorbent article indicated as 110 having a topsheet 112, a backsheet 116 and an absorbent core by 120 positioned between topsheet 112 and backsheet 116. As shown in this FIG. 2, core 120 preferably comprises an acquisition/distribution layer ("acquisition layer") 130, a storage core layer ("storage layer") 132 preferably positioned subjacent the acquisition layer 130, and an intermediate fluid stable layer (or "integrity layer") 134 positioned between the acquisition layer 130 and the storage layer 132, all of which are in fluid communication with each other. The acquisition layer 130 can be of any suitable size and need not extend the full length or width of the storage layer 132. The acquisition layer 130 can, for example, be in the form of a strip or patch. In the embodiment shown in FIG. 2, the acquisition layer 130 is shown as a single patch (i.e., web or sheet) of nonwoven material. It should be understood, however, that the acquisition layer 130 need not be a single sheet.

In addition, in other embodiments, rather than being a separate layer that is located on top of the storage layer 132, the acquisition layer 130 can be an integral layer (or component) that comprises the top layer of a laminated storage layer 132. In this regard, it should also be understood that the multiple layer absorbent core 120 can be used as the entire core or it can be used as one or more layers in a layered core construction. The multiple layer absorbent core 120 can also be constructed without the acquisition layer 130.

The overall acquisition layer 130 is preferably hydrophilic, but can have hydrophobic components. The acquisition layer 130 can comprise a woven material, a nonwoven material, or any other suitable type of material. Preferably, the acquisition layer 130 comprises a nonwoven material. When the acquisition layer 130 comprises a nonwoven material, it can be made by a number of different processes. These include, but are not limited to wet laid, air-laid, meltblown, spunbonded, carded (the latter including, thermally bonded, through-air bonded, powder bonded, latex bonded, solvent bonded, or spunlaced). The latter processes (e.g., spunbonding and carding) can be preferred if it desired to orient the fibers in the acquisition layer because it is easier to orient the fibers in a single direction in such processes.

In one preferred embodiment, acquisition layer 130 comprises at least some fibers that form fluid stable bonds. The term "fluid stable bonds", as used herein, refers to bonds that are not affected by the presence of body fluids. Preferred fibers for forming fluid stable bonds are synthetic fibers, with crimped synthetic fibers being especially preferred for providing the acquisition layer 130 with softness and resiliency. Crimped synthetic fibers are also preferred because they can interlock to provide the acquisition layer 130 with increased integrity. The acquisition layer 130 shown in FIG. 2 preferably comprises a blend of crimped synthetic fibers and either natural fibers or cross-linked cellulosic fibers.

In one preferred embodiment, the acquisition layer 130 comprises a blended layer comprising a homogeneous air-laid mixture of about 20% crimped hydrophobic polyethylene terephthalate (PET) fibers and about 80% of either airfelt or chemically stiffed cellulosic fibers. The PET fibers preferably have a denier per fiber of about 40, an uncrimped length of about 0.5 inch (about 1.3 cm), a crimp frequency of about 6 crimps per lineal inch (2.54 cm), and a crimp angle of about 88°.

While the preferred material for the crimped fibers in this embodiment is PET, alternative embodiments can be any non-water absorbing material that has a wet stiffness similar to PET. Other suitable materials for use as the crimped fibers include, but are not limited to polypropylene, nylon, polyethylene, and bicomponent fibers. In addition, the denier of the fibers preferably ranges from about 1½ or 2 dpf to about 30 dpf. The uncrimped length of the fibers preferably ranges from about 0.25 inch (about 0.6 cm) to about 2 inches (about 5 cm). The crimp frequency is preferably between about 5 and about 15 crimps per lineal inch. The crimp angle preferably ranges from about 60° to about 100°. The amount of crimped fibers in the acquisition layer can range from about 5% to about 90%, and to be practical for use in disposable absorbent articles from a cost standpoint preferably ranges from about 10% to about 50%, and most preferably about 20% to about 40%.

Acquisition layer 130 can be substantially undensified during the process of manufacturing the diaper. In alternative embodiments, the acquisition layer 130 can be densified by compressing it to densities ranging up to as high as about 4.8 g/cubic inch (about 0.3 g/cm$^3$), or more.

Further variations can be desirable when the acquisition layer 130 is used in certain types of absorbent articles. In one embodiment that is preferred when the absorbent article comprises a sanitary napkin, the acquisition layer 130 preferably comprises a spunlace nonwoven web comprised of permanently wettable fibers. Preferably, the acquisition layer 130 is a 30 g/yard$^2$ (35 g/m$^2$) PET spunlace nonwoven web. Spunlaced fabrics of this type are manufactured by the Veratec Company of Walpole, Mass. The spunlace nonwoven web is formed in such a way that most of the fibers are oriented in a single direction, such as the longitudinal direction, for preferential wicking. The fibers of this preferred acquisition layer 130 material are made of a PET resin and are coated with a proprietary permanently wettable finish known as CELWET. These fibers are obtained from the Hoechst Celanese Corporation of Charlotte, N.C.

An optional intermediate fluid stable layer 134 is preferably located between the acquisition layer 130 and the storage layer 132. Layer 134 serves two main purposes: (1) as a supporting substrate for the adjacent acquisition layer 130 and the storage layer 132 and; and (2) a structure to which fluid stable bonds can be formed with the synthetic fibers in the acquisition layer 130 and storage layer 132. Layer 134 preferably retains a high degree of its integrity when wet, should not interfere with fluid movement from the acquisition layer 130 into the storage layer 132, and is also preferably flexible so that the flexibility of the absorbent article is substantially unaffected by the presence of the fluid stable layer 134. In one preferred embodiment, layer 134 is a spunbonded polyester nonwoven web.

A commercially available spunbonded polyester nonwoven web suitable for use as fluid stable layer 134 is a material known as REEMAY® 2055 sold by Reemay, Incorporated of Old Hickory, Tenn. This material has a basis weight of about 0.55 oz./yd$^2$ (about 18.6 g/m$^2$) and is comprised of 4 denier per fiber tri-lobal cross-sectionally shaped fibers. The REEMAY web is similar to the material that is used in BOUNCE® dryer sheets manufactured by The Procter & Gamble Company of Cincinnati, Ohio under U.S. Pat. Nos. 4,073,996, 4,237,155, and 5,094,761. A key factor in selecting the polyester nonwoven web is its perviousness. The REEMAY web also contains inter-fiber spaces that are of sufficient size to permit some of the fibers in the acquisition layer 130 to penetrate into the storage layer 132 and some of the fibers in the storage layer 132 to penetrate into the acquisition layer 130.

In alternative embodiments, layer 134 can be comprised of other non-water absorbing materials that are similar to polyester. Examples of suitable materials for use as layer 134 include, but are not limited to polypropylene, nylon, and polyethylene. In addition, in other embodiments instead of using synthetic materials, layer 134 can comprise a high wet strength, low stretch (i.e., low extensibility), tissue provided in a structure in which the bonds between the high wet strength tissue and the adjacent acquisition layer 130 and storage layer 132 remain strong when wet.

In alternative embodiments, a high wet strength adhesive can be used with any of the other types of fluid stable layers 134, including but not limited to the REEMAY® material. In addition, in other alternative embodiments, layer 134 can be a nonwoven material made by another suitable process. In still other embodiments, layer 134 can be some type of material other than a nonwoven. For example, layer 134 can comprise a scrim or a net.

Further, the location of the fluid stable layer 134 within the absorbent core can vary in different embodiments. Layer 134 is preferably positioned between the acquisition layer 130 and the storage layer 132. In other embodiments, however, layer 134 can be positioned adjacent other faces of the components of the multi-layer absorbent core 120. Further, if the components of the multi-layer absorbent core 120 such as the acquisition layer and storage layer comprise more than one layer, the fluid stable layer 134 can be positioned between the layers comprising such components. In still other alternative embodiments, layer 134 can comprise more than one layer. In this case, the additional layers could be inserted between any of the components of the absorbent article.

In still other alternative embodiments, fluid stable layer 134 can be eliminated, in which case the synthetic fibers in the acquisition layer 130 and storage layer 132 can be bonded directly to each other. In these latter embodiments, the moisture insensitive fibers in the acquisition layer 130 will be bonded to other moisture insensitive fibers, the synthetic fibers in the storage layer 132.

The storage layer 132 is preferably positioned between the acquisition layer 130 and the backsheet of the absorbent article. Storage layer 132 provides the means for absorbing and containing body fluids and is generally at least slightly resiliently compressible (but preferably not collapsible), conformable, and non-irritating to the user's skin. This storage layer 132 can be referred to as a "blended" layer. Storage layer 132 comprises a web or batt of fibers, preferably in the form of a homogeneous blend of fibers. Blended storage layer 132 is comprised of at least two groups (or types) of fibers. These include a first group (or type) of fibers and a second group (or type) of fibers. The first group of fibers comprises low denier, relatively short, hydrophilic fibers. The second group of fibers comprises from about 5%, preferably at least about 10 or 20%, to about 90% of the fibers in the storage layer, of higher denier, longer, moisture insensitive synthetic fibers. (The percentage of fibers in storage layer 132 refers to the relative weight of the fibers only, and does not include the weight of any hydrogel-forming absorbent polymer.) The blend ratio of the two groups of fibers can be varied to produce the particular properties desired for different types of absorbent articles. These components and properties of the storage layer 132 are discussed in greater detail below.

The fibers in the first group of fibers can have various lengths and deniers provided that these properties of the fibers are less than those of the fibers in the second group of fibers. The fibers in the first group of fibers preferably have a length of less than or equal to about ½ inch (about 1.3 cm), more preferably less than or equal to about ¼ inch (about 0.6 cm). The fibers in the first group of fibers preferably have a denier per fiber (or per filament) of less than or equal to about 15, more preferably less than or equal to about 10, and most preferably less than or equal to about 2.

The first group of fibers can comprise natural fibers such as cotton or cellulose. The cellulose fibers can be in the form of comminuted wood pulp fibers known as airfelt. The first group of fibers can alternatively or additionally comprise synthetic fibers, including but not limited to, PET, polypropylene, polyethylene, rayon, chemical thermal mechanical pulp (or "CTMP" or TMP"), ground wood, or cross-linked cellulose fibers. The fibers in the first group of fibers are either inherently hydrophilic, or can be rendered hydrophilic by treating them in any of the manners described previously.

Performance is improved by selecting a relatively stiff fiber that maintains a substantial portion of its compression resistance when wetted for the fibers in the first group. (That is, the fibers should have a high compressive modulus.) Preferably, the fibers selected are both compression resistant under wet and dry conditions, and are wet and dry resilient (i.e., they tend to both resist compression and to spring back when compressed). Chemically stiffened fibers are especially preferred for these criteria.

The fibers in the second group of fibers are generally longer than the fibers in the first group of fibers. The fibers in the second group of fibers should also be of high compressive modulus and should maintain a relatively high modulus when wetted. The fibers in the second group of fibers should also preferably be wet and dry resilient. Suitable fibers for inclusion in the second group of fibers include, but are not limited to synthetic fibers comprised of any of those materials specified above as being suitable for use as the fibers of the acquisition layer 130. (Fiber lengths, denier, etc. can be the same, but are not necessarily the same. For example, the synthetic fibers in the acquisition layer can have one denier (e.g., a denier of about 15) for aiding in the acquisition of fluids and for greater resiliency, and the synthetic fibers in the storage layer can have a lower denier, such as about 2. Some preferred fiber lengths, etc. for the synthetic fibers in the storage layer are described below.)

Preferably, the fibers in the second group of fibers have an uncfimped length of greater than or equal to about ¼ inch (about 0.6 cm) long, more preferably greater than or equal to about ½ inch (about 1.3 cm). The denier of the fibers in the second group of fibers is preferably greater than the denier of the fibers in the first group of fibers. The fibers in the second group of fibers preferably have a denier per fiber of between about 1½ or 2 and about 50 or 60, and more preferably between about 6 and about 40. More preferably still, the denier of the fibers in the second group of fibers is between about 12 or 15 and about 30, and most preferably is between about 12 and about 25.

The fibers in the second group of fibers are fluid insensitive. That is, the fibers in the second group of fibers are not substantially affected by the presence of moisture (and, thus, will not collapse when wetted). These fibers may, however, transport fluids along their surfaces. The fibers in the second group may be hydrophilic, hydrophobic, or partially hydrophilic and partially hydrophobic. The fibers in the second group of fibers preferably have at least some hydrophilic component (which may be a cellulosic component). The fibers in the second group of fibers can be provided with a hydrophilic component in a number of suitable ways. These include, but are not limited to coating or treating the fibers to render them, or at least their surfaces, hydrophilic.

One suitable type of synthetic fibers for use in the second group of fibers is crimped polyester fibers. Suitable synthetic fibers are those formerly available from Eastman Kodak Textile Fibers Division Kingsport, TN as the KODEL® 200 and 400 Series PET fibers. One suitable type of synthetic binder fiber is the KODEL® 410 fiber. A suitable polyester fiber is the KODEL® 431 fiber. These KODEL® fibers have a denier of 15 per filament and a length of about 0.5 inch (about 1.3 cm) and are preferably crimped at a crimping frequency of between about 5 and 8, preferably about 6, more preferably 6.3 crimps per linear inch (i.e., per 2.5 cm). The fibers are preferably crimped at a crimping angle of between about 70° to about 91°, more preferably about 88°. Crimping provides the fibers with improved resilience, among other desired properties. The fibers may be coated with a hydrophilic or hydrophobic finish by any suitable method known in the art.

In alternative embodiments, it is possible to replace the natural fibers in the first group of fibers with very short, low denier, synthetic fibers (with hydrophilic surfaces). The blended storage layer 132 in such embodiments would consist of short, low denier, hydrophilic first group of synthetic fibers (such as polyester fibers with a CELWET® finish) and long, high denier second group of crimped synthetic fibers.

The blended storage layer 132 also contains hydrogel-forming absorbent polymer in amounts as previously set forth in C(1) above. The blended layer 132 is also preferably compressed to a density of at least about 1.5 g/cubic inch (about 0.09 g/cm$^3$). The blended layer 132 can be compressed to densities at least as high as about 4.0 g/cubic inch (about 0.25 g/cm$^3$) to improve fluid wicking (that is, distribution of fluids to other parts of the storage layer) while still maintaining good softness and flexibility. The blended storage layer 132 can be compressed to densities up to as high as about 5.6 g/in$^3$ to about 6.4 g/in$^3$ (about 0.35 g/cm$^3$ to about 0.40 g/cm$^3$). These higher density cores can become rather stiff, however. Therefore, if storage layer 132 is compressed to densities of about 0.35 g/cm$^3$ to about 0.40 g/cm$^3$, it is preferably mechanically flexed or otherwise manipulated to make it more flexible before it is placed in use. (For simplicity, the density values specified above do not include the weight of any particles of hydrogel-forming absorbent polymer. The overall density of the storage layer, thus, will be greatly affected by the amount of hydrogel-forming absorbent polymer in the storage layer, making it impractical to attempt to express an all-inclusive overall range of density for the storage layer.).

The three components of the preferred multiple layer absorbent core 120, the acquisition layer 130, fluid stable layer 134, and storage layer 132, are preferably held together by adhesives applied between the adjacent faces of the components. The bonds between the components of the multiple layer absorbent core 120 are particularly shown in FIG. 2. The body-facing side of the acquisition layer 130 is adhered to the underside (or garment-facing side) of the topsheet 112 by adhesive 166. The garment-facing side of the acquisition layer 130 is bonded to the body-facing side of the fluid stable layer 134 by adhesive 167. The garment-facing side of the fluid stable layer 134 is, in turn, bonded to the body-facing side of the storage layer 132 by adhesive 168. The multiple layer absorbent core 120 is also preferably adhered between the topsheet 112 and backsheet 116 by adhesives shown as layers 166 and 169. These adhesives are applied between the multiple layer absorbent core 120 and the respective inwardly facing surface (or garment-facing side) the topsheet 112 (as described above) and the body-facing side of the backsheet 116.

The adhesives are shown schematically as layers in FIG. 2 for simplicity. The adhesives, however, need not be applied only in the form of layers. The adhesives can be applied in any of the manners described with relation to the adhesives used to bond the acquisition layer to the topsheet (e.g., spirals, etc.). In addition, other types of attachment means can be used. The components of the multiple layer absorbent core can be adhered together by any of the attachment means that are described above with relation to adhering the acquisition layer to the topsheet. It should also be understood that the various different layers of the multiple layer absorbent core need not all be attached by the same type of attachment means. The layers of the multiple layer absorbent core can be attached to each other by different attachment means and/or if adhesives are used, different types of adhesive applications/patterns can be used between layers. In the preferred embodiment shown in FIG. 2, the layers of the multiple layer absorbent core are preferably held together by an open pattern network of adhesive filaments comprising several lines of adhesive filaments swirled into a spiral pattern.

The crimped synthetic fibers in acquisition layer 130 and storage layer 132 serve an important role in the wet integrity of the components of the multi-layer absorbent core 120. The crimped synthetic fibers in the acquisition layer 130 and storage layer 132 should preferably be long enough to form at least portions of the surfaces of these respective components. The synthetic fibers will typically be long enough to form at least a portion of the surface of a given layer if they have lengths that range from lengths that are equal to the thickness of the layer that they comprise up to lengths that are greater than or equal to 50% more than the thickness of the layer they comprise.

The synthetic fibers (or portions thereof) that form part of the surface of the acquisition layer and the storage layer are available to be bonded with adhesives to the adjacent layers. Since the synthetic fibers are moisture insensitive, they will be able to form fluid stable bonds (not shown) to the topsheet 112. This will ensure that the bonds do not fail when the absorbent article 110 is wetted by bodily exudates. Fluid stable bonds will also be formed between the garment-facing surface of the acquisition layer 130 and the fluid stable layer 134 (or if there is no intermediate fluid stable layer, to the body-facing surface of the storage layer 132). The crimped synthetic fibers will also form fluid stable bonds between the garment-facing surface of the fluid stable layer 134 and the body-facing surface of the storage layer 132. Fluid stable bonds will also be formed between the garment-facing surface of the storage layer 132 and the body-facing surface of the backsheet 116.

The topsheet, fluid stable layer, and backsheet are also fluid stable in that they generally resist stretching when wet and are able to serve as supporting substrates for the other layers such as the acquisition layer 130 and the storage layer 132. The acquisition layer 130 and the storage layer 132 are subject to stretching and being pulled apart under the forces associated with wearing and loading of absorbent article 110 with body fluids. The acquisition layer 130 and storage layer 132, however, are bonded to these fluid stable layers at fixed fluid stable bond sites. The acquisition layer and storage layer are, thus, in effect, anchored to the topsheet, backsheet, and intermediate fluid stable layer in such a manner that the bonding ties these nonwoven layers to fluid stable layers. The acquisition layer and storage layer are, as a result, able to utilize the resistance to stretching of the adjacent substrates to resist intra-layer separation (e.g., failing by an elongation or strain-related failure mechanism) due to the forces associated with wearing of absorbent article 110 such as bending of the article, wearer activity, and loading of the article with body fluids.

The construction of the multiple layer absorbent core described above, thus, provides an interlocking, compression resistant, fluid stable matrix of synthetic fibers and fluid stable components that are inter-connected and remain inter-connected during use. The multiple layer absorbent core 120 is, thus, resistant to both compression and to tensional forces (i.e., strain-related forces) so that it maintains its void volume and can stay in its prior-to-use condition when wetted and under the loads associated with wearing the absorbent article.

Another suitable absorbent core according to the present invention involves a primary core integrity layer, preferably formed of a continuous mesh of meltblown material, that envelopes the core to provide improved core integrity, especially when wet. See U.S Pat. No. 5,387,208 (Ashton et al), issued Feb. 7, 1995, which is incorporated by reference. The primary core integrity layer that is preferably joined to a chassis component of the absorbent article, preferably directly joined to the topsheet. The bond between the primary core integrity layer and the chassis component is preferably relatively cohesive and therefore tends to retain its strength in use such that the absorbent core has a reduced tendency to separate from the chassis component(s). In addition, the absorbent core components have a reduced tendency to slip away and/or separate from one another, particularly upon wetting.

The absorbent core enveloped by the primary core integrity layer preferably comprises multiple absorbent layers (one of which absorbent layers comprises a high concentration of hydrogel-forming absorbent polymer having at least the PHL, PUP capacity, and preferably SFC values described in B(1)(b) above) with at least one secondary core integrity layer positioned between one or more of the absorbent layers. In a particularly preferred embodiment, this absorbent core comprises an acquisition/distribution layer, a storage layer, and a tissue layer positioned between the acquisition/distribution layer and the storage layer. The secondary core integrity layer is preferably positioned between the acquisition/distribution layer and the tissue layer.

The primary and secondary core integrity layers are preferably formed from a thermoplastic material, more preferably a hot-melt adhesive such that the core integrity layers can be readily formed on-line during construction of the absorbent article. More preferably, the core integrity layers are formed from a hot-melt, elastomeric adhesive. Elastomeric, hot-melt adhesives tend to be flexible such that there is a reduced tendency for adhesive and/or cohesive failure of the bonds effecting joinder in the article (relative to non-elastomeric adhesives). As a result, the absorbent core has an enhanced tendency to remain in place and to retain its integrity. Most preferably, the core integrity layers are formed from an elastomeric, hot-melt, pressure-sensitive adhesive. The tack of the pressure-sensitive adhesive further reduces the tendency of absorbent core components adjacent the primary or secondary core integrity layers to separate from other absorbent article components, and is particularly effective in reducing slippage/separation of the acquisition/distribution layer from the storage layer.

Figure 3:
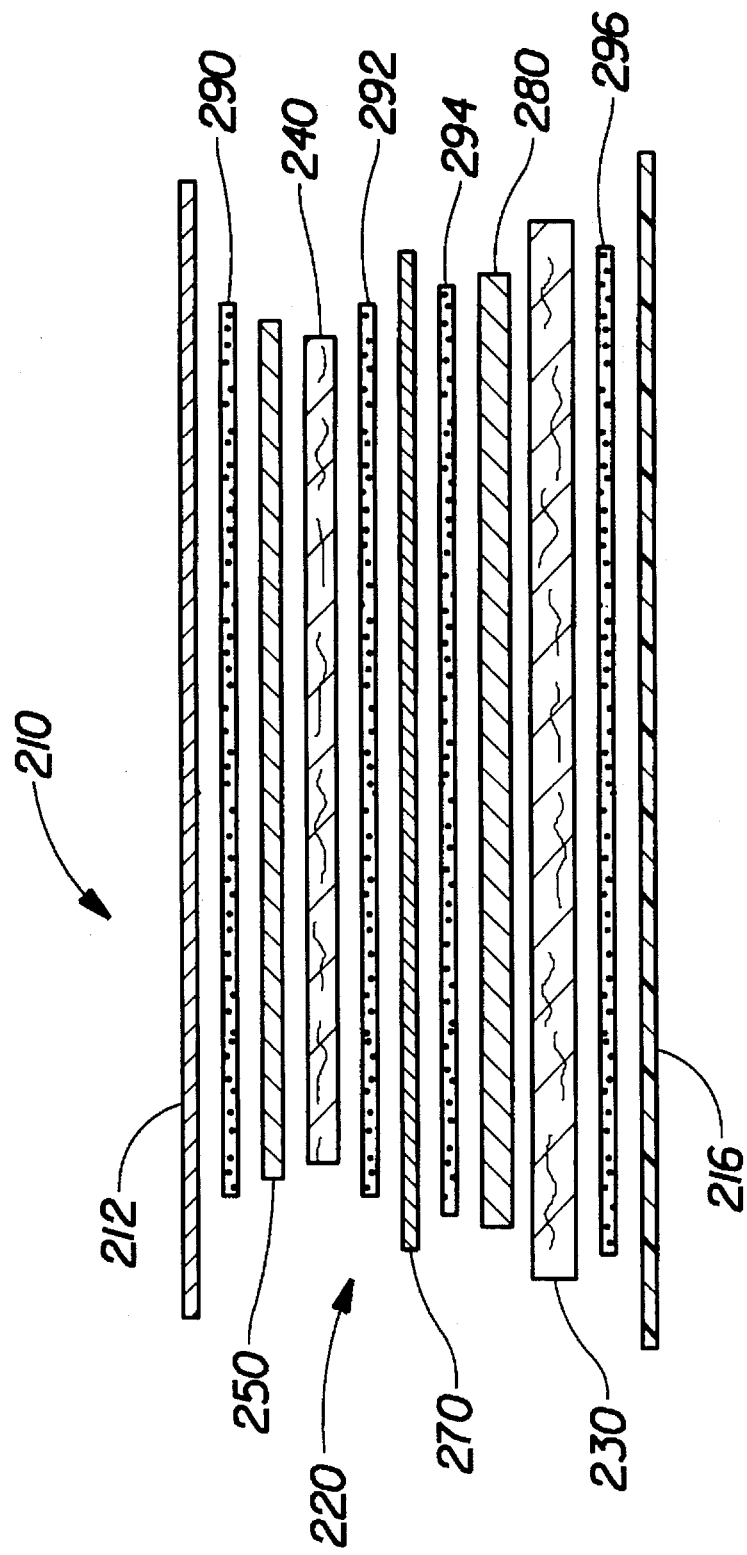
FIG. 3 is a cross-sectional view of an absorbent article showing another absorbent core according to the present invention.

One such absorbent core is shown in FIG. 3. FIG. 3 shows a cross-section of an absorbent article indicated as 210 having a topsheet 212, a backsheet 216 and an absorbent core indicated by 220 positioned between topsheet 212 and backsheet 216. As shown in this Figure, core 220 is shown as comprising a storage layer 280 that comprises the high concentration of hydrogel-forming absorbent polymer, tissue layer 270, and acquisition/distribution layer 250. As also shown in FIG. 3, core 220 also has a primary core integrity layer 230 and a secondary core integrity layer 240. The primary core integrity layer 230 is positioned between the backsheet 216 and the storage layer 280. The secondary core integrity layer 240 is positioned between the acquisition/distribution layer 250 and the tissue layer 270. As also shown in FIG. 3, the primary core integrity layer 230 extends beyond and envelopes the side edges of acquisition/distribution layer 250, the side edges of tissue layer 270, the side edges of storage layer 280; and the garment facing surface of absorbent core 220. FIG. 3 also shows construction adhesive layers 290, 292, 294, and 296.

As shown in FIG. 3, the secondary core integrity layer 240 is joined to the tissue layer 270 by construction adhesive layer 292. The secondary core integrity layer 240 is positioned adjacent the acquisition/distribution layer 250. Depending on the bond strength of the secondary core integrity layer 240 material to the acquisition/distribution layer 250, the secondary core integrity layer 240 may be joined to the acquisition/distribution layer 250 by the hot-melt or pressure-sensitive properties of the preferred secondary core integrity layer 240 material.

As further shown in FIG. 3, the tissue layer 270 is joined to the storage layer 280 by construction adhesive layer 294. The primary core integrity layer 230 is positioned adjacent the storage layer 280. Depending on the bond strength of the primary core integrity layer 230 material to the storage layer 280, the primary core integrity layer 230 can be joined to the storage layer 280 by the hot-melt or pressure-sensitive properties of the preferred primary core integrity layer 230 material.

As further shown in FIG. 3, the acquisition/distribution layer 250 is joined to the topsheet 212 by construction adhesive layer 290. The primary core integrity layer 230 is joined to the backsheet 216 by construction adhesive layer 296, and to the topsheet 212 by the hot-melt or pressure-sensitive properties of the primary core integrity layer 230 material.

As shown in FIG. 3, construction adhesive layer 290 extends outside the side edges of the acquisition/distribution layer 250 and inside the side edges of tissue layer 270. Construction adhesive layer 290 can be wider than the tissue layer 270 so as to effect joinder of the primary core integrity layer 230 to the topsheet 212. However, for economic reasons a separate application of a construction adhesive will usually be made to effect such joinder. Construction adhesive layer 292 is shown in FIG. 3 to extend in the same manner as construction adhesive layer 290. Construction adhesive layer 294 extends inside the side edges of the storage layer 280, and for economic reasons preferably extends a maximum lateral distance of up to about the narrowest width of the storage layer 280 in the crotch region of the absorbent core. As shown in FIG. 3, construction adhesive layer 296 extends inside the side edges of the primary core integrity layer 230. Construction adhesive layer 296 can alternatively extend outside the side edges of primary core integrity layer 230 in order to effect joinder of backsheet 116 to the topsheet 212. In a preferred embodiment, construction adhesive layers 290, 292, 294, and 296 are applied over the entire length (not shown) of at least one of the acquisition/distribution layer 250, tissue layer 270, storage layer 280, backsheet 216, or topsheet 212.

The primary core integrity layer 230 that preferably envelopes at least one layer of the absorbent core 220 and which is joined, preferably directly joined, to a chassis component (e.g., the topsheet 212 or backsheet 216) of the absorbent article. The primary core integrity layer 230 tends to improve the integrity of the absorbent layers that it envelopes. Thus, in a preferred embodiment, the primary core integrity layer 230 envelopes each of the layers of the absorbent core 220. The following description is therefore directed to a primary core integrity layer that envelopes each of the layers of the absorbent core 220. It should be understood, however, that improvements in absorbent core integrity can be obtained by using a configuration in which the primary core integrity layer envelopes only one or some of the absorbent layers of the absorbent core 220. For example, the integrity of an acquisition/distribution layer 250, and thus of the absorbent core 220 incorporating the same, can be improved by enveloping only the acquisition/distribution layer 250 with the primary core integrity layer 230. In addition, a primary core integrity layer that does not envelope any of the absorbent core layers can be used to improve the absorbent core integrity. For example, the surface area dimensions of the primary core integrity layer can be less than those of each absorbent core layer (the primary core integrity layer would then be positioned and joined as described herein for a secondary core integrity layer that does not envelope any of the absorbent core layers). However, it is believed that enhanced absorbent core integrity is achieved where the primary core integrity layer envelopes at least one absorbent core layer, such that this embodiment is preferred.

By "enveloped," it is meant that primary core integrity layer 230 encloses or surrounds at least a portion of the absorbent core 220 (or layer thereof). In a preferred embodiment, the primary core integrity layer 230 envelopes at least a portion of the side edges of absorbent core 220 and at least one of the surfaces of the absorbent core. The primary core integrity layer 230 will typically envelope the side edges of one or more layers in the Y-Z-dimension.

The primary core integrity layer 230 additionally serves to hold the absorbent core 220 in a relatively stable position, since the absorbent core will be physically constrained by the primary core integrity layer. It is also believed that primary core integrity layer 230 helps to maintain the adhesive bonds that typically join the absorbent core and chassis component of absorbent articles, e.g., where a construction adhesive is used to join these components. The primary core integrity layer is particularly useful in maintaining the integrity of the adhesive bonds typically joining cellulosic fibers of absorbent core 220 to a polymeric chassis, more particularly a chassis formed of or coated with a synthetic polymeric material (hereinafter "synthetic polymeric chassis").

Since the primary core integrity layer 230 forms a relatively strong bond and physically constrains absorbent core 220, the primary core integrity layer tends to reduce the forces encountered by the relatively weak, cellulosic fiber-construction adhesive-polymeric chassis bonds such that these latter bonds have a reduced tendency toward breakage. Further, if the cellulosic fiber-construction adhesive-polymeric chassis bonds do fail, the relatively strong primary core integrity layer-chassis bond tends to retain the absorbent core in a relatively stable position. Thus, the absorbent core has a reduced tendency to separate from the chassis component. This positive effect on adhesion can be particularly important when the absorbent article is wetted. When the cellulosic fibers and hydrogel-forming absorbent polymer that are incorporated into the absorbent core expand upon wetting, the forces exerted by the expanding cellulosic fibers and hydrogel-forming absorbent polymer tend to cause a loss of adhesion between the fibers, hydrogel-forming absorbent polymer, and chassis (adhesive failure tends to occur between the fibers and/or hydrogel-forming absorbent polymer and the construction adhesive, rather than the chassis and construction adhesive).

By effectively constraining the absorbent core, the primary core integrity layer 230 also reduces the tendency of the other layers in absorbent core 220 to slip away and/or separate from one another. This tendency toward slippage and/or separation is further reduced where the primary core integrity layer comprises a tacky, pressure-sensitive material. It is believed that the above described physical constraint, relatively strong primary core integrity layer-chassis bond, and/or tack reduce the tendency of the absorbent core or components thereof to slump, break, and/or rope. As a result, the absorbent core is more effectively utilized such that the absorbent article has improved absorption characteristics and reduced leakage.

The primary core integrity layer 230 comprises a continuous, fluid previous mesh of thermoplastic material. The thermoplastic material is preferably a hot-melt adhesive, more preferably a hot-melt, pressure-sensitive adhesive. The thermoplastic material is also preferably elastomeric.

By "mesh", it is meant that the thermoplastic material is in the form of strands that are interconnected to form apertures. As formed by a meltblown process, the individual strands are preferably sinuous (wavy) and oriented in substantially the same direction with at least some crosswise linking to form an intertwining web of the strands. "Strands" is meant to include fibers, threads, filaments, and other forms that have a relatively large longitudinal to cross-sectional dimension. By "fluid previous mesh," it is meant that the mesh has a sufficient number of apertures of sufficient size per unit area to allow relatively unimpeded fluid transport through the mesh. Thus, the mesh typically has a basis weight as described herein.

By "continuous" mesh, it is meant that substantially all of the strands are connected to at least one other strand. Typically, the strands are cohesively connected at each of the points where the strands intertwine. (As understood in the art, cohesion refers to the force that holds adjacent molecules of a single material together. As used herein, "relatively cohesive" bonding is believed to result from the force of attraction between two or more similar materials, e.g., two or more synthetic polymeric materials.)

Various thermoplastic materials such as are known in the art can be used for making primary core integrity layer 230. Examples of thermoplastic materials include polymers of ethylenically unsaturated monomers such as polyethylene, polypropylene, polystyrenes, polyvinyl chloride, polyvinyl acetate, polymethyl methacrylate, polyethyl acrylate, polyacrylonitrile, and the like; copolymers of ethylenically unsaturated monomers such as copolymers of ethylene and propylene, styrene, or polyvinyl acetate; styrene and maleic anhydride, methyl methacrylate, ethyl acrylate, or acrylonitrile; methyl methacrylate and ethylacrylate; and the like; polymers and copolymers of conjugated dienes such as polybutadiene, polyisoprene, polychloroprene, styrene-butadiene rubber, ethylene-propylene-diene rubber, acrylonitrile-styrene butadiene rubber and the like; saturated and unsaturated polyesters including alkyds and other polyesters; nylons and other polyamides; polyesteramides and polyurethanes; chlorinated polyethers; epoxy polymers; and cellulose esters such as cellulose acetate butyrate, and the like. Blends of thermoplastic materials can also be used, including, but not limited to, physical mixtures and copolymers. Particularly suitable thermoplastic materials include polyethylene, polypropylene, polyesters, ethylene vinyl acetate, and blends thereof.

Various hot-melt adhesives such as are know in the art can also be used. Hot-melt adhesives are typically based on one or more types of thermoplastic materials, such as those described above. Thus, the hot-melt adhesives used herein can be a thermoplastic material or a composition comprising a thermoplastic material. The various hot-melt adhesives known in the art are suitable for use herein.

The thermoplastic material is preferably elastomeric. Elastomeric materials are believed to be particularly useful for maintaining the integrity of the absorbent core while the absorbent core is subjected to flexural or torsional forces such as encountered in use. More particularly, elastomeric adhesives are believed to have better adhesion to the absorbent article components than non-elastomeric adhesives, particularly under the dynamic conditions encountered in use of the absorbent article. By "elastomeric," "elastic," etc., it is meant that the material is able to be stretched to at least twice its original length and to retract to approximately its original length when released. Exemplary elastomeric, hot-melt adhesives include thermoplastic elastomers such as ethylene vinyl acetates, polyurethanes, polyolefin blends of a hard component (generally a crystalline polyolefin such as polypropylene or polyethylene) and a soft component (such as ethylene-propylene rubber); copolyesters such as poly(ethylene terephthalate-coethylene azelate); and thermoplastic elastomeric block copolymers having thermoplastic end blocks and rubbery mid blocks designated as A-B-A block copolymers; mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprene-styrene block copolymer with polystyrene; and the elastomeric, hot-melt, pressure-sensitive adhesives described herein. Elastomeric, hot-melt adhesives of these types are described in more detail in U.S. Pat. No. 4,731,066 (Korpman) issued Mar. 15, 1988, which is incorporated by reference.

Preferred hot-melt adhesives for forming the primary core integrity layer. are hotmelt, pressure-sensitive adhesives. Hot-melt, pressure-sensitive adhesives, as understood by those of ordinary skill in the art, have some degree of surface tack at use temperatures. These tacky materials typically have a viscosity at room temperature (about 20° C. to about 25° C.) which is sufficiently low to permit good surface contact yet high enough to resist separation under stress, typically on the order of $10^4$–$10^6$ centipoise. Due to their surface tack, the pressure-sensitive adhesives used herein tend to increase the coefficient of friction between absorbent article components that may be adjacent to the pressure-sensitive adhesive, for example, the absorbent core layers. In addition, the pressure-sensitive adhesives provide manufacturing flexibility since joinder of the primary core integrity layer to other absorbent article components can then occur via the pressure-sensitive properties of the adhesive alter the adhesive has solidified. Various hot-melt, pressure-sensitive adhesives are known in the art and are suitable for use herein.

Preferred hot-melt, pressure-sensitive adhesives are also elastomeric. Elastomeric, hot-melt, pressure-sensitive adhesives are disclosed in the above referenced and incorporated U.S. Pat. No. 4,731,066, and include those materials based on thermoplastic block copolymers, polyacrylates, and ethylene vinyl acetate. Suitable elastomeric, hot-melt, pressure-sensitive adhesives include the A-B-A block copolymer based adhesives that are specified as H-2085 and H-2031 by Findley Adhesives, Inc., of Wauwatosa, Wis.

The primary core integrity layer 230 can be formed using a meltblown fiber process. Meltblown fiber processes and equipment are generally known in the art. In general, the thermoplastic material is heated to and held at a temperature sufficient to allow meltblown processing, typically at least until the material is in a liquid or molten state (melt/liquefaction temperature). (In general, the selection of any given temperature in the meltblown process is limited by the degradation temperature of the particular thermoplastic material being processed.) The molten/liquefied material is extruded under pressure (gun pressure) through orifices in a meltblown glue gun. Upon extrusion, the molten/liquid material is subjected to air flowing under pressure (air pressure) which fiberizes the material (strands are formed). The meltblown glue gun and air are heated to a desired gun temperature and air temperature, respectively, in order to facilitate strand formation. During and/or alter strand formation, the thermoplastic material cools to form stabilized strands of the thermoplastic material. The apparatus is configured such that the strands are laid onto a desired substrate.

The meltblown process parameters are preferably selected to provide a mesh having a certain strand orientation and denier. These parameters include the melt/liquefaction temperature, gun temperature, air pressure, and air temperature. In a preferred embodiment, these parameters are varied to enable the formation of sinuous (wavy) strands which are oriented in substantially the same direction with some crosswise linking to form an intertwining web of the strands.

In addition, it is generally desired to form relatively large denier strands, since the degree of wetting of the thermoplastic material to the absorbent core and thus the degree of improvement in absorbent core integrity tends to increase with increasing strand denier. The strands preferably have a denier of at least about 60 microns, preferably from about 80 microns to about 200 microns, more preferably about 90 to about 200 microns, most preferably about 100 to about 200 microns.

In general, as the viscosity of the thermoplastic material being meltblown decreases, strand formation more readily occurs, with the resultant strands tending to have a finer denier. The viscosity also influences the strand orientation, the orientation tending to become more random with decreasing viscosity. The viscosity for a given material typically decreases with an increasing melt/liquefaction temperature and particularly with increasing gun temperature. Therefore, the melt/liquefaction and gun temperatures are selected to provide a viscosity that enables strand formation as desired.

The melt/liquefaction temperature is typically from about 121° C. (250° F.) to about 204° C. (400° F.), preferably about 149° C. (300° F.) to about 190° C. (375° F.). The adhesives designated H-2031 and H-2085 are typically held at a temperature of from about 135° C. (275° F.) to about 204° C. (400° F.), preferably about 149° C. (300° F.) to about 177° C. (350° F.), more preferably about 165° C. (330° F.).

The gun temperature is typically at or above the melt/liquefaction temperature, preferably above the latter temperature in order to facilitate strand formation. The gun temperature is typically from about 149° C. (300° F.) to about 204° C. (400° F.), preferably about 163° C. (325° F.) to about 190° C. (375° F.), more preferably about 182° C. (360° F.).

The air pressure influences both strand orientation and denier. For a given material and set of process temperatures (particularly gun and air temperatures), as the air pressure increases the strands tend to form in a more random orientation and with a finer denier. The air pressure is preferably at least high enough to form strands of molten/liquefied thermoplastic material which touch and thus are able to interconnect while the thermoplastic material is in a sufficiently molten/liquid state, as described below. In a preferred embodiment, the air pressure is selected to enable the formation of sinuous strands in substantially the same direction with some crosswise linking to form an intertwining web of strands. Thus, it is preferred that the air pressure is not so high as to cause the formation of strands in random orientation. Typically, the air pressure is from about 4 psi to about 15 psi, preferably about 6 to about 10 psi, more preferably about 7 to about 9 psi, most preferably about 8 psi.

The air temperature will generally be selected so as to maintain the extruded thermoplastic material in the molten/liquefied state. Thus, the air temperature will usually be greater than or equal to the gun temperature in order to offset any cooling effects that might otherwise occur. Preferably, the air temperature is sufficient to ensure the interconnection of the individual strands of thermoplastic material on the substrate (although the extruded material need not be in the same melt/liquefaction state as when first extruded, it is preferably sufficiently molten/liquefied to enable interconnection of the strands). Typically, the air temperature is from about 204° C. (400° F.) to about 238° C. (460° F.), preferably from about 215° C. (420° F.) to about 227° C. (440° F.), more preferably about 221° C. (430° F.). Upon cooling to a temperature sufficient to resolidify the thermoplastic material, the resultant mesh of interconnected strands is stabilized.

The thermoplastic material is applied to the substrate (e.g., an absorbent core component) so as to not interfere substantially with absorption of the absorbent core. Thus, the basis weight of the mesh of thermoplastic material is typically from about 2 to about 8 grams/square meter (g/m$^2$), preferably about 3 to about 7 g/m$^2$, more preferably about 4 to about 6 g/m$^2$, most preferably about 5 g/m$^2$.

The particular meltblown equipment used herein is typically selected according to the width of the absorbent core (or absorbent core component) which is to be enveloped. In general, the equipment is selected which will provide, in one step, a width of mesh of thermoplastic material that is sufficient to envelope the absorbent core. (Where a primary core integrity layer or secondary core integrity layer as described herein is not intended to envelope at least a portion of the side edges of an absorbent core component, the meltblown glue gun is selected to provide a mesh width that is smaller than the width of the absorbent core component). For the absorbent articles herein, a 2 module, 3.0" width meltblown glue gun designated AMBI-3.0-2 and a 4 module, 6" width meltblown glue gun designated AMBI-6.0-4, each available from J and M Laboratories of Dawsonville, Ga., are suitable for use.

The primary core integrity layer 230 is preferably formed by the meltblown process in a continuous process (on-line) during manufacture of the absorbent article. Alternatively, the primary core integrity layer can be formed by the above meltblown process or by conventional methods in an intermediate process for later incorporation into the absorbent article. Thus, the primary core integrity layer may be a preformed, non-woven, fluid pervious web comprising strands of thermoplastic material. However, since the use of preformed non-wovens tends to add to the ultimate cost of the absorbent article, this alternative is not preferred.

As described above, the primary core integrity layer 230 is preferably positioned such that it envelopes the absorbent core 220. The primary core integrity layer is also joined to at least one of the chassis components (e.g., the topsheet 212 and backsheet 216) of absorbent article 210. In a preferred embodiment, the primary core integrity layer 230 is directly joined to a chassis component, preferably the topsheet 212. The primary core integrity layer can be joined to a chassis component by a construction adhesive. Alternatively, the primary core integrity layer can be joined to a chassis component by the hot-melt or pressure-sensitive properties of the thermoplastic material of the primary core integrity layer, where such materials are used.

In a preferred embodiment, the primary core integrity layer 230 is directly joined to the chassis component by a construction adhesive. Suitable construction adhesives include any of the adhesive materials such as are known in the art of bonding absorbent cores to chassis components, including those described herein in reference to joining the backsheet 216 and the absorbent core 220. The construction adhesive can comprise any of the hot-melt adhesives described in reference to the thermoplastic materials for forming the primary core integrity layer.

The construction adhesive can be applied to a given substrate (e.g., the primary core integrity layer, an absorbent core component, or a chassis component) by conventional methods such as described herein in reference to joinder of the backsheet and absorbent core. Preferably, the construction adhesive is applied in an open pattern of construction adhesive. As used herein, "open pattern of construction adhesive" means that the construction adhesive is present on a substrate in a pattern that allows for relatively unimpeded fluid transport into and/or through the absorbent core. Suitable open patterns and methods of making the same are disclosed in the U.S. Pat. Nos. 4,573,986; 3,911,173; 4,785,996; and 4,842,666, which are incorporated by reference. Thus, the open pattern of construction adhesive may comprise a fine pattern of globulettes of construction adhesive or reticulated networks of filaments of construction adhesive, including spiral and/or bead patterns. The globulettes and filaments may have diameters about equal in order of magnitude to the effective average diameter of the fibers that constitute the absorbent core 220. The construction adhesive may also be applied by a meltblown process, including the process described for making the primary core integrity layer.

In a preferred embodiment, the absorbent core 220 comprises a secondary core integrity layer 240, positioned between various absorbent layers, preferably webs or batts, of the absorbent core. (As should be understood by those of ordinary skill in the art, such absorbent layers can, like the absorbent core, have a garment facing surface, body facing surface, side edges, and end edges.) The secondary core integrity layer 240 in preferred absorbent articles 210 will thus be positioned between the primary core integrity layer 230 and the chassis component to which the primary core integrity layer is joined. (However, where the primary core integrity layer envelopes only a portion of the 220 absorbent core layers, a secondary core integrity layer 240 can be positioned between absorbent core layers that are not enveloped by the primary core integrity layer.) The secondary core integrity layer 240 comprises a continuous mesh of thermoplastic material, as defined in reference to the primary core integrity layer. The secondary core integrity layer 240 is joined to a chassis component and can be directly joined thereto, e.g., where the secondary core integrity layer envelopes the absorbent core layers positioned between the secondary core integrity layer and the chassis.

The secondary core integrity layer 240 may or may not envelope one or more absorbent layers of absorbent core 220. As shown in FIG. 3, the lateral width of the secondary core integrity layer 240 is less than the lateral width of each of the various absorbent layers of the absorbent core, i.e., lateral width of the secondary core integrity layer 240 is less than the lateral widths of each of acquisition/distribution layer 250, tissue layer 270, and storage layer 280). Thus, the secondary core integrity layer 240 does not envelope the side edges of, respectively, the acquisition/distribution layer 250, the tissue layer 270, and the storage layer 280.

The secondary core integrity layer 240 can alternatively envelope the absorbent layers as described for the primary core integrity layer 230. The extent of enveloping can be the same or different from that of the primary core integrity layer or any other secondary core integrity layer. Thus, the secondary core integrity layer 240 can envelope relatively different longitudinal portions of the side edges of an absorbent layer, and/or a different surface and/or relative portion of a surface of an absorbent layer.

The secondary core integrity layer 240 can be formed of a thermoplastic material and by a process as described for the primary core integrity layer. The secondary core integrity layer can be formed of the same thermoplastic material as the primary core integrity layer 230 or from a different thermoplastic material. For ease of processing, the secondary core integrity layer is preferably formed of the same thermoplastic material as is the primary core integrity layer. In addition, the secondary core integrity layer can be formed using process parameters that are the same or different from those used to form the primary core integrity layer. Preferably, the same process parameters are used such that the secondary core integrity layer has a basis weight, and the strands of thermoplastic material thereof have a denier and orientation, which are substantially the same as the primary core integrity layer.

The secondary core integrity layer 240 can be joined to one or more absorbent core layers and/or a chassis component. Joinder can occur using a construction adhesive and/or by the hot-melt and/or pressure-sensitive properties of the secondary core integrity layer material, as described for joinder of the primary core integrity layer to a chassis component.

The absorbent article 210 shown in FIG. 3 can be formed in the following manner. A secondary core integrity layer 240 is formed on the garment facing surface of acquisition/distribution layer 250. The secondary core integrity layer 240 is joined to tissue layer 270 by construction adhesive layer 292 that is preferably applied to the body facing surface of tissue layer 270. The garment facing surface of tissue layer 270 is then joined to storage layer 280 by construction adhesive layer 294 that is preferably applied to the garment facing surface of tissue layer 270. The resultant laminate is then joined to the topsheet 212 by construction adhesive layer 290, which joins the acquisition/distribution layer 250 to topsheet 212. The primary core integrity layer 230 is formed on the garment facing surface of storage layer 280, a portion of the garment facing surface of tissue layer 270 (corresponding to the differential lateral distance between side edges of the storage layer 280 and the side edges of tissue layer 270), and a portion of the garment facing surface of topsheet 112 (corresponding to the differential lateral distance between the side edges of tissue layer 270 and the side edges of the primary core integrity layer 230). The backsheet 216 is then joined to the primary core integrity layer 230 by construction adhesive layer 296 and to the topsheet 212 by a construction adhesive (not shown).

Other suitable absorbent core according to the present invention can be in the form of a layer of hydrogel-forming absorbent polymer contained between two other fibrous layers, e.g., a laminated absorbent core. Suitable laminated absorbent cores according to the present invention can be prepared using procedures similar to those described in U.S. Pat. No. 4,260,443 (Lindsay et al); U.S. Pat. No. 4,467,012 (Pedersen et al), issued Aug. 21, 1984; U.S. Pat. No. 4,715,918 (Lang), issued Dec. 29, 1987; U.S. Pat. No. 4,851,069 (Packard et al), issued Jul. 25, 1989; U.S. Pat. No. 4,950,264 (Osborn), issued Aug. 21, 1990; U.S. Pat. No. 4,994,037 (Bernardin), issued Feb. 19, 1991; U.S. Pat. No. 5,009,650 (Bernardin), issued Apr. 23, 1991; U.S. Pat. No. 5,009,653 (Osborn), issued Apr. 23, 1991; U.S. Pat. No. 5,128,082 (Makoui), Jul. 7, 1992; U.S. Pat. No. 5,149,335 (Kellenberger et al), issued Sep. 22, 1992; and U.S. Pat. No. 5,176,668 (Bernardin),issued Jan. 5, 1993 (all of which are incorporated by reference) but using hydrogel-forming absorbent polymer having least the PHL, PUP capacity and preferably SFC values described in B(1)(b) above.

Other suitable laminated absorbent cores according to the present invention involving thermally bonded layers are disclosed in U.S. application Ser. No. 141,156 (Richards et al), filed Oct. 21, 1993, which is incorporated by reference. These thermally bonded absorbent cores comprise: (1) a primary thermally bonded fluid distribution layer; (2) optionally, but preferably a secondary fluid distribution layer in fluid communication with, and being capable of acquiring aqueous body fluids from, the primary distribution layer; (3) a fluid storage layer in fluid communication with either the primary or secondary fluid distribution layer that comprises a high concentration of hydrogel-forming absorbent polymer having at least the PHL, PUP capacity and preferably SFC values described in B(1)(b) above; and (4) optionally a "dusting" layer adjacent the storage layer. These absorbent cores are typically used in conjunction with a thermally bonded acquisition layer (referred to as a "secondary topsheet").

Figure 4:
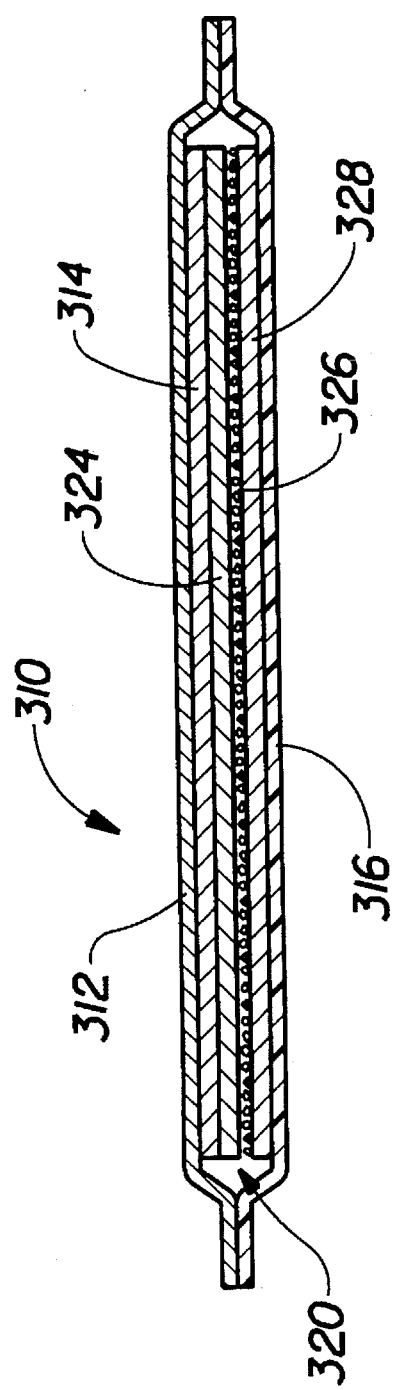
FIG. 4 is a cross-sectional view of an absorbent article showing another absorbent core according to the present invention.

An embodiment of these thermally bonded absorbent cores is shown in FIG. 4. FIG. 4 shows a cross-section of an absorbent article particularly suitable as a catamenial indicated as 310 having a fluid pervious primary topsheet 312, a fluid impervious backsheet 316 and an absorbent structure positioned between topsheet 312 and backsheet 316 comprising fluid acquisition layer 314 commonly referred to as a "secondary topsheet" and an absorbent core indicated by 320. As shown in this Figure, absorbent core 320 is shown in FIG. 4 as comprising three components: a fluid distribution layer 324, a fluid storage layer 326 and fibrous "dusting" layer 328. In forming this absorbent core, the "dusting" layer 328 provides the initial layer upon which the hydrogel-forming absorbent polymer of the storage layer 326 is deposited. The distribution layer 324 is then positioned over the deposited hydrogel-forming absorbent material thus forming a laminate-type structure. Although it is possible to join dusting layer 328 and distribution layer 326 through the use of an adhesive, these two layers are typically joined together by thermal bonding since each of these layers comprise some thermoplastic material, typically thermoplastic binder fibers.

Figure 5:
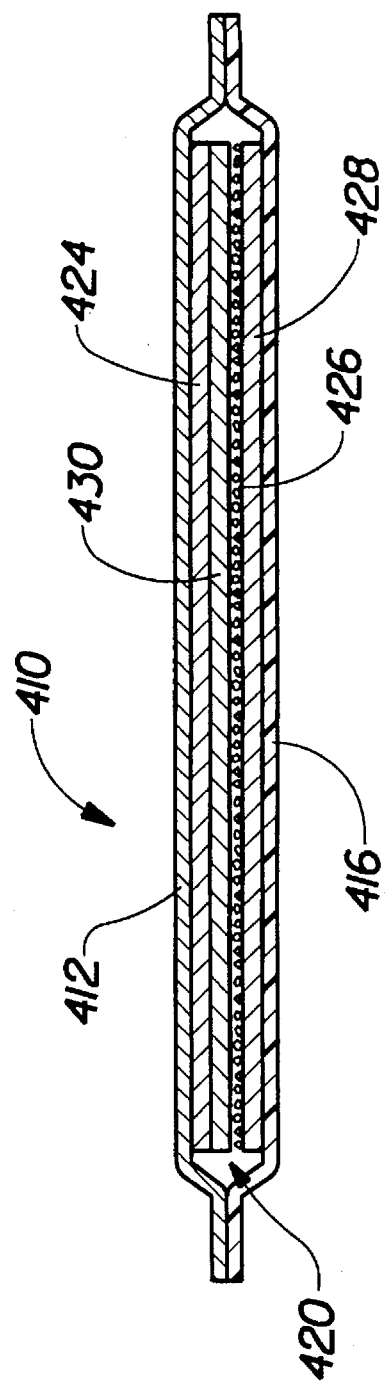
FIG. 5 is a cross-sectional view of an absorbent article showing an alternative absorbent core to that shown in FIG. 4.

An alternative embodiment of this thermally bonded absorbent core is shown in FIG. 5. FIG. 5 shows a cross-section of an absorbent article particularly suitable as a catamenial indicated as 410 having a topsheet 412, a backsheet 416 and an absorbent core indicated as 420 positioned between topsheet 412 and backsheet 416. As shown in FIG. 5, absorbent core 420 comprises four components: a primary fluid distribution layer 424, a secondary fluid distribution layer 430, a fluid storage layer 426 and fibrous "dusting" layer 428. Again, the "dusting" layer 428 provides the point for depositing the hydrogel-forming absorbent polymer of storage layer 426. The secondary and primary distribution layers 430 and 424 are then positioned over the deposited absorbent polymer to form a laminate-type structure. This laminate is typically joined together by thermal bonding.

Figure 6:
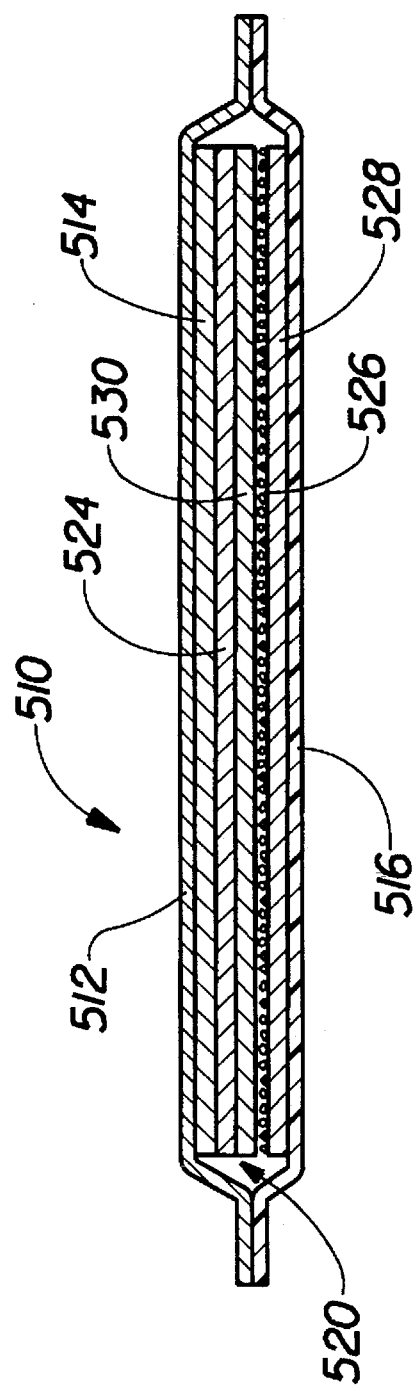
FIG. 6 is a cross-sectional view of an absorbent article showing another alternative absorbent core to that shown in FIGS. 4 and 5.

FIG. 6 shows a combination of the embodiments shown in FIGS. 4 and 5. Like the embodiment shown in FIG. 4, absorbent article 510 comprises a topsheet 512, a backsheet 516 and an absorbent structure positioned between topsheet 512 and backsheet 516 comprising a secondary topsheet 514 and an absorbent core 520. Like the embodiment shown in FIG. 5, absorbent core 520 of FIG. 6 comprises four components: a primary fluid distribution layer 524, a secondary fluid distribution layer 530, a fluid storage layer 526 and fibrous "dusting" layer 528.

Other suitable absorbent cores according to the present invention can be prepared from meltblown synthetic fibers and coform mixtures (i.e., mixtures of cellulosic and meltblown synthetic fibers, and the like), such as disclosed in U.S. Pat. No. 5,149,335 (Kellenberger et al), issued Sep. 22, 1992, which is incorporated by reference. For example, a coformed web containing 75% hydrogel-forming absorbent polymer having at least the PHL, PUP capacity, and preferably SFC values described in B(1)(b) above and 25% of a fine fibered (less than about 5 micrometer diameter) meltblown HYDROFIL® LCFX copolymer fibers can be formed. This meltblown web is then covered on one surface with a layer of a HYDROFIL® meltblown web (see Examples 2 and 3 from U.S. Pat. No. 5,149,335). The absorbent core thus formed is then placed between two layers of bilobal polypropylene spunbonded material (see Examples 2 and 3 of U.S. Pat. No. 5,149,335) with the spunbonded material being heat sealed around the periphery of the absorbent structure.

Absorbent cores containing a layer of meltblown fibers and particles of hydrogel-forming absorbent polymer having at least the PHL, PUP capacity and preferably SFC values described in B(1)(b) above can also be formed according to the procedure described in U.S. Pat. No. 4,429,001 (Kolpin et al), issued Jan. 31, 1984, which is incorporated by reference. For some absorbent articles, two or more separately formed layers of these meltblown fibers and absorbent polymer particles can be assembled to form thicker absorbent core. Also the stream of meltblown fibers and absorbent polymers particles can be deposited onto another sheet material such as a porous nonwoven web that is to form part of the eventual absorbent core. Other fibers besides meltblown fibers can be introduced into the absorbent core. For example, crimped bulking fibers can be mixed with meltblown fibers together with absorbent polymer particles to prepare a more lofty or lightweight absorbent core.

E. Absorbent Articles

Because of the unique absorbent properties of the absorbent cores of the present invention, they are especially suitable for use in absorbent articles, especially disposable absorbent articles. As used herein, the term "absorbent article" refers to articles that absorb and contain body fluids, and more specifically refers to articles that are placed against or in proximity to the body of the wearer to absorb and contain the various fluids discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). A preferred embodiment of a disposable absorbent article according to the present invention is a diaper. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, catamenial pads, sanitary napkins, facial tissues, paper towels, and the like.

These absorbent articles typically comprise a fluid impervious backsheet, a fluid pervious topsheet joined to, or otherwise associated with the backsheet, and an absorbent core according to the present invention positioned between the backsheet and the topsheet. The topsheet is positioned adjacent the body surface of the absorbent core. The topsheet is preferably joined to the absorbent core and to the backsheet by attachment means such as those well known in the art. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In preferred absorbent articles, the topsheet and the backsheet are joined directly to each other at the periphery thereof. The topsheet and backsheet can also be indirectly joined together by directly joining them to the absorbent core by the attachment means.

The backsheet is typically impervious to body fluids and is preferably manufactured from a thin plastic film, although other flexible fluid impervious materials may also be used. As used herein, the term "flexible" refers to materials that are compliant and will readily conform to the general shape and contours of the human body. The backsheet prevents body fluids absorbed and contained in the absorbent core from wetting articles that contact the such as pants, pajamas, undergarments, and the like. The backsheet can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet can permit vapors to escape from the absorbent core (i.e., breathable) while still preventing body fluids from passing through the backsheet.

The topsheet is compliant, soft feeling, and non-irritating to the wearer's skin. Further, the topsheet is fluid pervious permitting body fluids to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

Preferred topsheets for use in absorbent articles of the present invention are selected from high loft nonwoven topsheets and aperture formed film topsheets. Apertured formed films are especially preferred for the topsheet because they are pervious to body fluids and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. No. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird), issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for use in catamenial products of the present invention is the formed film described in one or more of the above patents and marketed on sanitary napkins by The Procter & Gamble Company of Cincinnati, Ohio as "DRI-WEAVE®."

The body surface of the formed film topsheet can be hydrophilic so as to help body fluids to transfer through the topsheet faster than if the body surface was not hydrophilic so as to diminish the likelihood that fluid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

F. Test Methods

1. Saline Flow Conductivity (SFC)

This test determines the Saline Flow Conductivity (SFC) of the gel layer formed from hydrogel-forming absorbent polymer that is swollen in Jayco synthetic urine under a confining pressure. The objective of this test is to assess the ability of the hydrogel layer formed from a hydrogel-forming absorbent polymer to acquire and distribute body fluids when the polymer is present at high concentrations in an absorbent member and exposed to usage mechanical pressures. Darcy's law and steady-state flow methods are used for determining saline flow conductivity. (See, for example, "Absorbency," ed. by P. K. Chatterjee, Elsevier, 1985, Pages 42–43 and "Chemical Engineering" Vol. II, Third Edition, J. M. Coulson and J. F. Richardson, Pergamon Press, 1978, Pages 125–127.)

The hydrogel layer used for SFC measurements is formed by swelling a hydrogel-forming absorbent polymer in Jayco synthetic urine for a time period of 60 minutes. The hydrogel layer is formed and its flow conductivity measured under a mechanical confining pressure of 0.3 psi (about 2 kPa). Flow conductivity is measured using a 0.118M NaCl solution. For a hydrogel-forming absorbent polymer whose uptake of Jayco synthetic urine versus time has substantially leveled off, this concentration of NaCl has been found to maintain the thickness of the hydrogel layer substantially constant during the measurement. For some hydrogel-forming absorbent polymers, small changes in hydrogel-layer thickness can occur as a result of polymer swelling, polymer deswelling, and/or changes in hydrogel-layer porosity. A constant hydrostatic pressure of 4920 dyne/cm$^2$ (5 cm of 0.118M NaCl) is used for the measurement.

Flow rate is determined by measuring the quantity of solution flowing through the hydrogel layer as a function of time. Flow rate can vary over the duration of the measurement. Reasons for flow-rate variation include changes in the thickness of the hydrogel layer and changes in the viscosity of interstitial fluid, as the fluid initially present in interstitial voids (which, for example, can contain dissolved extractable polymer) is replaced with NaCl solution. If flow rate is time dependent, then the initial flow rate, typically obtained by extrapolating the measured flow rates to zero time, is used to calculate flow conductivity. The saline flow conductivity is calculated from the initial flow rate, dimensions of the hydrogel layer, and hydrostatic pressure. For systems where the flow rate is substantially constant, a hydrogel-layer permeability coefficient can be calculated from the saline flow conductivity and the viscosity of the NaCl solution.

Figure 7:
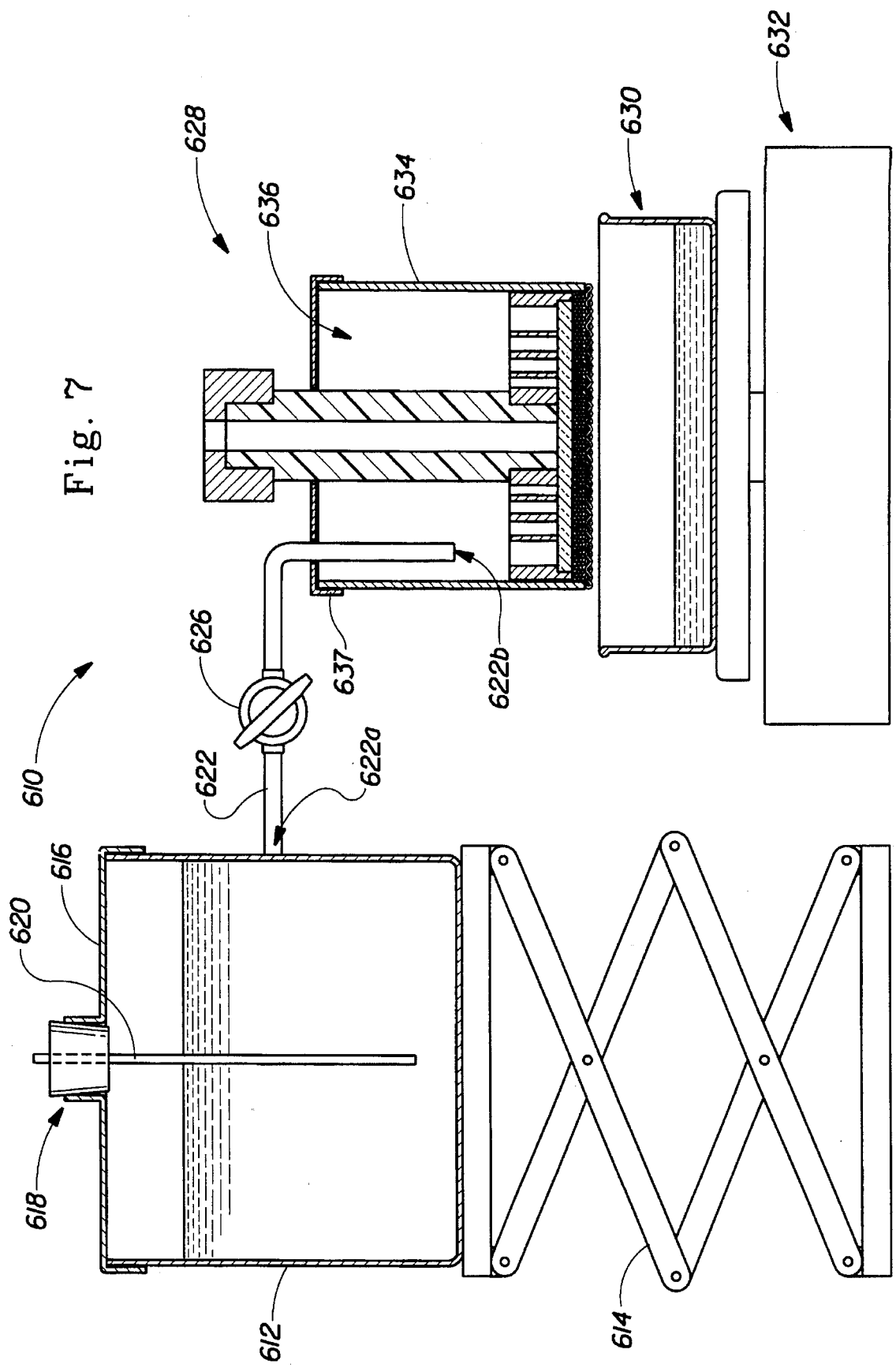
FIG. 7 represents a schematic view of an apparatus for measuring the Saline Flow Conductivity (SFC) value of the hydrogel-forming absorbent polymers.

A suitable apparatus 610 for this test is shown in FIG. 7. This apparatus includes a constant hydrostatic head reservoir indicated generally as 612 that sits on a laboratory jack indicated generally as 614. Reservoir 612 has lid 616 with a stoppered vent indicated by 618 so that additional fluid can be added to reservoir 612. An openended tube 620 is inserted through lid 616 to allow air to enter reservoir 612 for the purpose of delivering fluid at a constant hydrostatic pressure. The bottom end of tube 620 is positioned so as to maintain fluid in cylinder 634 at a height of 5.0 cm above the bottom of hydrogel layer 668 (see FIG. 8).

Reservoir 612 is provided with a generally L-shaped delivery tube 622 having an inlet 622a that is below the surface of the fluid in the reservoir. The delivery of fluid by tube 622 is controlled by stopcock 626. Tube 622 delivers fluid from reservoir 612 to a piston/cylinder assembly generally indicated as 628. Beneath assembly 628 is a support screen (not shown) and a collection reservoir 630 that sits on a laboratory balance 632.

Figure 8:
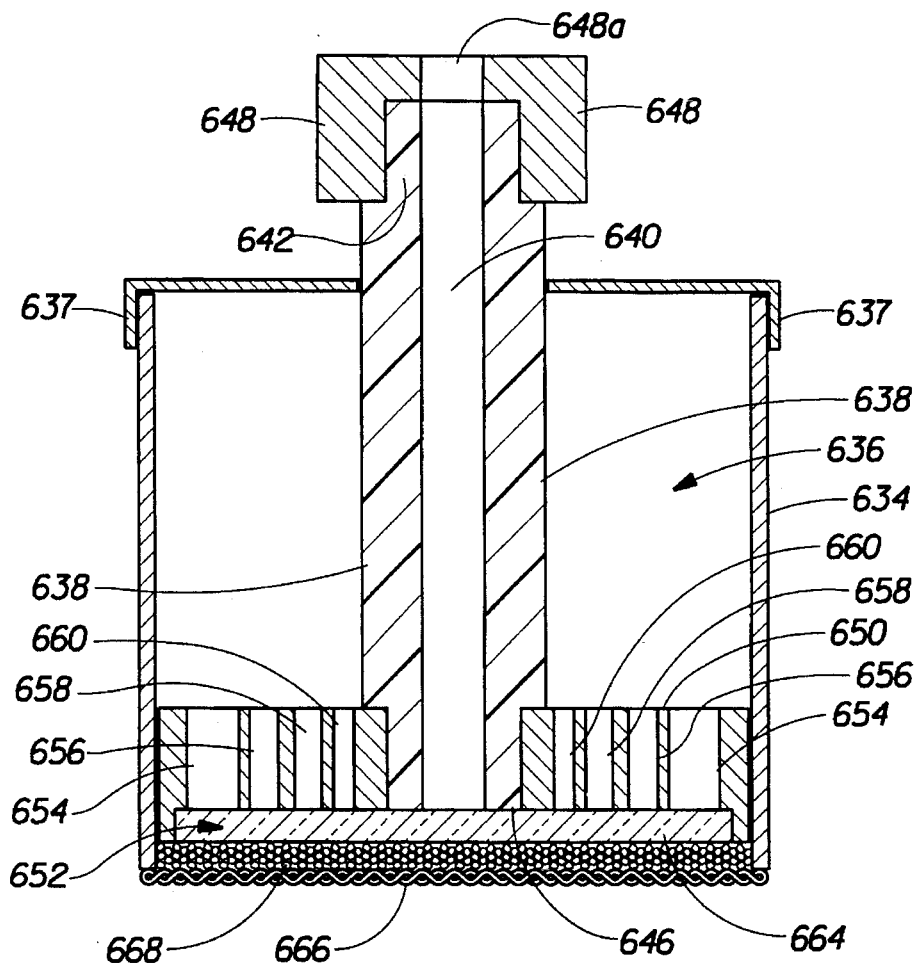
FIG. 8 represents an enlarged sectional view of the piston/cylinder assembly shown in FIG. 7.

Referring to FIG. 7, assembly 628 basically consists of a cylinder 634, a piston generally indicated as 636 and a cover 637 provided with holes for piston 636 and delivery tube 622. As shown in FIG. 7, the outlet 622b of tube 622 is positioned below the bottom end of tube 620 and thus will also be below the surface of the fluid (not shown) in cylinder 634. As shown in FIG. 8, piston 636 consists of a generally cylindrical LEXAN® shaft 638 having a concentric cylindrical hole 640 bored down the longitudinal axis of the shaft. Both ends of shaft 638 are machined to provide ends 642 and 646. A weight indicated as 648 rests on end 642 and has a cylindrical hole 648a bored through the center thereof.

Figure 9:
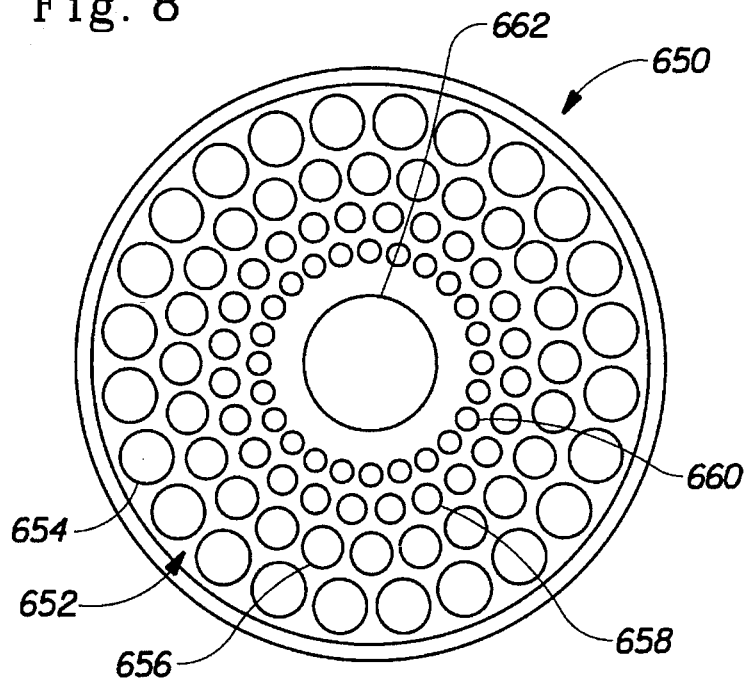
FIG. 9 represents a plan view of the bottom of the piston head from the piston/cylinder assembly shown in FIG. 8.

Inserted on the other end 646 is a generally circular Teflon piston head 650 having an annular recess 652 in the bottom thereof. Piston head 650 is sized so as to slidably move inside cylinder 634. As particularly shown in FIG. 9, piston head 650 is provided with four concentric rings of twenty-four cylindrical holes each indicated generally as 654, 656, 658, and 660. As can be seen in FIG. 9, concentric rings 654 to 660 fit within the area defined by recess 652. The holes in each of these concentric rings are bored from the top to bottom of piston head 650. The holes in each ring are spaced by approximately 15 degrees and offset by approximately 7.5 degrees from the holes in adjacent rings. The holes in each ring have a progressively smaller diameter going inwardly from ring 654 (0.204 inch diameter) to ring 660 (0.111 inch diameter). Piston head 650 also has cylindrical hole 662 bored in the center thereof to receive end 646 of shaft 638.

As shown in FIG. 8, a fritted circular glass disc 664 fits within recess 652. Attached to bottom end of cylinder 634 is a No. 400 mesh stainless steel cloth screen 666 that is biaxially stretched to tautness prior to attachment. The sample of hydrogel-forming absorbent polymer indicated as 668 is supported on screen 666.

Cylinder 634 is bored from a transparent LEXAN® rod or equivalent and has an inner diameter of 6.00 cm (area=28.27 cm²), a wall thickness of approximately 0.5 cm, and a height of approximately 6.0 cm. Piston head 650 is machined from a solid Teflon rod. It has a height of 0.625 inches and a diameter that is slightly less than the inner diameter of cylinder 634, so that it fits within the cylinder with minimum wall clearances, but still slides freely. Recess 652 is approximately 56 mm in diameter by 4 mm deep. Hole 662 in the center of the piston head 650 has a threaded 0.625 inch opening (18 threads/inch) for end 646 of shaft 638. Fritted disc 664 is chosen for high permeability (e.g., Chemglass Cat No. CG-201-40, 60 mm diameter; X-Coarse Porosity) and is ground so that it fits snugly within recess 652 of piston head 650, with the bottom of the disc being flush with the bottom of the piston head. Shaft 638 is machined from a LEXAN® rod and has an outer diameter of 0.875 inches and an inner diameter of 0.250 inches. End 646 is approximately 0.5 inches long and is threaded to match hole 662 in piston head 650. End 642 is approximately an inch long and 0.623 inches in diameter, forming an annular shoulder to support the stainless steel weight 648. Fluid passing through the hole 640 in shaft 638 can directly access the flitted disc 664. The annular stainless steel weight 648 has an inner diameter of 0.625 inches, so that it slips onto end 642 of shaft 638 and rests on the annular shoulder formed therein. The combined weight of flitted glass disc 664, piston 636 and weight 648 equals 596 g, which corresponds to a pressure of 0.3 psi for an area of 28.27 cm². Cover 637 is machined from LEXAN® or its equivalent and is dimensioned to cover the top of cylinder 634. It has an 0.877 inch opening in the center thereof for shaft 638 of piston 636 and a second opening near the edge thereof for delivery tube 622.

The cylinder 634 rests on a 16 mesh rigid stainless steel support screen (not shown) or equivalent. This support screen is sufficiently permeable so as to not impede fluid flow into the collection reservoir 630. The support screen is generally used to support cylinder 634 when the flow rate of saline solution through assembly 628 is greater than about 0.02 g/sec. For flow rates less than about 0.02 g/sec, it is preferable that there be a continuous fluid path between cylinder 634 and the collection reservoir. This can be accomplished by replacing the support screen, collection reservoir 630, and analytical balance 632 with analytical balance 716, reservoir 712, fritted funnel 718, and the respective connecting tubes and valves of apparatus 710 (see FIG. 10), and positioning cylinder 634 on the fritted disc in fritted funnel 718.

Jayco synthetic urine used in this method is prepared by dissolving a mixture of 2.0 g KCl, 2.0 g $Na_2SO_4$, 0.85 g $NH_4H_2PO_4$, 0.15 g $(NH_4)_2HPO_4$, 0.19 g $CaCl_2$, and 0.23 g $MgCl_2$ to 1.0 liters with distilled water. The salt mixture can be purchased from Endovations, Reading, Pa (cat No. JA-00131-000-01).

The 0.118M NaCl solution is prepared by dissolving 6.896 g NaCl (Baker Analyzed Reagent or equivalent) to 1.0 liters with distilled water.

An analytical balance 632 accurate to 0.01 g (e.g., Mettler PM4000 or equivalent) is typically used to measure the quantity of fluid flowing through the hydrogel layer 668 when the flow rate is about 0.02 g/sec or greater. A more accurate balance (e.g., Mettler AE200 or equivalent) can be needed for less permeable hydrogel layers having lower flow rates. The balance is preferably interfaced to a computer for monitoring fluid quantity versus time.

The thickness of hydrogel layer 668 in cylinder 634 is measured to an accuracy of about 0.1 mm. Any method having the requisite accuracy can be used, as long as the weights are not removed and the hydrogel layer is not additionally compressed or disturbed during the measurement. Using a caliper gauge (e.g., Manostat 15-100-500 or equivalent) to measure the vertical distance between the bottom of the stainless steel weight 648 and the top of cover 637, relative to this distance with no hydrogel layer 668 in cylinder 634 is acceptable. Also acceptable is the use of a depth gauge (e.g., Ono Sokki EG-225 or equivalent) to measure the position of piston 636 or stainless steel weight 648 relative to any fixed surface, compared to its position with no hydrogel layer in cylinder 634.

The SFC measurement is performed at ambient temperature (i.e., 20°–25° C.) and is carried out as follows:

0.9 gm aliquot of hydrogel-forming absorbent polymer (corresponding to a basis weight of 0.032 gm/cm²) is added to cylinder 634 and distributed evenly on screen 666. For most hydrogel-forming absorbent polymers, moisture content is typically less than 5%. For these, the quantity of hydrogel-forming absorbent polymer to be added can be determined on a wet-weight (as is) basis. For hydrogel-forming absorbent polymers having a moisture content greater than about 5%, the added polymer weight should be corrected for moisture (i.e., the added polymer should be 0.9 g on a dry-weight basis). Care is taken to prevent hydrogel-forming absorbent polymer from adhering to the cylinder walls. Piston 636 (minus weight 648) with disc 664 positioned in recess 652 of piston head 650 is inserted into cylinder 634 and positioned on top of the dry hydrogel-forming absorbent polymer 668. If necessary, piston 636 can be turned gently to more-uniformly distribute the hydrogel-forming absorbent polymer on screen 666. Cylinder 634 is the covered with cover 637 and weight 648 is then positioned on end 642 of shaft 638.

A fritted disc (coarse or extra coarse) having a diameter greater than that of cylinder 634 is positioned in a wide/shallow flat-bottomed container that is filled to the top of the fritted disc with Jayco synthetic urine. The piston/cylinder assembly 628 is then positioned on top of this fritted glass disc. Fluid from the container passes through the flitted disc and is absorbed by the hydrogel-forming absorbent polymer 668. As the polymer absorbs fluid, a hydrogel layer is formed in cylinder 634. After a time period of 60 minutes, the thickness of the hydrogel layer is determined. Care is taken that the hydrogel layer does not lose fluid or take in air during this procedure.

The piston/cylinder assembly 628 is then transferred to apparatus 610. The support screen (not shown) and any gap between it and the piston/cylinder assembly 628 is presaturated with saline solution. If the flitted funnel 718 of the PUP apparatus 710 is used to support cylinder 634, the surface of the fritted funnel should be minimally elevated relative to the height of the fluid in the collection reservoir, with valves between the fritted funnel and the collection reservoir being in the open position. (The flitted funnel elevation should be sufficient such that fluid passing through the hydrogel layer does not accumulate in the funnel.)

The SFC measurement is initiated by adding NaCl solution through hole 640 in shaft 638 in order to expel air from piston head 650 and then turning stopcock 626 to an open position so that delivery tube 622 delivers fluid to cylinder 634 to a height of 5.0 cm above the bottom of hydrogel layer 668. Although the measurement is considered to have been initiated ($t_o$) at the time NaCl solution is first added, the time at which a stable hydrostatic pressure, corresponding to 5.0 cm of saline solution, and a stable flow rate is attained ($t_s$) is noted. (The time $t_s$ should typically be about one minute or less.) The quantity of fluid passing through hydrogel layer 668 versus time is determined gravimetrically for a time period of 10 minutes. After the elapsed time, piston/cylinder assembly 628 is removed and the thickness of hydrogel layer 668 is measured. generally the change in thickness of the hydrogel layer is less than about 10%.

In general, flow rate need not be constant. The time-dependent flow rate through the system, $F_s(t)$ is determined, in units of g/sec, by dividing the incremental weight of fluid passing through the system (in grams) by incremental time (in seconds). Only data collected for times between $t_s$ and 10 minutes is used for flow rate calculations. Flow rate results between $t_s$ and 10 minutes is used to calculate a value for $F_s(t=0)$, the initial flow rate through the hydrogel layer. $F_s(t=0)$ is calculated by extrapolating the results of a least-squares fit of $F_s(t)$ versus time to $t=0$.

For a layer having a very high permeability (e.g., a flow rate greater than ~2 g/sec), it may not be practical to collect fluid for the full 10 minute time period. For flow rates greater than ~2 g/sec, the time of collection can be shortened in proportion to the flow rate.

For some hydrogel-forming absorbent polymers having extremely low permeability, absorption of fluid by the hydrogel competes with transport of fluid through the hydrogel layer and either there is no flow of fluid through the hydrogel layer and into the reservoir or, possibly, there is a net absorption of fluid out of the PUP reservoir. For these extremely low permeability hydrogel layers, it is optional to extend the time for Jayco synthetic urine absorption to longer periods (e.g., 16 hours).

In a separate measurement, the flow rate through apparatus 610 and the piston/cylinder assembly 628 ($F_a$) is measured as described above, except that no hydrogel layer is present. If $F_a$ is much greater than the flow rate through the system when the hydrogel layer is present, $F_s$, then no correction for the flow resistance of the SFC apparatus and the piston/cylinder assembly is necessary. In this limit, $F_g=F_s$, where $F_g$ is the contribution of the hydrogel layer to the flow rate of the system. However if this requirement is not satisfied, then the following correction is used to calculate the value of $F_g$ from the values of $F_s$ and $F_a$:

$$F_g=(F_a \times F_s)/(F_a-F_s)$$

The Saline Flow Conductivity (K) of the hydrogel layer is calculated using the following equation:

$$K=\{F_g(t=0) \times L_0\}/\{\rho \times A \times \Delta P\},$$

where $F_g(t=0)$ is the flow rate in g/sec determined from regression analysis of the flow rate results and any correction due to assembly/apparatus flow resistance, $L_0$ is the initial thickness of the hydrogel layer in cm, $\rho$ is the density of the NaCl solution in gm/cm$^3$. A is the area of the hydrogel layer in cm$^2$, $\Delta P$ is the hydrostatic pressure in dyne/cm$^2$, and the saline flow conductivity, K, is in units of cm$^3$ sec/gm.

The average of three determinations should be reported.

For hydrogel layers where the flow rate is substantially constant, a permeability coefficient ($\kappa$) can be calculated from the saline flow conductivity using the following equation:

$$\kappa=K\eta,$$

where $\eta$ is the viscosity of the NaCl solution in poise and the permeability coefficient, $\kappa$, is in units of cm$^2$.

The following is an example of how SFC is calculated according to the present invention:

The measured value of $F_a$ is 412 g/min=6.87 g/sec. For a single determination on the particulate hydrogel-forming polymer sample 3-5 (Example 3), the extrapolated value for $F_s(t=0)$ is 33.9 g/min=0.565 g/sec, with a very-low ratio of slope:intercept of $9 \times 10^{-5}$ sec$^{-1}$. Correcting for apparatus resistance:

$$F_g=(6.87 \times 0.565) \div (6.87-0.565)=0.616 \text{ g/sec}$$

Given a 0.118M saline density of 1.003 g/cm$^3$ (CRC Handbook of Chemistry and Physics, 61st Edition) a hydrogel-layer thickness of 1.134 cm, a hydrogel layer area of 28.27 cm$^2$, and a hydrostatic pressure of 4920 dyne/cm$^2$.

$$K=(0.616 \times 1.134)/(1.003 \times 28.27 \times 4920)=5.0 \times 10^{-6} \text{ cm}^3\text{sec/gm}$$

Considering the substantially constant flow rate and given a 0.118M saline viscosity of 0.01015 poise (CRC Handbook of Chemistry and Physics, 61st Edition):

$\kappa = K\eta = (5.0 \times 10^{-6}) \times 0.01015 = 5.1 \times 10^{-8} \text{ cm}^2$ 2. Performance Under Pressure (PUP) Capacity This test determines the 60 minute gram/gram absorption of synthetic urine for a hydrogel-forming absorbent polymer that is laterally confined in a piston/cylinder assembly under a confining pressure of 0.7 psi (about 5 kPa). The objective of the test is to assess the ability of a hydrogel-forming absorbent polymer layer to absorb body fluids, over a practical period of time, when the polymer is present at high basis weight and high concentrations in an absorbent member and exposed to usage pressures. Usage pressures against which a hydrogel-forming polymer is forced to absorb urine against include mechanical pressures resulting from the weight and/or motions of the wearer, mechanical pressures resulting from elastics and fastening systems, and the hydrostatic suction resulting from adjacent capillary (e.g., fibrous) layers and/or structures as they are drained of fluid.

The test fluid for the PUP capacity test is Jayco synthetic urine. This fluid is absorbed by the hydrogel-forming absorbent polymer under demand absorption conditions at near-zero hydrostatic pressure.

Figure 10:
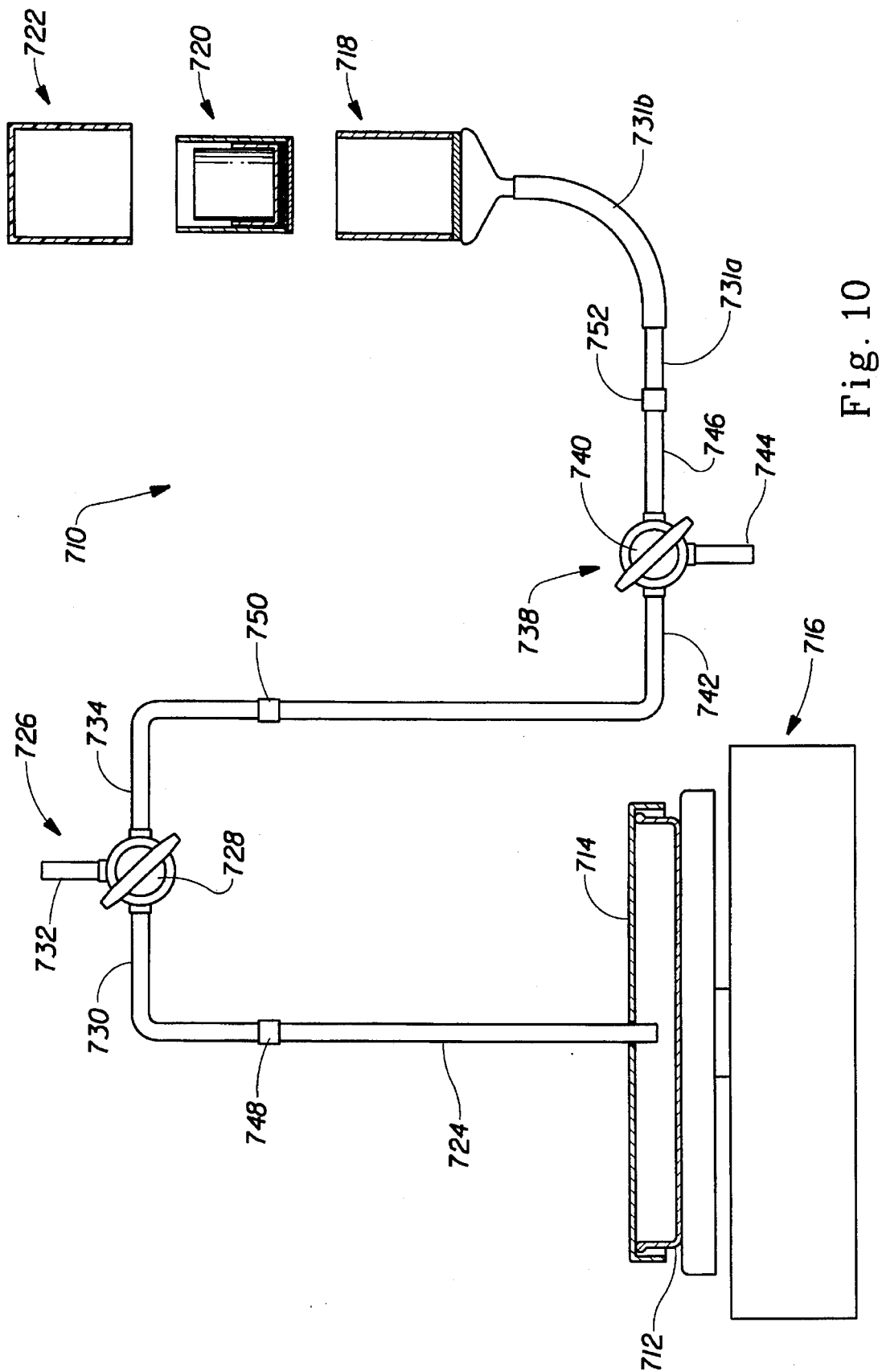
FIG. 10 represents a schematic view of an apparatus for measuring the Performance Under Pressure (PUP) capacity of the hydrogel-forming absorbent polymers.

A suitable apparatus 710 for this test is shown in FIG. 10. At one end of this apparatus is a fluid reservoir 712 (such as a petri dish) having a cover 714. Reservoir 712 rests on an analytical balance indicated generally as 716. The other end of apparatus 710 is a fritted funnel indicated generally as 718, a piston/cylinder assembly indicated generally as 720 that fits inside funnel 718, and cylindrical plastic fritted funnel cover indicated generally as 722 that fits over funnel 718 and is open at the bottom and closed at the top, the top having a pinhole. Apparatus 710 has a system for conveying fluid in either direction that consists of sections glass capillary tubing indicated as 724 and 731a, flexible plastic tubing (e.g., ¼ inch i.d. and ⅜ inch o.d. Tygon tubing) indicated as 731b, stopcock assemblies 726 and 738 and Teflon connectors 748, 750 and 752 to connect glass tubing 724 and 731a and stopcock assemblies 726 and 738. Stopcock assembly 726 consists of a 3-way valve 728, glass capillary tubing 730 and 734 in the main fluid system, and a section of glass capillary tubing 732 for replenishing reservoir 712 and forward flushing the fritted disc in fritted funnel 718. Stopcock assembly 738 similarly consists of a 3-way valve 740, glass capillary tubing 742 and 746 in the main fluid line, and a section of glass capillary tubing 744 that acts as a drain for the system.

Figure 11:
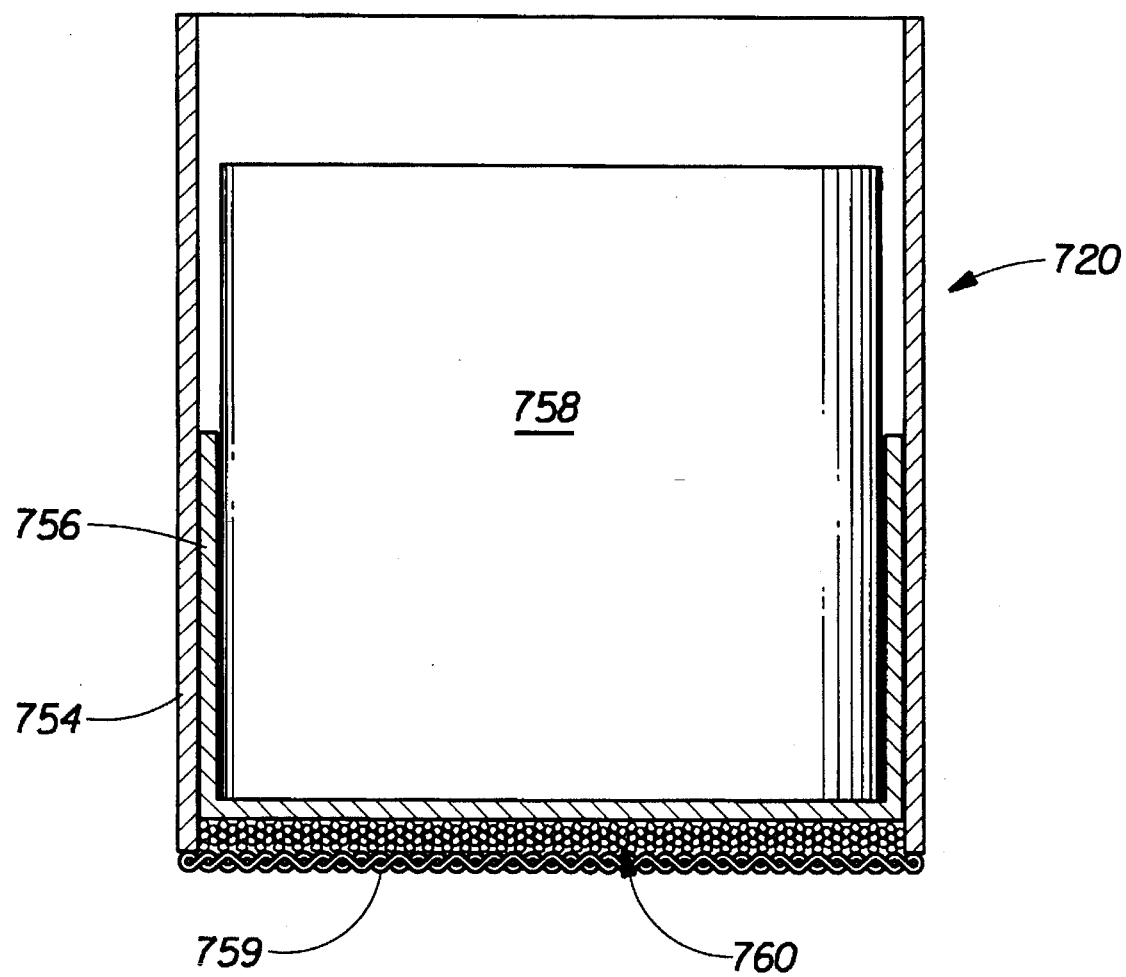
FIG. 11 represents an enlarged sectional view of the piston/cylinder assembly shown in FIG. 10.

Referring to FIG. 11, assembly 720 consists of a cylinder 754, a cup-like piston indicated by 756 and a weight 758 that fits inside piston 756. Attached to bottom end of cylinder 754 is a No. 400 mesh stainless steel cloth screen 759 that is biaxially stretched to tautness prior to attachment. Hydrogel-forming absorbent polymer indicated generally as 760 rests on screen 759. Cylinder 754 is bored from a transparent LEXAN® rod (or equivalent) and has an inner diameter of 6.00 cm (area=28.27 cm²), with a wall thickness of approximately 5 mm and a height of approximately 5 cm. The piston 756 is in the form of a Teflon cup and is machined to fit into cylinder 754 within tight tolerances. Cylindrical stainless steel weight 758 is machined to fit snugly within piston 756 and is fitted with a handle on the top (not shown) for ease in removing. The combined weight of piston 756 and weight 758 is 1390 g, which corresponds to a pressure of 0.7 psi for an area of 28.27 cm².

The components of apparatus 710 are sized such that the flow rate of synthetic urine therethrough, under a 10 cm hydrostatic head, is at least 0.01 g/cm²/sec, where the flow rate is normalized by the area of fritted funnel 718. Factors particularly impactful on flow rate are the permeability of the fritted disc in fritted funnel 718 and the inner diameters of glass tubing 724, 730, 734, 742, 746 and 731a, and stopcock valves 728 and 740.

Reservoir 712 is positioned on an analytical balance 716 that is accurate to at least 0.01 g with a drift of less than 0.1 g/hr. The balance is preferably interfaced to a computer with software than can (i) monitor balance weight change at pre-set time intervals from the initiation of the PUP test and (ii) be set to auto initiate on a weight change of 0.01–0.05 g, depending on balance sensitivity. Capillary tubing 724 entering the reservoir 712 should not contact either the bottom thereof or cover 714. The volume of fluid (not shown) in reservoir 712 should be sufficient such that air is not drawn into capillary tubing 724 during the measurement. The fluid level in reservoir 712, at the initiation of the measurement, should be approximately 2 mm below the top surface of fritted disc in fritted funnel 718. This can be confirmed by placing a small drop of fluid on the fritted disc and gravimetrically monitoring its slow flow back into reservoir 712. This level should not change significantly when piston/cylinder assembly 720 is positioned within funnel 718. The reservoir should have a sufficiently large diameter (e.g., ~14 cm) so that withdrawal of ~40 ml portions results in a change in the fluid height of less than 3 mm.

Prior to measurement, the assembly is filled with Jayco synthetic urine. The fritted disc in fritted funnel 718 is forward flushed so that it is filled with fresh synthetic urine. To the extent possible, air bubbles are removed from the bottom surface of the fritted disc and the system that connects the funnel to the reservoir. The following procedures are carried out by sequential operation of the 3-way stopcocks:

1. Excess fluid on the upper surface of the fritted disc is removed (e.g. poured) from fritted funnel 718.
2. The solution height/weight of reservoir 712 is adjusted to the proper level/value.
3. Fritted funnel 718 is positioned at the correct height relative to reservoir 712.
4. Fritted funnel 718 is then covered with fritted funnel cover 722.
5. The reservoir 712 and fritted funnel 718 are equilibrated with valves 728 and 740 of stopcock assemblies 726 and 738 in the open connecting position.
6. Valves 728 and 740 are then closed.
7. Valve 740 is then turned so that the funnel is open to the drain tube 744.
8. The system is allowed to equilibrate in this position for 5 minutes.
9. Valve 740 is then returned to its closed position.

Steps Nos. 7–9 temporarily "dry" the surface of fritted funnel 718 by exposing it to a small hydrostatic suction of ~5 cm. This suction is applied if the open end of tube 744 extends ~5 cm below the level of the fritted disc in fritted funnel 718 and is filled with synthetic urine. Typically ~0.2 g of fluid is drained from the system during this procedure. This procedure prevents premature absorption of synthetic urine when piston/cylinder assembly 720 is positioned within fritted funnel 718. The quantity of fluid that drains from the fritted funnel in this procedure (called the fritted funnel correction weight) is measured by conducting the PUP test (see below) for a time period of 15 minutes without piston/cylinder assembly 720. Essentially all of the fluid drained from the fritted funnel by this procedure is very quickly reabsorbed by the funnel when the test is initiated. Thus, it is necessary to subtract this correction weight from weights of fluid removed from the reservoir during the PUP test (see below).

0.9 g of hydrogel-forming absorbent polymer 760 (corresponding to a basis weight of 0.032 g/cm$^2$) is added to cylinder 754 and distributed evenly on screen 759. For most hydrogel-forming absorbent polymers, moisture content is typically less than 5%. For these polymers, the added polymer weight can be determined on a wet-weight (as it is) basis. For polymers having a moisture content greater than about 5%, the added polymer weight should be corrected for moisture (i.e., the added polymer should be 0.9 g on a dry-weight basis). Care is taken to prevent hydrogel-forming absorbent polymer 760 from adhering to the inside walls of cylinder 754. The piston 756 is slid into cylinder 754 and positioned on top of the hydrogel-forming absorbent polymer 760. The piston can be turned gently to help distribute the hydrogel-forming absorbent polymer. The piston/cylinder assembly 720 is placed on top of the frit portion of funnel 718, the weight 758 is slipped into piston 756, and the top of funnel 718 is then covered with fritted funnel cover 722. After the balance reading is checked for stability, the test is initiated by opening valves 728 and 740 so as to connect funnel 718 and reservoir 712. With auto initiation, data collection commences immediately, as funnel 718 begins to reabsorb fluid.

Data is recorded for a time period of 60 minutes.

Moisture content of the hydrogel-forming absorbent polymer is determined separately by measuring % weight loss after 3 hr @ 105° C. The measured moisture content is used to calculate the dry weight of hydrogel-forming polymer used in the PUP test.

$$PUP \text{ capacity } (gm/gm) = [W_r(t=0) - W_r(t=60 \text{ min}) - W_{fc}]/\{W_{hfap;dry\,basis}\}$$

where $W_r(t=0)$ is the weight in grams of reservoir 712 prior to initiation, $W_r(t=60 \text{ min})$ is the weight in grams of reservoir 712 at 60 minutes, $W_{fc}$ is the fritted funnel correction weight in grams (measured separately), and $W_{hfap;dry\,basis}$ is the dry weight in grams of the hydrogel-forming absorbent polymer.

3. Porosity of Hydrogel Layer (PHL)

This test determines the Porosity of the Hydrogel Layer (PHL) formed from hydrogel-forming absorbent polymer that is swollen in Jayco synthetic urine under a confining pressure. The objective of this test is to assess the ability of the hydrogel layer formed from a hydrogel-forming absorbent polymer to remain porous when the polymer is present at high concentrations in an absorbent member and exposed to usage mechanical pressures. PHL is the fractional volume of the layer that is not occupied by hydrogel. An excluded-volume method is used to measure PHL under a confining pressure.

PHL is measured using a modified version of the piston/cylinder apparatus used in the SFC method. The 0.118M NaCl solution used in the SFC method is modified for the PHL measurement by dissolving a high molecular weight Blue Dextran polymer in sufficient quantity such that the resultant solution has an optical absorbance of about 0.8 absorbance units at the polymer's absorption maximum of about 617 nm. The molecular weight of the Blue Dextran polymer is sufficiently high such that the polymer is excluded from the hydrogel. The hydrogel layer is formed and its porosity is measured under a mechanical confining pressure of 0.3 psi (about 2 kPa).

The hydrogel layer used for PHL measurements is formed by swelling approximately 0.9 g of a hydrogel-forming absorbent polymer in the PHL piston/cylinder apparatus with Jayco synthetic urine for a time period of about 60 minutes. At the end of this period, the thickness of the hydrogel layer is determined. The fluid contained in voids within the hydrogel layer is then exchanged with the 0.118M NaCl solution containing Blue Dextran (SBDS) by flowing an excess of the SBDS (optical absorbance equals $A_i$) through the hydrogel layer under a low hydrostatic pressure. For a hydrogel-forming absorbent polymer whose uptake of Jayco versus time has substantially leveled off, the NaCl concentration of SBDS has been found to maintain the thickness of the hydrogel layer substantially constant during this exchange step. For some hydrogel-forming absorbent polymers, small changes in thickness can occur as a result of polymer swelling or deswelling. Flow of SBDS through the hydrogel layer is continued until exchange is complete. The flow of SBDS is then stopped, any excess SBDS either above or below the hydrogel layer is allowed to drain out or is otherwise removed. Voids within the hydrogel layer remain fully saturated with SBDS. The thickness of the hydrogel layer ($t_f$) is then remeasured ($t_f$) and multiplied by the area of the cylinder ($A_c$) to obtain the volume of the hydrogel layer ($V_{hgl}$). SBDS contained in voids within the hydrogel layer is then flushed out using an excess of 0.118M NaCl solution (SS) and is quantitatively collected. Flushing with SS is continued until essentially all of the Blue Dextrin is extracted from the hydrogel layer. The volume of the collected solution containing the extracted Blue Dextran ($V_f$) is determined either volumetrically or gravimetrically and its optical absorbance ($A_f$) is measured. The void volume ($V_v$) within the hydrogel layer is determined from the measured values of $V_f$, $A_i$, and $A_f$. The value of $V_v$ is divided by $V_{hgl}$ to determine the porosity of the hydrogel layer.

Figure 12:
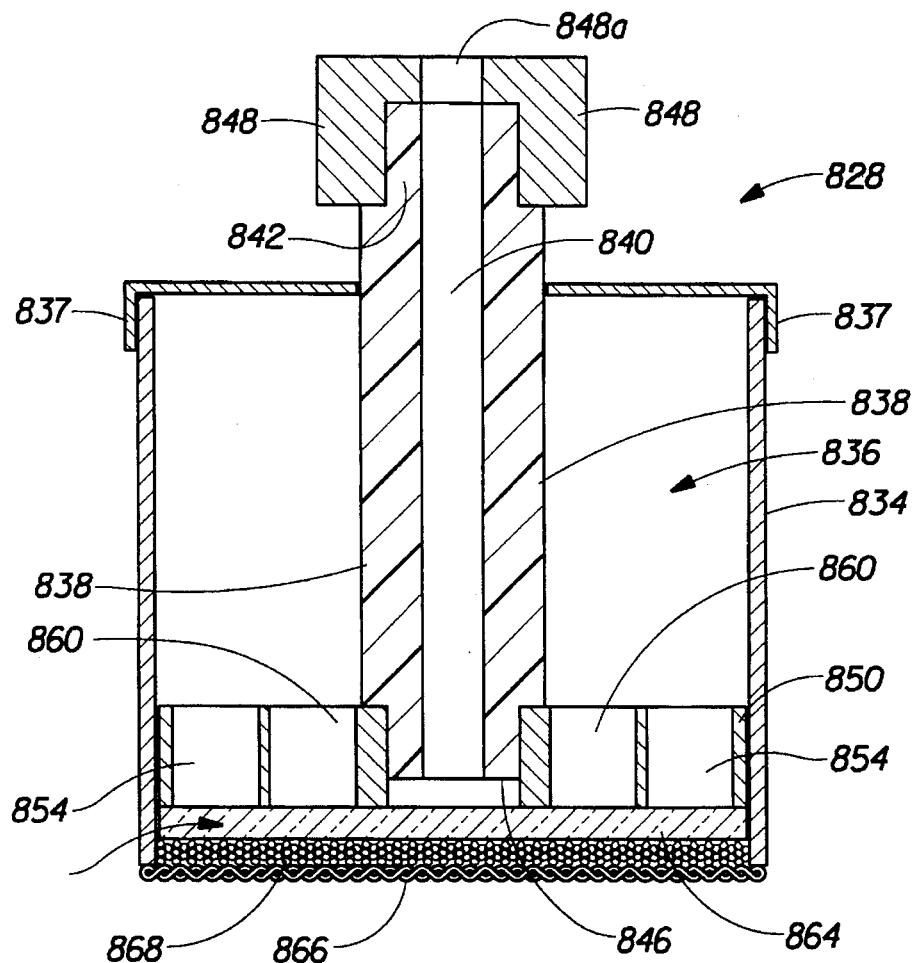
FIG. 12 represents a sectional view of the piston/cylinder assembly used to measure the porosity of the hydrogel-forming absorbent polymers.

A suitable piston/cylinder apparatus for this test is shown in FIG. 12 and is similar to the piston/cylinder apparatus shown in FIG. 8. Referring to FIG. 12, apparatus 828 basically consists of a cylinder 834, a piston generally indicated as 836 and a cover 837 provided with holes for piston 836 and solution delivery/removal (not shown). As shown in FIG. 12, piston 836 consists of a generally cylindrical LEXAN® shaft 838 having a concentric cylindrical hole 840 bored down the longitudinal axis of the shaft. Both ends of shaft 838 are machined to provide ends 842 and 846. A weight indicated as 848 rests on end 842 and has a cylindrical hole 848a bored through the center thereof.

Figure 13:
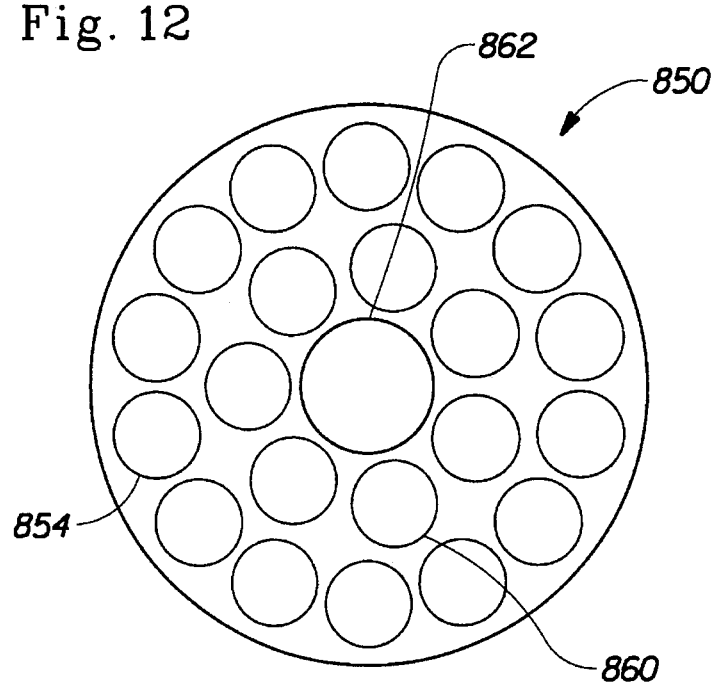
FIG. 13 represents a plan view of the bottom of the piston head from the piston/cylinder assembly shown in FIG. 12.

Inserted on the other end 846 is a generally circular piston head 850. Piston head 850 is sized so as to slidably move inside cylinder 834. As particularly shown in FIG. 13, piston head 850 is provided with inner and outer concentric rings containing seven and fourteen approximately 0.375 inch cylindrical holes, respectively, indicated generally by arrows 860 and 854. The holes in each of these concentric rings are bored from the top to bottom of piston head 850. Piston head 850 also has cylindrical hole 862 bored in the center thereof to receive end 846 of shaft 838.

Attached to bottom end of cylinder 834 is a No. 400 mesh stainless steel cloth screen 866 that is biaxially stretched to tautness prior to attachment. Attached to bottom end of piston head 850 is a No. 400 mesh stainless steel cloth screen 864 that is biaxially stretched to tautness prior to attachment. The sample of hydrogel-forming absorbent polymer indicated as 868 is supported on screen 866.

Cylinder 834 is bored from a transparent LEXAN® rod or equivalent and has an inner diameter of 6.00 cm (area=28.27 cm$^2$), a wall thickness of approximately 0.5 cm, and a height of approximately 6.0 cm. Piston head 850 is machined from a LEXAN® rod. It has a height of approximately 0.625 and a diameter sized such that it fits within the cylinder with minimum wall clearances, but still slides freely. Hole 862 in the center of the piston head 850 has a threaded 0.625 inch opening (18 threads/inch) for end 846 of shaft 838. Shaft 838 is machined from a LEXAN® rod and has an outer diameter of 0.875 inches and an inner diameter of 0.250 inches. End 846 is approximately 0.5 inches long and is threaded to match hole 862 in piston head 850. End 842 is approximately an inch long and 0.623 inches in diameter, forming an annular shoulder to support the stainless steel weight 848. Fluid passing through the hole 840 in shaft 838 can directly access screen 864. The annular stainless steel weight 848 has an inner diameter of 0.625 inches, so that it slips onto end 842 of shaft 838 and rests on the annular shoulder formed therein. The combined weight of piston 836 and weight 848 equals approximately 596 g, which corresponds to a pressure of 0.3 psi for an area of 28.27 cm$^2$. Cover 837 is machined from LEXAN® or its equivalent and is dimensioned to cover the top of cylinder 834. It has an 0.877 inch opening in the center thereof for shaft 838 of piston 836 and a second opening near the edge thereof for solution delivery/removal.

When solutions are flowed through the piston/cylinder apparatus, the cylinder 834 generally rests on a 16 mesh rigid stainless steel support screen (not shown) or equivalent.

A spectrophotometer capable of measuring optical absorbance at 617 nm with an accuracy of at least 0.001 absorbance units (e.g., Bausch & Lomb Spectronic 21 or equivalent) is used for optical absorbance measurements. Optical absorbance is measured to an accuracy of at least 0.001 absorbance units, relative to a 0.118M NaCl reference solution.

A Blue Dextran polymer having an average molecular weight of about 2,000,000 (Sigma, cat. no. D5376 or equivalent) is used for the measurement.

A 0.118M NaCl solution (SS) is prepared by dissolving 6.896 g NaCl (Baker Analyzed Reagent or equivalent) to 1.0 liters with distilled water. A quantity of Blue Dextran sufficient to give an optical absorbance of about 0.8 absorbance units (typically about 0.1 wt %) is dissolved in the NaCl solution. Optical absorbance ($A_i$) of this saline Blue Dextran solution (SBDS) is determined relative to a 0.118M NaCl reference solution.

The thickness of hydrogel layer 868 in cylinder 834 is measured to an accuracy of at least about 0.1 min. Any method having the requisite accuracy can be used, as long as the weights are not removed and the hydrogel layer is not additionally compressed or disturbed during the measurement. Using a caliper gauge (e.g., Manostat 15-100-500 or equivalent) to measure the vertical distance between the bottom of the stainless steel weight 848 and the top of cover 837, relative to this distance with no hydrogel layer 868 in cylinder 834 is acceptable. Also acceptable is the use of a depth gauge (e.g., Ono Sokki EG-225 or equivalent) to measure the position of piston 836 or stainless steel weight 848 relative to any fixed surface, compared to its position with no hydrogel layer in cylinder 834.

An analytical balance with an accuracy of at least 0.001 g (e.g., Mettier AE200) is used to determine the weight of hydrogel-forming polymer.

The PHL measurement is performed at ambient temperature (i.e., 20°–25° C.) and is carried out as follows:

A 0.9 gm aliquot of hydrogel-forming absorbent polymer (corresponding to a basis weight of 0.032 gm/cm$^2$) is added to cylinder 834 and distributed evenly on screen 866. For most hydrogel-forming absorbent polymers, moisture content is typically less than 5%. For these, the quantity of hydrogel-forming absorbent polymer to be added can be determined on a wet-weight (as is) basis. For hydrogel-forming absorbent polymers having a moisture content greater than about 5%, the added polymer weight should be corrected for moisture (i.e., the added polymer should be 0.9 g on a dry-weight basis). Care is taken to prevent hydrogel-forming absorbent polymer from adhering to the cylinder walls. Piston 836 (minus weight 848) is inserted into cylinder 834 and positioned on top of the dry hydrogel-forming absorbent polymer 868. If necessary, piston 836 can be turned gently to more-uniformly distribute the hydrogel-forming absorbent polymer on screen 866. Cylinder 834 is the covered with cover 837 and weight 848 is then positioned on end 842 of shaft 838.

A fritted disc (coarse or extra coarse) having a diameter greater than that of cylinder 834 is positioned in a wide/shallow flat-bottomed container that is filled to the top of the fritted disc with Jayco synthetic urine. The piston/cylinder assembly 828 is then positioned on top of this fritted glass disc. Jayco synthetic urine from the container passes through the fritted disc and is absorbed by the hydrogel-forming absorbent polymer 868. As the polymer absorbs fluid, a hydrogel layer is formed in cylinder 834. After a time period of 60 minutes, the thickness of the hydrogel layer is determined. Care is taken that the hydrogel layer does not lose fluid or take in air during this procedure.

The piston/cylinder assembly 828 is then positioned on a 16 mesh rigid stainless steel support screen. SBDS is then added to cylinder 834 through the fluid delivery hole (not shown) in cylinder cover 837 and allowed to flow through piston head 850 and hydrogel layer 868, exiting the cylinder through cylinder screen 866. A convenient apparatus for delivering SBDS to the cylinder and maintaining a constant but low hydrostatic pressure of SBDS (e.g., up to about 5 cm water) is the constant hydrostatic head delivery apparatus shown in FIG. 7 (references numbers 612 through 626). Solution exiting through cylinder screen 866 is periodically sampled and its optical absorbance measured. Flow of SBDS is continued until exchange by SBDS of the original solution contained in voids within hydrogel layer 868 is essentially complete, as indicated by the exiting solution having an optical absorbance approximately equal to that of SBDS (e.g., within about 0.001 absorbance unit). Typically, the total volume of SBDS used in this step is approximately 10*$V_{hgl}$. The addition of SBDS is then stopped and excess SBDS above piston head 850 and within the cylindrical holes 854 and 860 in piston head 850-is allowed to drain through hydrogel layer 868 and out of cylinder 834 through cylinder screen 866. The thickness of the hydrogel layer ($t_f$) is then remeasured. Substantially all of any residual solution remaining above piston head 850, within cylindrical holes 854 and 860 in piston head 850, or below cylinder screen 866 that does not spontaneously drain is then otherwise removed (e.g., using a disposable pipette) while minimizing any disturbance to the hydrogel layer. The volume ($V_r$) of any residual SBDS remaining in the gap between piston head 850 and cylinder 834 is estimated from geometric considerations (i.e., the fractional area ($F_a$) of the gap between piston head 850 and the inner wall of cylinder 834 that is filled with SBDS multiplied by the calculated volume ($V_g$) between the piston head and the cylinder wall). Voids within hydrogel layer 868 should remain fully saturated with SBDS. The piston/cylinder assembly 828 is then re-positioned, if necessary, on the 16 mesh rigid stainless steel support screen. SS is then added to cylinder 834 through the solution delivery/removal hole (not shown) in cylinder cover 837 and allowed to flow through piston head 850 and hydrogel layer 868. Solution exiting the cylinder 834 through cylinder screen 866 in this step is quantitatively collected. A convenient apparatus for delivering SS to the cylinder and maintaining a constant but low hydrostatic pressure of SS (e.g., up to about 5 cm water) is the constant hydrostatic head delivery apparatus shown in FIG. 7 (references numbers 612 through 626). Optionally, weight 848, cylinder cover 837 and piston 836 can be removed just prior to the SS exchange step (without removal of hydrogel-forming polymer or SBDS) to facilitate access to and removal of Blue Dextran contained in voids within the hydrogel layer. Solution exiting through cylinder screen 866 is periodically sampled and its optical absorbance is measured. Addition of SS is continued until the flushing out of Blue Dextran contained in the voids within hydrogel layer 868 is essentially complete, as indicated by the exiting solution having an optical absorbance approximately equal to zero (e.g., less than about 0.001 absorbance unit). Typically, the total volume of SS used in this step is approximately $10*V_{hgl}$. The use of excess SS in this step should be avoided, since it can result in excessive dilution of the Blue Dextran. The volume of the solution collected in this step ($V_f$) is determined either gravimetrically or volumetrically. After mixing, the optical absorbance of this final solution ($A_f$) is measured.

For a hydrogel layer having a very high permeability, a lower hydrostatic pressure is typically used in the SBDS and SS flushing steps or solution can be otherwise added in a step-wise fashion (for example, by using a pipette) to control the rate of flow and allow for periodic sampling.

For some hydrogel-forming absorbent polymers (e.g., those having extremely low permeability), absorption of Jayco solution by the hydrogel may not have leveled off after one hour and thus additional fluid may be absorbed during the solution exchange steps. For these hydrogel-forming polymers, it is optional to extend the time for Jayco solution absorption to longer periods (e.g., 16 hours). For hydrogel layers having very low permeability, longer time periods for the solution exchange steps may also be required.

If the thickness of the hydrogel layer changes as a result of the SBDS exchange step by more than about 10%, then the concentration of NaCl in this solution needs to be adjusted appropriately so as to reduce the extent of thickness change.

The size-exclusion polymer used for this method should not be appreciably adsorbed by the hydrogel. For e.g., cationic polymers, it may be necessary to use an alternative size-exclusion polymer and/or use an alternative method (e.g., chromatography) for determining relative solution concentrations of the size-exclusion polymer.

$V_v$ and PHL is calculated using the following formulas:

$$V_v = V_f * A_f/A_i - V_r$$

$$PHL = V_v/V_{hgl}$$

The average of at least two determinations should be reported.

The following is an example of how PHL is calculated according to the present invention:

A hydrogel layer is formed from 0.9052 g of hydrogel-forming polymer sample 2.5 of Example 2 under a confining pressure of 0.3 psi by swelling with Jayco synthetic urine for 60 minutes. The thickness of the formed hydrogel layer is 1.079 cm. Solution contained in voids within the hydrogel layer is exchanged with SBDS having an optical absorbance at 617 nm of 0.814 absorbance units. The measured thickness of the hydrogel layer after SBDS exchange is 1.065 cm, a decrease in thickness of 1.3% relative to the thickness before exchange with SBDS. After drainage, approximately 50% of the area between piston head and cylinder contains SBDS. Based on the dimensions of the cylinder and piston head (outer diameter of piston head=5.964 cm; inner diameter of cylinder=6.000 cm; height of piston head=1.64 cm), the volume of the gap between piston head and cylinder is 0.55 cc. SBDS in voids within the hydrogel layer is exchanged with SS. The solution collected in this exchange step has a volume of 201.2 cc (determined gravimetrically) and an optical absorbance of 0.023 absorbance units. PHL is calculated as follows:

$$V_{hgl} = t_f * A_c = (1.065 \text{ cm})*(28.27 \text{ cm}^2) = 30.1 \text{ cm}^3$$

$$V_r = F_a * V_g = (0.5)*(0.55 \text{ cm}^3) = 0.28 \text{ cm}^3$$

$$V_v = V_f * A_f/A_i - V_r = (201.2 \text{ cm}^3)*(0.023/0.814) - 0.28 \text{ cm}^3 = 5.41 \text{ cm}^3$$

$$PHL = V_v/V_{hgl} = (5.41 \text{ cm}^3)/(30.1 \text{ cm}^3) = 0.180$$

4. Gel Volume

For most hydrogel-forming absorbent polymers, gel volume is determined by the method described in U.S. Re. Pat. No. 32,649 (Brandt et al), reissued Apr. 19, 1988 (herein incorporated by reference) but using Jayco synthetic urine. The gel volume is calculated on a dry-weight basis. The dry weight used in the gel volume calculation is determined by oven drying the hydrogel-forming absorbent polymer at 105° C. for three hours.

An alternative method for measuring gel volume can be used for hydrogel-forming absorbent polymers that adsorb Blue Dextran (see gel volume method above) to the surfaces of the formed hydrogel (e.g., polymers prepared from cationic monomers). For these hydrogel-forming polymers, the Absorptive Capacity test is used, but the dry weight of the hydrogel-forming polymer is used in the calculation instead of the as-is weight. See U.S. Pat. No. 5,124,188 (Roe et al), issued Jun. 23, 1992 at Columns 27-28 (herein incorporated by reference) for description of the Absorptive Capacity test.

6. Gel Strength

The gel strength or shear modulus of the formed hydrogel is determined using the Gel Strength/Shear Modulus Determination method described in the referenced U.S. Re. Pat. No. 32,649, with the following modifications: (i) the hydrogel-forming absorbent polymer is swollen in Jayco synthetic urine, (ii) an oscillatory rheometer having a parallel plate configuration, wherein the gap is set at 1.0 mm, is used, (iii) the formula for calculating shear modulus is modified for the above parallel plate configuration, (iv) the strain amplitude is less than about 0.3%, and (v) the hydrogel-forming polymer is ground (e.g., so it passes through a No 45 U.S.A. Standard Testing Sieve (350 microns openings)), if necessary, so the formed hydrogel packs at a high loading factor between the plates of the oscillatory rheometer.

What is claimed is:

1. An absorbent member for the containment of aqueous body fluids, which comprises at least one region comprising hydrogel-forming absorbent polymer in a concentration of from about 60 to 100% by weight, said hydrogel-forming polymer providing a gel continuous fluid transportation zone when in a swollen state and having:

(a) a porosity of at least about 0.15;
(b) a Performance under Pressure (PUP) capacity value of at least about 23 g/g under a confining pressure of 0.7 psi (5 kPa);
(c) a basis weight of at least about 10 gsm;

said region having, when subjected to normal use conditions, sufficient wet integrity such that said gel continuous zone substantially maintains its ability to acquire and transport said body fluids through said gel continuous zone.

2. The absorbent member of claim 1 wherein said hydrogel-forming polymer has anionic functional groups.

3. The absorbent member of claim 2 wherein said anionic functional groups of said hydrogel-forming polymer are carboxy groups.

4. The absorbent member of claim 3 wherein said hydrogel-forming polymer is surface crosslinked.

5. The absorbent member of claim 4 wherein said hydrogel-forming polymer is selected from the group consisting of hydrolyzed starch-acrylonitrile graft copolymers; partially neutralized hydrolyzed starch-acrylonitrile graft copolymers; starch-acrylic acid graft copolymers, partially neutralized starch-acrylic acid graft copolymers; saponified vinyl acetate-acrylic ester copolymers; hydrolyzed acrylonitrile copolymers; hydrolyzed acrylamide copolymers; slightly network crosslinked products of any of the foregoing copolymers; partially neutralized polyacrylic acid; slightly network crosslinked products of partially neutralized polyacrylic acid; and mixtures thereof.

6. The absorbent member of claim 1 wherein said hydrogel-forming polymer is in the form of particles.

7. The absorbent member of claim 6 wherein said particles of said hydrogel-forming polymer have a particle size in the range of from about 20 to about 1500 microns.

8. The absorbent member of claim 7 wherein said hydrogel-forming polymer has a mass median particle size of from about 100 to about 800 microns.

9. The absorbent member of claim 1 where in said hydrogel-forming polymer has a porosity of from about 0.15 to about 0.40 and a PUP capacity value of from about 23 to about 35 g/g.

10. The absorbent member of claim 1 wherein said hydrogel-forming polymer has a porosity of at least about 0.18.

11. The absorbent member of claim 10 wherein said hydrogel-forming polymer has a porosity of from about 0.18 to about 0.25.

12. The absorbent member of claim 10 wherein said hydrogel-forming polymer has a porosity of at least about 0.20.

13. The absorbent member of claim 1 wherein said hydrogel-forming polymer has a Saline Flow Conductivity (SFC) value of at least about $30 \times 10^{-7}$ cm$^3$ sec/g.

14. The absorbent member of claim 13 wherein said hydrogel-forming polymer has an SFC value of from about 30 to about $1000 \times 10^{-7}$ cm$^3$ sec/g.

15. The absorbent member of claim 14 wherein said hydrogel-forming polymer has an SFC value of from about 50 to about $500 \times 10^{-7}$ cm$^3$ sec/g.

16. The absorbent member of claim 15 wherein said hydrogel-forming polymer has an SFC value of from about 100 to about $350 \times 10^{-7}$ cm$^3$ sec/g.

17. The absorbent member of claim 1 wherein said hydrogel-forming polymer has about 15% or less extractable polymer.

18. The absorbent member of claim 17 wherein said hydrogel-forming polymer has about 10% or less extractable polymer.

19. The absorbent member of claim 1 wherein said hydrogel-forming polymer has a gel volume of at least about 20 g/g.

20. The absorbent member of claim 19 wherein said hydrogel-forming polymer has a gel volume of from about 25 to about 80 g/g.

21. The absorbent member of claim 20 wherein said hydrogel-forming polymer has a gel volume of from about 30 to about 70 g/g.

22. The absorbent member of claim 19 wherein said hydrogel-forming polymer has a gel strength of at least about 10,000 dynes/cm$^2$.

23. The absorbent member of claim 1 wherein the basis weight of said hydrogel-forming polymer in said region is at least about 20 gsm.

24. The absorbent member of claim 23 wherein the basis weight of said hydrogel-forming polymer in said region is at least about 50 gsm.

25. The absorbent member of claim 24 wherein the basis weight of said hydrogel-forming polymer in said region is at least about 100 gsm.

26. The absorbent member of claim 1 wherein said region comprises from about 70 to 100% of said hydrogel-forming polymer.

27. The absorbent member of claim 26 wherein said region comprises from about 80 to 100% of said hydrogel-forming polymer.

28. An absorbent core for acquiring, distributing and storing body fluids, which comprises a fluid storage absorbent layer comprising fibrous matrix having at least one region containing particles of a surface crosslinked hydrogel-forming absorbent polymer having carboxy functional groups, said hydrogel-forming polymer being present in said region in a concentration of from about 60 to 100% by weight, said hydrogel-forming polymer providing a gel continuous fluid transportation zone when in a swollen state and having:

(a) a porosity of from about 0.15 to about 0.40;
(b) a Performance under Pressure (PUP) capacity value of at least about 23 g/g under a confining pressure of 0.7 psi (5 kPa);
(c) a basis weight of at least about 20 gsm;
(d) a Saline Flow Conductivity (SFC) value of from about 30 to about $1000 \times 10^{-7}$ cm$^3$ sec/g;
(e) about 15% or less extractable polymer;
(f) a gel volume of from about 25 to about 80 g/g;

said region having, when subjected to normal use conditions, sufficient wet integrity such that said gel continuous zone substantially maintains its ability to acquire and transport body fluids through said gel continuous zone.

29. The absorbent core of claim 28 which further comprises a fluid acquisition layer.

30. The absorbent core of claim 29 wherein said fluid layer comprises chemically stiffened cellulosic fibers.

31. The absorbent core of claim 28 wherein said storage layer comprises a layer of said hydrogel-forming polymer contained between a first fibrous layer and a second fibrous layer.

32. The absorbent core of claim 28 wherein said storage layer further comprises thermoplastic material.

33. The absorbent core of claim 32 wherein said storage layer is thermally bonded.

34. The absorbent core of claim 32 wherein said thermoplastic material is thermoplastic binder fibers.

35. The absorbent core of claim 28 wherein said region comprises from about 70 to 100% of said hydrogel-forming polymer.

36. The absorbent core of claim 35 wherein said region comprises from about 80 to 100% of said hydrogel-forming polymer.

37. The absorbent core of claim 28 wherein the basis weight of said hydrogel-forming absorbent polymer in said region is at least about 50 gsm.

38. The absorbent core of claim 28 wherein said hydrogel-forming polymer is selected from the group consisting of hydrolyzed starch-acrylonitrile graff copolymers; partially neutralized hydrolyzed starch-acrylonitrile graff copolymers; starch-acrylic acid graff copolymers, partially neutralized starch-acrylic acid graff copolymers; saponified vinyl acetate-acrylic ester copolymers; hydrolyzed acrylonitrile copolymers; hydrolyzed acrylamide copolymers; slightly network crosslinked products of any of the foregoing copolymers; partially neutralized polyacrylic acid; slightly network crosslinked products of partially neutralized polyacrylic acid; and mixtures thereof.

39. The absorbent core of claim 28 wherein said hydrogel-forming polymer has:

(a) a porosity of from about 0.18 to about 0.25;

(b) a Performance under Pressure (PUP) capacity value of from about 23 to about 35 g/g under a confining pressure of 0.7 psi (5 kPa);

(c) a basis weight of at least about 50 gsm;

(d) a Saline Flow Conductivity (SFC) value of from about 50 to about $500 \times 10^{-7}$ cm$^3$ sec/g;

(e) about 10% or less extractable polymer.

40. The absorbent core of claim 28 wherein said hydrogel-forming polymer has a mass median particle size of from about 100 to about 800 microns.

41. The absorbent core of claim 28 wherein said hydrogel-forming polymer has a gel strength of at least about 20,000 dynes/cm$^2$.

42. An absorbent article comprising a fluid pervious topsheet, a backsheet and the absorbent core of claim 28 positioned between said topsheet and said backsheet.

43. The absorbent article of claim 42 which is a diaper.

44. The absorbent article of claim 42 which is a training pant.

45. The absorbent article of claim 42 which is a catamenial pad.

* * * * *

UNITED STATES PATENT AND TRADEMARK OFFICE
CERTIFICATE OF CORRECTION

PATENT NO. : 5,562,646
DATED : Oct. 8, 1996
INVENTOR(S) : S. A. Goldman et al.

It is certified that error appears in the above-identified patent and that said Letters Patent is hereby corrected as shown below:

In Col. 2, line 33, "mounts" should read --amounts--.

In Col. 5, line 29, "Byedy" should read --Byerly--.

In Col. 6, line 19, "PIE" should read --PHL--.

In Col. 10, line 19, "acrylonitfile" should read --acrylonitrile--.

In Col. 10, line 24, "acrylonitfile" should read --acrylonitrile--.

In Col. 20, line 34, "Prevail" should read --PreVal--.

In Col. 20, line 65, "Drierite" should read --Dricrite--.

In Col. 23, line 63, "previous" should read --pervious--.

In Col. 24, line 44, "eellulosic" should read --cellulosic--.

In Col. 25, line 25, "stiflened" should read --stiffened--.

In Col. 25, line 28, "cured" should read --curled--.

In Col. 25, line 40, "stiflened" should read --stiffened--.

In Col. 25, line 44, "stiflened" should read --stiffened--.

In Col. 26, line 15, "cuffed" should read --curled--.

In Col. 26, line 15, "cuff" should read --curl--.

In Col. 26, line 18, "cuff" should read --curl--.

In Col. 26, line 19, "cuffing" should read --curling--.

In Col. 26, line 20, "cud" should read --curl--.

In Col. 26, line 36, "stiflened" should read --stiffened--.

In Col. 27, line 7, "stiflened" should read --stiffened--.

In Col. 27, line 10, "stiflened" should read --stiffened--.

In Col. 27, line 63, "These suffactants" should read --These surfactants--.

UNITED STATES PATENT AND TRADEMARK OFFICE
CERTIFICATE OF CORRECTION

PATENT NO. : 5,562,646
DATED : Oct. 8, 1996
INVENTOR(S) : S. A. Goldman et al.

It is certified that error appears in the above-identified patent and that said Letters Patent is hereby corrected as shown below:

In Col. 29, line 7, "previous" should read --pervious--.

In Col. 35, line 13, "previous" should read --pervious--.

In Col. 38, line 62, "stiflened" should read --stiffened--.

In Col. 39, line 15, "uncfimped" should read --uncrimped--.

In Col. 45, line 2, "previous" should read --pervious--.

In Col. 45, line 64, "coethylene" should read --co-ethylene--.

In Col. 46, line 11, "layer." should read --layer--.

In Col. 46, line 11, "are hotmelt" should read --are hot-melt--.

In Col. 46, line 26, "alter" should read --after--.

In Col. 46, line 55, "alter" should read --after--.

In Col. 47, line 13, "denjer" should read --denier--.

In Col. 47, line 36, "denjer" should read --denier--.

In Col. 56, line 4, "flitted" should read --fritted--.

In Col. 56, line 8, "flitted" should read --fritted--.

In Col. 57, line 22, "flitted" should read --fritted--.

In Col. 57, line 32, "flitted" should read --fritted--.

In Col. 57, line 37, "flitted" should read --fritted--.

In Col. 57, line 54, "generally" should read --Generally--.

In Col. 62, line 55, "tings" should read --rings--.

In Col. 62, line 61, "shatt" should read --shaft--.

In Col. 63, line 52, "min." should read --mm.--.

In Col. 63, line 66, "Mettier" should read --Mettler--.

UNITED STATES PATENT AND TRADEMARK OFFICE
CERTIFICATE OF CORRECTION

PATENT NO. : 5,562,646
DATED : Oct. 8, 1996
INVENTOR(S) : S. A. Goldman et al.

It is certified that error appears in the above-identified patent and that said Letters Patent is hereby corrected as shown below:

In Col. 69, line 12, "graff" should read --graft--.

In Col. 69, line 13, "graff copolymers" should read --graft copolymers--.

In Col. 69, line 14, "acid graff" should read --acid graft--.

In Col. 69, line 15, "graff" should read --graft--.

Signed and Sealed this

Twenty-third Day of September, 1997

BRUCE LEHMAN

Attest:

Attesting Officer

Commissioner of Patents and Trademarks